US008222251B2

(12) United States Patent
Kaizerman et al.

(10) Patent No.: US 8,222,251 B2
(45) Date of Patent: Jul. 17, 2012

(54) PYRIDOPYRIDAZINE COMPOUNDS, COMPOSITIONS AND METHODS OF USE

(75) Inventors: Jacob Kaizerman, Redwood City, CA (US); Brian Lucas, San Francisco, CA (US); Dustin McMinn, Pacifica, CA (US); Robert Zamboni, Beaconsfield (CA)

(73) Assignee: Amgen Inc., Thousand Oaks, CA (US)

( * ) Notice: Subject to any disclaimer, the term of this patent is extended or adjusted under 35 U.S.C. 154(b) by 872 days.

(21) Appl. No.: 12/232,000

(22) Filed: Sep. 5, 2008

(65) Prior Publication Data

US 2009/0099173 A1 Apr. 16, 2009

Related U.S. Application Data

(60) Provisional application No. 60/967,859, filed on Sep. 7, 2007.

(51) Int. Cl.
*A01N 43/58* (2006.01)
*A61K 31/50* (2006.01)
*C07D 487/00* (2006.01)

(52) U.S. Cl. ........................................ 514/250; 544/236

(58) Field of Classification Search .................. 544/235, 544/236; 514/250
See application file for complete search history.

(56) References Cited

FOREIGN PATENT DOCUMENTS

| | | | |
|---|---|---|---|
| WO | WO 2005/033288 | A | 4/2005 |
| WO | WO 2006/028958 | A | 3/2006 |
| WO | WO 2006/050506 | A | 5/2006 |

OTHER PUBLICATIONS

Pinedo et al, "Translational Research . . . ", The Oncologist 2000; 5(suppl1); 1-2. [www.The Oncologist.com].*

McMahon, G., VEGF Receptor Signaling in Tumor Angiogenisis. The Oncologist 2000;5(suppl 1):3-10. [www.The Oncologist.com].*

* cited by examiner

*Primary Examiner* — Paul V. Ward

(74) *Attorney, Agent, or Firm* — Joseph W. Bulock

(57) ABSTRACT

The present invention relates generally to compounds represented in Formula I, pharmaceutical compositions comprising them and methods of treating of diseases or disorders such as cancer.

I

B—C, A, D, R1, R2, Cy1, N, N—L—R5, N—N, R4, R3

32 Claims, No Drawings

PYRIDOPYRIDAZINE COMPOUNDS, COMPOSITIONS AND METHODS OF USE

CROSS REFERENCE TO RELATED APPLICATION

This application claims the benefit of U.S. Provisional Application No. 60/967,859 filed Sep. 7, 2007, which is incorporated herein by reference in its entirety.

FIELD OF THE INVENTION

This invention relates generally to the field of medicine and, more specifically, to compounds and pharmaceutical compositions comprising them, uses and methods for treating cancer.

BACKGROUND OF THE INVENTION

Members of the Hedgehog (Hh) family of signaling molecules mediate many important short and long range patterning processes during invertebrate and vertebrate development. Pattern formation is the activity by which embryonic cells form ordered spatial arrangements of differentiated issues. Hedgehog proteins were first discovered in *Drosophila*. Although some crucial differences exist, the signalling mechanisms are generally well conserved between *Drosophila* and higher organisms. In the fly, a single Hh gene regulates segmental and imaginal disc patterning. In contrast, in vertebrates, an Hh gene family is involved in the control of left-right asymmetry, polarity in the CNS, somites and limb, organogenesis, chondrogenesis and spermatogenesis. Three Hh homologues have been identified in humans: Sonic hedgehog (SHH), Indian hedgehog (IHH) and Desert hedgehog (DHH). The Hh signaling cascade is initiated by Hh binding to the Patched proteins (PTCH1 in humans) on the target cell. In the absence of the Hh ligand, PTCH1 represses the activity of Smoothened (SMO in humans, Smo in mouse and smo in *Drosophila*), a G-protein-coupled receptor (GPCR)-like protein. Mammalian Hh signaling requires the presence of non-motile cilia to which SMO and other downstream pathway components localize to achieve activation of GLI transcription factors, the cubis interruptus (Ci) orthologues. The activator and repressor forms of Ci in mammals are represented by three separate zinc-finger proteins, with GLI1 and GLI2 functioning mostly as activators and GLI3 as a repressor. For review, see Rubin L. L. et al. (2006) *Nature Reviews*, vol 5, 1026-1033. The mechanism by which this signaling cascade regulates proliferation involves the activation of cyclins and cyclin-dependent kinases. The control of differentiation might be occurring via the production of other secreted proteins, including neurotrophic and angiogenic factors.

Medicinal chemistry efforts to identify inhibitors of Hh pathway began when Richard Keeler and co-workers isolated teratogens from *Veratrum californicum* in 1964. Subsequent research established that the previously known alkaloid jervine and the newly discovered alkaloid cyclopamine were able to induce cyclopia. Almost four decades later, the heptahelical bundle of Smo was identified as the site of binding of cyclopamine using its photoaffinity and fluorescent derivatives. Chen, J. et al. (2002) *Genes & Develop.* 16: 2743-2748; Chen, J. et al. (2002) *Proc. Natl. Acad. Sci. USA* 99: 14071-14076; Frank-Kamenetsky, M. et al. (2002) *J. Biol.* 1, article 10. Several assays are used to screen for antagonists to Smo in vitro. One of the assays for high throughput screening examines the overall activity of the Hh pathway in a cellular context by determining the degree of activity of the downstream effector protein GLI. Chen et al., supra. Cell lines of this type often incorporate a GLI dependent luciferase reporter for the assay readout. The luciferase signal may be boosted by other engineer modifications, such as the addition of biologically active Shh, (e.g., Shh with an octyl moiety attached to its N terminus), or the utilization of cell lines that lack PTCH1 function. Alternatively, direct binding to Smo can be measured through the displacement of a fluorescent cyclopamine derivative. In addition, tumor xenograft models based on SCLC, biliary, prostate, pancreatic and medulloblastoma lines can also be used.

In the recent years it was established that aberrant activation of the Hh signaling pathway can lead to cancer. Gorlin syndrome (GS), or nevoid basal cell carcinoma syndrome, is an autosomal dominant genetic disease that is characterized by development abnormalities and tumor predisposition. Virtually all individuals with Gorlin syndrome develop basal cell carcinomas (BCC), usually at multiple sites, and are predisposed to other kinds of cancer as well, especially medulloblastoma, a tumor of cerebellar granule neuron progenitor cells, rhabdomyosarcoma, a muscle tumor, as well as ovarian fibromas and sarcomas. Borzillo, G. et al. (2005) *Curr. Topics in Med. Chem.* 5: 147-157.

BCC is the most common human cancer, accounting for about 70% of human skin cancers, and representing at least one third of all cancer diagnosed in the US each year. More than 99% of BCC cases arise sporadically in the population, with only 0.5% of cases arising in individuals with GS. BCC rarely metastasizes, but can be locally aggressive and recurrent. Inactivating mutations in PTCH1 occur most commonly in these tumors. A subset of BCC is driven via mutations in SMO, and these mutations activate the pathway by generating proteins with decreased sensitivity to PTCH1 suppression.

Medulloblastoma (MB) is a brain tumor that forms in the cerebellum of children and young adults, and may be the end result of defect in cerebellar organogenesis. MB, in addition to BCC, has a well recognized involvement of the Hh pathway. The outcome of this cancer is almost invariably poor. Surgery with subsequent radiation or chemotherapy increases survival to greater than 50%, but there is severe treatment-associated morbidity, including mental retardation. Hh-pathway antagonists have been tested in cell culture and mouse models of medulloblastoma. A new class of SMO-binding Hh antagonists has been demonstrated to be very potent. Berman C. M. et al. (2002) *Science* 297: 1559-1561.

Hh pathway has been implicated in many other types of cancer, including pancreatic cancer, other tumors of the gastrointestinal (GI) tract and prostate cancer. Abnormal expression of SHH, PTCH1 and SMO has been shown early in the formation of human pancreatic tumors. Thayer, S. P. et al. (2003) *Nature* 425: 313-317. Several pancreatic cancer cell lines were found to be PTCH1 and SMO-positive and growth inhibited in vitro by cyclopamine, suggesting an active autocrine loop through which tumor cells both make and respond to Hh ligand. Furthermore, systemic treatment with cyclopamine slowed the growth of tumors formed when these cell lines are implanted into immunocompromised mice. Similar observations were made for pancreatic and other GI tumors. Berman, D. M. et al. (2003) *Nature* 425: 846-851. Similar data was provided for prostate cancer as well, including SHH overexpression in tumor biopsies, especially in higher Gleason grade tumors, and in vitro and in vivo inhibitory effects of cyclopamine on growth of prostate cancer cell lines. The Hh pathway was further implicated in prostate tumor metastasis, as the capacity of AT6.3 cells to metastasize to the lung was completely abrogated by cyclopamine, and AT2.1, a rarely metastasizing clone, could be induced to metastasize by overexpression of GLI1, in a cyclopamine-insensitive manner.

It has been demonstrated recently that Hh may be involved in the development of a significant subset of small cell lung carcinoma (SCLC). Watkins, D. N. et al. (2003) *Nature* 422: 313-317. In this study, Shh pathway components were found to be reactivated in a mouse model of acute airway damage caused by naphthalene. About 50-70% of SCLC lines and primary tumors expressed transcripts (SHH, PTCH1, GLI1) indicative of activated Shh signaling. Cyclopamine blocked the growth of only those cells with persistent Hh signaling, and this effect was abrogated by overexpression of GLI1. None of the effects of cyclopamine could be reproduced with tomatidine, a compound that is structurally similar but inactive against SMO.

These results demonstrate that Hh pathway is an important pharmacological target for a variety of cancers. Compounds and compositions of the current invention present an important treatment option for all tumors driven by inappropriate Hh signaling.

SUMMARY OF THE INVENTION

The present invention relates to compounds of Formula I

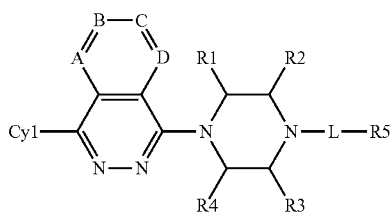

or a pharmaceutically acceptable salt thereof, wherein all substituents are as defined in Detailed Description.

The invention provides pharmaceutical compositions comprising compounds of Formula I, solvates, prodrugs and or pharmaceutically acceptable salts thereof and a pharmaceutically acceptable carrier.

In one aspect, the invention provides methods of treating cancer, comprising administering a therapeutically effective amount of a compound of Formula I or a pharmaceutically acceptable salt thereof to a subject in need thereof. In one aspect, cancer can be pancreatic cancer. In another aspect, cancer can be basal cell carcinoma, medulloblastoma, Gorlin syndrome, prostate or lung cancer. The invention further provides methods for treating cancer, further comprising administering a compound selected from the group consisting of antibiotics, alkylating agents, antimetabolite agents, hormonal agents, immunological agents and interferon-type agents.

In one aspect, the invention provides methods of treating angiogenesis in a subject, comprising administering a therapeutically effective amount of a compound of Formula I or a pharmaceutically acceptable salt thereof to a subject in need thereof. In another aspect, the invention provides methods of reducing blood flow in a tumor in a subject, comprising administering a therapeutically effective amount of a compound of Formula I or a pharmaceutically acceptable salt thereof to a subject in need thereof.

In one aspect, the subject can be human.

DETAILED DESCRIPTION OF THE INVENTION

I. Definitions

"Treating" or "treatment" of a disease includes: (1) preventing the disease, i.e., causing the clinical symptoms of the disease not to develop in a subject that may be or has been exposed to the disease or conditions that may cause the disease, or predisposed to the disease but does not yet experience or display symptoms of the disease, (2) inhibiting the disease, i.e., arresting or reducing the development of the disease or any of its clinical symptoms, or (3) relieving the disease, i.e., causing regression of the disease or any of its clinical symptoms.

The phrase "therapeutically effective amount" is the amount of the compound of the invention that will achieve the goal of prevention of the disorder or improvement in disorder severity and the frequency of incidence. The improvement in disorder severity includes the reversal of the disease, as well as slowing down the progression of the disease.

As used herein, "cancer" and "cancerous" refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon cancer, medulloblastoma, and head and neck cancer. While the term "cancer" as used herein is not limited to any one specific form of the disease, it is believed that the methods of the invention will be particularly effective for cancers which are found to be accompanied by aberrant signaling in Hh pathway.

Unless otherwise specified, the following definitions apply to terms found in the specification and claims:

The term "H" denotes a single hydrogen atom. This radical may be attached, for example, to an oxygen atom to form a hydroxyl radical.

The term "alkyl" by itself or as part of another substituent, means, unless otherwise stated, a straight or branched chain, or cyclic, saturated hydrocarbon having the indicated number of carbon atoms (i.e., $C_1$-$C_8$ means one to eight carbons). For example, $C_1$-$C_8$ alkyl is meant to include, but is not limited to methyl, ethyl, propyl, isopropyl, butyl, sec-butyl, tert-butyl, pentyl, isopentyl, neopentyl, hexyl, isohexyl, cyclohexyl, cyclohexylmethyl, cyclopropylmethyl and neohexyl.

The term "alkenyl" as used herein refers to a straight or branched chain unsaturated hydrocarbon having the indicated number of carbon atoms (i.e., $C_2$-$C_8$ means two to eight carbons) and at least one double bond. Examples of a $C_2$-$C_8$ alkenyl group include, but are not limited to, ethylene, propylene, 1-butylene, 2-butylene, isobutylene, sec-butylene, 1-pentene, 2-pentene, isopentane, 1-hexene, 2-hexene, 3-hexene, isohexane, 1-heptene, 2-heptene, 3-heptene, isoheptane, 1-octene, 2-octene, 3-octene, 4-octene, and isooctane.

The term "alkylene" refers to a divalent alkyl group (e.g., an alkyl group attached to two other moieties, typically as a linking group). Examples of a ($C_1$-$C_8$) alkylene include —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and —$CH_2CH_2CH_2CH_2CH_2CH_2CH_2$—, as well as branched versions thereof. The term "alkenylene" refers to a divalent alkenyl group (e.g., an alkenyl group attached to two other moieties, typically as a linking group). Examples of a $C_2$-$C_8$ alkenylene group include —CH═CH—, —$CH_2$CH═CH—, —$CH_2$CH═CH$CH_2$—, as well as branched versions thereof.

Typically, an alkyl, alkenyl, alkylene, or alkenylene group will have from 1 to 24 carbon atoms, with those groups having 10 or fewer carbon atoms being preferred in the present invention. A "lower alkyl" "lower alkenyl" or "lower alkylene" is a shorter chain alkyl or alkylene group, generally having eight or fewer carbon atoms.

The term "heteroatom" is meant to include oxygen (O), nitrogen (N), sulfur (S) and silicon (Si).

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S$(O)_2$—$CH_3$—CH═CH—O—$CH_3$, —Si$(CH_3)_3$, —$CH_2$—CH═N—O$CH_3$, and —CH═CH—N($CH_3$)—$CH_3$. Up to two heteroatoms may be consecutive, such as, for example, —$CH_2$—NH—O$CH_3$ and —$CH_2$—O—Si$(CH_3)_3$. Also included in the term "heteroalkyl" are those radicals described in more detail below as "heteroalkylene" and "heterocycloalkyl."

The term "cycloalkyl" by itself or in combination with other terms, represents, unless otherwise stated, cyclic version of "alkyl". Thus, the term "cycloalkyl" is meant to be included in the terms "alkyl". Examples of cycloalkyl include cyclopentyl, cyclohexyl, 1-cyclohexenyl, 3-cyclohexenyl, cycloheptyl, cyclobutylene, cyclohexylene and the like.

The terms "heterocycloalkyl" and "heterocycloalkylene" as used herein, refer to cyclic versions of heteroalkyl and heteroalkylene as described above. Examples of heterocycloalkyl include pyrrolidinyl, tetrahydrofuranyl, dioxolanyl, imidazolinyl, pyrazolidinyl, piperidinyl, morpholinyl, dithianyl, thiomorpholinyl, piperainyl, and trithianyl. Examples of heterocycloalkenyl include pyrrolinyl imidazolinyl, and 2H-pyranyl.

The term "aryl" as used herein refers to a 6- to 14-membered monocyclic, bicyclic or tricyclic aromatic hydrocarbon ring system. Examples of an aryl group include phenyl and naphthyl.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl and oxazolyl. A heteroaryl group can be unsubstituted or optionally substituted with one or more substituents as described herein below.

The terms "arylalkyl" and "heteroarylalkyl" are meant to include those radicals in which an aryl or heteroaryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like). "Heteroarylalkyl" is meant to include those radicals in which a heteroaryl group is attached to an alkyl group.

The term "heterocycle", "heterocyclic residue" or "heterocyclyl" as used herein refer to 3- to 14-membered ring systems which are either saturated, unsaturated, or aromatic, and which contain from 1 to 4 heteroatoms independently selected from nitrogen, oxygen and sulfur, and wherein the nitrogen and sulfur heteroatoms may be optionally oxidized, and the nitrogen heteroatom may be optionally quaternized, including monocyclic, bicyclic, and tricyclic ring systems. The bicyclic and tricyclic ring systems may encompass a heterocycle or heteroaryl fused to a benzene ring. The heterocycle may be attached via any heteroatom or carbon atom. Heterocycles include heteroaryls, heterocycloalkyls, and heterocycloalkenyls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl. A heterocycle group can be unsubstituted or optionally substituted with one or more substituents as described herein below.

The term "alkoxy" as used herein refers to a —O-alkyl group. For example, an alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl. The term "alkoxyalkyl" refers to an alkoxy group appended to an alkyl radical. The term "aryloxy" as used herein refers to a —O-aryl group. The term "alkoxyaryl" refers to an alkoxy group attached to an aryl radical.

The term "amino" refers to a chemical functionality —NR'R", wherein R' and R' are independently hydrogen, alkyl or aryl.

The term "aminoalkyl," as used herein, refers to an alkyl group (typically one to eight carbon atoms) wherein one or more of the $C_1$-$C_8$ alkyl group's hydrogen atoms are replaced with an amine. Examples of aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2CH_2N(CH_3)_2$, t-butylaminomethyl, isopropylaminomethyl and the like. The term "alkylamino" refers to an amino group wherein one or more hydrogen atoms are replaced with an alkyl group. Similarly, the term "dialkylamino" refers to an amino group having two attached alkyl groups that can be the same or different.

The term "halo" or "halogen" as used herein refers to —F, —Cl, —Br or —I.

The term "haloalkyl," as used herein, refers to a $C_1$-$C_6$ alkyl group wherein one or more of the $C_1$-$C_6$ alkyl group's hydrogen atoms is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1- trifluoro-2-bromo-2-chloroethyl. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

The term "sulfonyl", whether used alone or linked to other terms such as alkylsulfonyl, denotes respectively divalent radicals —$SO_2$—.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C═O)—.

The term "aminocarbonyl" denotes an amide group of the formula —C(═O)$NH_2$.

The term "protected" with respect to hydroxyl groups, amine groups, carboxyl groups and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

The compounds of the invention can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of the compounds of the invention, including tautomeric forms of the compound.

Certain compounds of the invention may have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, and mixtures thereof, including a racemic mixture. Optical isomers of the smoothened receptor modulators can be obtained by known techniques such as asymmetric synthesis, chiral chromatography, simulated moving bed technology or via chemical separation of stereoisomers through the employment of optically active resolving agents.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

A "pharmaceutically acceptable" denotes any salt or ester of a compound of this invention, or any other compound which upon administration to a patient is capable of providing (directly or indirectly) a compound of this invention, or a metabolite or residue thereof.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al. (1977) J. Pharm. Sci. 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment.

For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester, but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). Radiolabeled compounds are useful as therapeutic or prophylactic agents, e.g., cancer therapeutic agents, research reagents, e.g., assay reagents, and diagnostic agents, e.g., in vivo imaging agents. All isotopic variations of the compounds of the invention, whether radioactive or not, are intended to be encompassed within the scope of the invention.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

II. Compounds that Modulate Smoothened Receptor and Pharmaceutical Compositions Comprising them, Administration and Dosage The present invention relates to compounds useful in treating cancer and angiogenesis as defined by Formula I

I

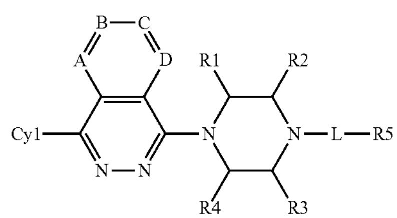

or a pharmaceutically acceptable salt thereof, wherein

A, B, C, and D are independently selected from CH or N, provided that at least one but no more than two of A, B, C, and D is N, $Cy^1$ is phenyl optionally substituted independently with 1-5 substituents, wherein the substituents are selected from the group consisting of $C_{1-8}$alkyl, $C_{1-8}$alkenyl, $C_{1-8}$alkynyl, $C_{1-6}$haloalkyl, halogen, cyano, hydroxy, oxo, —$OR^c$, —$NR^aR^b$, $NR^aC(=O)R^b$, —$C(=O)OR^c$, —$R^cOC(=O)NR^aR^b$, —$R^cOH$, —$C(=O)NR^aR^b$, —$OC(=O)NR^aR^b$, —$OC(=O)R^c$, —$NR^aC(=O)R^c$, —$R^bN(R^a)C(=O)R^c$, —$R^bN(R^a)C(=O)OR^c$, —$NR^aS(=O)_mR^c$, —$S(=O)_mNR^aR^b$, and $S(=O)_mR^c$;

$R^1$, $R^2$, $R^3$, and $R^4$ are each independently selected from H, $C_{1-6}$alkyl, $C_{1-6}$cycloalkyl, $C_{1-6}$haloalkyl, oxo, —$C(=O)OR^a$, —$R^cOH$, —$OR^c$, —$NR^aR^b$, $NR^aC(=O)R^b$, —$C(=O)OR^c$, —$C(=O)NR^aR^b$, —$OC(=O)R^c$, —$NR^aC(=O)R^c$, —$NR^aS(=O)_mR^c$, —$S(=O)_mNR^aR^b$, and $S(=O)_mR^c$, provided that at least one of $R^1$, $R^2$, $R^3$, and $R^4$ is not H;

$R^a$, $R^b$, and $R^c$ are each independently selected from H, $C_{1-8}$alkyl, $C_{1-8}$alkenyl, $C_{1-8}$alkynyl, $C_{1-6}$haloalkyl, heterocyclyl, aryl, and heteroaryl;

m is 1 or 2;

L is —$C(=O)$— or —$S(=O)_m$—;

$R^5$ is —$NR^aR^b$ or $Cy^2$;

$Cy^2$ is a partially or fully saturated or unsaturated 6-membered monocyclic ring formed of carbon atoms optionally including 1-3 heteroatoms, wherein the ring is optionally substituted independently with 1-5 substituents, wherein the substituents are independently selected from the group consisting of $C_{1-8}$alkyl, $C_{1-8}$alkenyl, $C_{1-8}$alkynyl, $C_{1-6}$haloalkyl, halogen, cyano, hydroxy, oxo, —$C(=O)OR^c$, —$R^cOH$, —$OR^c$, —$NR^aR^b$, $NR^aC(=O)R^b$, —$C(=O)NR^aR^b$, —$OC(=O)R^c$, —$NR^aC(=O)R^c$, —$NR^aS(=O)_mR^c$, —$S(=O)_mNR^aR^b$, and $S(=O)_mR^c$.

In one aspect, the invention provides the compounds represented by Formula II or pharmaceutically salts thereof.

II

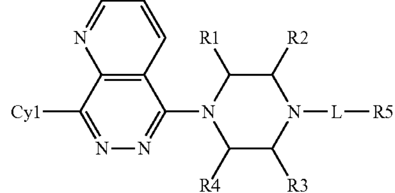

In another aspect, the invention provides the compounds represented by Formula III or pharmaceutically salts thereof.

III

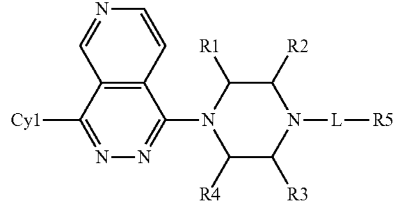

In another aspect, the invention provides the compounds represented by Formula IV or pharmaceutically salts thereof.

IV

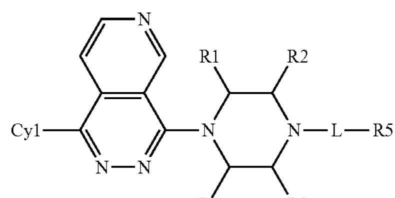

In another aspect, the invention provides the compounds represented by Formula V or pharmaceutically salts thereof.

V

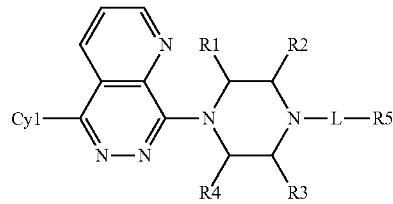

The invention further provides compounds of Formula I or pharmaceutically acceptable salt thereof, wherein $Cy^1$ is unsubstituted phenyl. In one aspect, $Cy^1$ can be phenyl substituted independently with 1-5 substituents, wherein the substituents are selected from the group consisting of $C_{1-8}$alkyl, $C_{1-6}$haloalkyl, halogen, cyano, —$OR^c$, —$NR^aR^b$, $NR^aC$(=O)$R^b$, —C(=O)$OR^c$, —$R^cOC$(=O)$NR^aR^b$, —$R^cOH$, —C(=O)$NR^aR^b$, —OC(=O)$NR^aR^b$, —OC(=O)$R^c$, —$NR^aC$(=O)$R^c$, —$R^bN(R^a)C$(=O)$R^c$, and —$R^bN(R^a)C$(=O)$OR^c$.

The invention further provides compounds of Formula I or pharmaceutically acceptable salt thereof, wherein $R^1$, $R^2$, $R^3$, and $R^4$ can be each independently selected from H, $C_{1-6}$alkyl and $C_{1-6}$haloalkyl, provided that at least one of $R^1$, $R^2$, $R^3$, and $R^4$ is not H. In one aspect, $R^1$, $R^2$, $R^3$ can be each H, and $R^4$ is $C_{1-6}$alkyl. $R^4$ can be, for example, methyl. In another aspect, $R^1$ and $R^3$ can be each H, and $R^2$ and $R^4$ can be each independently $C_{1-6}$alkyl. Each $R^2$ and $R^4$ can be, independently, methyl. In a further aspect, $R^1$, $R^3$, and $R^4$ can be each H, and $R^2$ can be $C_{1-6}$alkyl. In another aspect, $R^1$, $R^2$, and $R^4$ can be each H, and $R^3$ can be $C_{1-6}$alkyl. In a further aspect, $R^2$, $R^3$, and $R^4$ can be each H, and $R^1$ can be $C_{1-6}$alkyl. In another aspect, $R^1$ and $R^3$ can be each independently $C_{1-6}$alkyl, and $R^2$ and $R^4$ can be each H.

The invention provides compounds of Formula I or pharmaceutically acceptable salts thereof, wherein L is —C(=O)—. In another aspect, L can be —S(=O)$_2$— or —S(=O)—.

The invention further provides compounds of Formula I or pharmaceutically acceptable salt thereof, wherein $R^5$ is $Cy^2$. In one aspect, $Cy^2$ can be phenyl optionally substituted independently with 1-5 substituents, wherein the substituents are selected from the group consisting of $C_{1-8}$alkyl, $C_{1-8}$alkenyl, $C_{1-8}$alkynyl, $C_{1-6}$haloalkyl, halogen, cyano, hydroxy, oxo, —C(=O)$OR^c$, —$R^cOH$, —$OR^c$, —$NR^aR^b$, $NR^aC$(=O)$R^b$, —C(=O)$NR^aR^b$, —OC(=O)$R^c$, —$NR^aC$(=O)$R^c$, —$NR^aS$(=O)$_mR^c$, —S(=O)$_mNR^aR^b$, and S(=O)$_mR^c$. In a further aspect, $Cy^2$ can be phenyl substituted independently with 1-5 substituents, wherein the substituents are selected from the group consisting of $C_{1-8}$alkyl, $C_{1-6}$haloalkyl, halogen, cyano, hydroxy and —$OR^c$. In another aspect, $Cy^2$ can be unsubstituted phenyl. In an alternative aspect, $Cy^2$ can be cyclohexyl optionally substituted independently with 1-5 substituents, wherein the substituents are selected from the group consisting of $C_{1-8}$alkyl, $C_{1-8}$alkenyl, $C_{1-8}$alkynyl, $C_{1-6}$haloalkyl, halogen, cyano, hydroxy, oxo, —C(=O)$OR^c$, —$R^cOH$, —$OR^c$, —$NR^aR^b$, $NR^aC$(=O)$R^b$, —C(=O)$NR^aR^b$, —OC(=O)$R^c$, —$NR^aC$(=O)$R^c$, —$NR^aS$(=O)$_mR^c$, —S(=O)$_mNR^aR^b$, and S(=O)$_mR^c$. The substituents in this case can be selected from the group consisting of $C_{1-8}$alkyl, $C_{1-6}$haloalkyl, halogen, cyano, and hydroxy. In a further aspect, $Cy^2$ can be piperidyl optionally substituted independently with 1-5 substituents, wherein the substituents are selected from the group consisting of $C_{1-8}$alkyl, $C_{1-8}$alkenyl, $C_{1-8}$alkynyl, $C_{1-6}$haloalkyl, halogen, cyano, hydroxy, oxo, —C(=O)$OR^c$, —$R^cOH$, —$OR^c$, —$NR^aR^b$, $NR^aC$(=O)$R^b$, —C(=O)$NR^aR^b$, —OC(=O)$R^c$, —$NR^aC$(=O)$R^c$, —$NR^aS$(=O)$_mR^c$, —S(=O)$_mNR^aR^b$, and S(=O)$_mR^c$. In an alternative aspect, piperidyl can be unsubstituted. In a further aspect, $Cy^2$ can be morpholinyl optionally substituted independently with 1-5 substituents, wherein the substituents are selected from the group consisting of $C_{1-8}$alkyl, $C_{1-8}$alkenyl, $C_{1-8}$alkynyl, $C_{1-6}$haloalkyl, halogen, cyano, hydroxy, oxo, —C(=O)$OR^c$, —$R^cOH$, —$OR^c$, —$NR^aR^b$, $NR^aC$(=O)$R^b$, —C(=O)$NR^aR^b$, —OC(=O)$R^c$, —$NR^aC$(=O)$R^c$, —$NR^aS$(=O)$_mR^c$, —S(=O)$_mNR^aR^b$, and S(=O)$_mR^c$. In another aspect, $Cy^2$ can be tetrahydro-2H-pyranyl optionally substituted independently with 1-5 substituents, wherein the substituents are selected from the group consisting of $C_{1-8}$alkyl, $C_{1-8}$alkenyl, $C_{1-8}$alkynyl, $C_{1-6}$haloalkyl, halogen, cyano, hydroxy, oxo, —C(=O)$OR^c$, —$R^cOH$, —$OR^c$, —$NR^aR^b$, $NR^aC$(=O)$R^b$, —C(=O)$NR^aR^b$, —OC(=O)$R^c$, —$NR^aC$(=O)$R^c$, —$NR^aS$(=O)$_mR^c$, —S(=O)$_mNR^aR^b$, and S(=O)$_mR^c$.

The invention further provides compounds of Formula I, wherein compounds are selected from the list consisting of:

(S)-(2-methyl-4-(1-phenylpyrido[3,4-d]pyridazin-4-yl)piperazin-1-yl)(phenyl)methanone, (S)-(2-methyl-4-(1-(4-(trifluoromethyl)phenyl)pyrido[3,4-d]pyridazin-4-yl)piperazin-1-yl)(phenyl)methanone, (S)-(2-methyl-4-(1-(4-(trifluoromethyl)phenyl)pyrido[3,4-d]pyridazin-4-yl)piperazin-1-yl)(piperidin-1-yl)methanone, (S)-(4-(1-(4-(hydroxymethyl)phenyl)pyrido[3,4-d]pyridazin-4-yl)-2-methylpiperazin-1-yl)(piperidin-1-yl)methanone, (S)-(4-(4-(3-methyl-4-(piperidine-1-carbonyl)piperazin-1-yl)pyrido[3,4-d]pyridazin-1-yl)phenyl)methyl carbamate, ((R)-4-(1-(4-chloro-2-fluorophenyl)pyrido[3,4-d]pyridazin-4-yl)-3-methylpiperazin-1-yl)(phenyl)methanone, (R)-(4,4-difluorocyclohexyl)(3-methyl-4-(1-phenylpyrido[3,4-d]pyridazin-4-yl)piperazin-1-yl)methanone, (R)-cyclohexyl(3-methyl-4-(1-phenylpyrido[3,4-d]pyridazin-4-yl)piperazin-1-yl)methanone, ((R)-4-(1-(4-chloro-2-fluorophenyl)pyrido[3,4-d]pyridazin-4-yl)-3-methylpiperazin-1-yl)(cyclohexyl)methanone, (R)-(3-methyl-4-(1-(4-(trifluoromethyl)phenyl)pyrido[3,4-d]pyridazin-4-yl)piperazin-1-yl)(phenyl)methanone, (R)-(3-methyl-4-(1-phenylpyrido[3,4-d]pyridazin-4-yl)piperazin-1-yl)(phenyl)methanone, ((1S,4S)-4-hydroxycyclohexyl)((R)-3-methyl-4-(1-phenylpyrido[3,4-d]pyridazin-4-yl)piperazin-1-yl)methanone, ((1R,4R)-4-hydroxycyclohexyl)((R)-3-methyl-4-(1-phenylpyrido[3,4-d]pyridazin-4-yl)piperazin-1-yl)methanone, (R)-(3-methyl-4-(4-phenylpyrido[4,3-d]pyridazin-1-yl)piperazin-1-yl)(phenyl)methanone, (R)-(3-methyl-4-(1-phenylpyrido[4,3-d]pyridazin-4-yl)piperazin-1-yl)(tetrahydro-2H-pyran-4-yl)methanone, (S)-(3-methyl-4-(1-phenylpyrido[3,4-d]pyridazin-4-yl)piperazin-1-yl)(phenyl)methanone, (S)-(4,4-difluorocyclohexyl)(3-methyl-4-(1-phenylpyrido[3,4-d]pyridazin-4-yl)piperazin-1-yl)methanone, (R)-(3-methyl-4-(1-phenylpyrido[3,4-d]pyridazin-4-yl)piperazin-1-yl)(morpholino)methanone, (R)—N,3-dimethyl-N-phenyl-4-(1-phenylpyrido[3,4-d]pyridazin-4-yl)piperazine-1-carboxamide, (R)-(3-methyl-4-(1-phenylpyrido[3,4-d]pyridazin-4-yl)piperazin-1-yl)(piperidin-1-yl)methanone, (R)—N,N,3-trimethyl-4-(1-phenylpyrido[3,4-d]pyridazin-4-yl)piperazine-1-carboxamide, (R)-(4,4-difluoropiperidin-1-yl)(3-methyl-4-(1-phenylpyrido[3,4-d]pyridazin-4-yl)piperazin-1-yl)methanone, (4,4-difluorocyclohexyl)((2S,5R)-2,5-dimethyl-4-(1-phenylpyrido[3,4-d]pyridazin-4-yl)piperazin-1-yl)methanone, (4,4-difluorocyclohexyl)((2R,5S)-2,5-dimethyl-4-(1-phenylpyrido[3,4-d]pyridazin-4-yl)piperazin-1-yl)methanone, (S)-(4,4-difluoropiperidin-1-yl)(2-methyl-4-(1-(4-(trifluoromethyl)phenyl)pyrido[3,4-d]pyridazin-4-yl)piperazin-1-yl)methanone, (S)-methyl (4-(4-(4-(4,4-difluorocyclohexanecarbonyl)-3-methylpiperazin-1-yl)pyrido[3,4-d]pyridazin-1-yl)phenyl)methylcarbamate, (S)—N-((4-(4-(4-(4,4-difluorocyclohexanecarbonyl)-3-methylpiperazin-1-yl)pyrido[3,4-d]pyridazin-1-yl)phenyl)methyl)acetamide, (S)-(4-(4-(4-(4,4-difluorocyclohexanecarbonyl)-3-methylpiperazin-1-yl)pyrido[3,4-d]pyridazin-1-yl)phenyl)methyl carbamate, (R)-(4,4-difluorocyclohexyl)(3-methyl-4-(1-(4-(trifluoromethyl)phenyl)pyrido[3,4-d]pyridazin-4-yl)piperazin-1-yl)methanone, (R)-(3-methyl-4-(1-(4-(trifluoromethoxy)phenyl)pyrido[3,4-d]pyridazin-4-yl)piperazin-1-yl)(phenyl)methanone, (R)-4-(4-(4-(4,4-difluorocyclohexanecarbonyl)-2-methylpiperazin-1-yl)pyrido[3,4-d]pyridazin-1-yl)benzonitrile, (R)-4-(4-(4-benzoyl-2-methylpiperazin-1-yl)pyrido[3,4-d]pyridazin-1-yl)benzonitrile, (R)-4-(4-(4-benzoyl-2-methylpiperazin-1-yl)pyrido[3,4-d]pyridazin-1-yl)benzamide, (R)-(4-(1-(4-fluorophenyl)pyrido[3,4-d]pyridazin-4-yl)-3-methylpiperazin-1-yl)(phenyl)methanone, (R)-(4-(1-(4-(hydroxymethyl)phenyl)pyrido[3,4-d]pyridazin-4-yl)-3-methylpiperazin-1-yl)(phenyl)methanone, (S)-(2-methyl-4-(5-phenylpyrido[2,3-d]pyridazin-8-yl)piperazin-1-yl)(phenyl)methanone, (R)-(3-methyl-4-(5-phenylpyrido[2,3-d]pyridazin-8-yl)piperazin-1-yl)(phenyl)methanone, (R)-(3-methyl-4-(8-phenylpyrido[3,2-d]pyridazin-5-yl)piperazin-1-yl)(phenyl)methanone, (R)-(4-(5-(4-(hydroxymethyl)phenyl)pyrido[2,3-d]pyridazin-8-yl)-3-methylpiperazin-1-yl)(phenyl)methanone, ((R)-4-(5-(4-chloro-2-fluorophenyl)pyrido[2,3-d]pyridazin-8-yl)-3-methylpiperazin-1-yl)(phenyl)methanone, (R)-(3-methyl-4-(5-(4-(trifluoromethyl)phenyl)pyrido[2,3-d]pyridazin-8-yl)piperazin-1-yl)(phenyl)methanone, (R)-4-(8-(4-benzoyl-2-methylpiperazin-1-yl)pyrido[2,3-d]pyridazin-5-yl)benzonitrile, and (R)-(3-methyl-4-(8-(4-(trifluoromethyl)phenyl)pyrido[3,2-d]pyridazin-5-yl)piperazin-1-yl)(phenyl)methanone, or pharmaceutically acceptable salts thereof.

A. Preparation of Compounds

The present invention comprises processes for the preparation of compounds of Formula I.

Methods A-D below provide exemplary synthetic schemes for the preparation of the compounds of the present invention. One of skill in the art will understand that additional methods are also useful. In other words, the compounds of the invention can be made using organic synthesis using starting materials, reagents and reactions well known in the art.

Certain compounds of the invention may be conveniently prepared by a general process outlined in Method A.

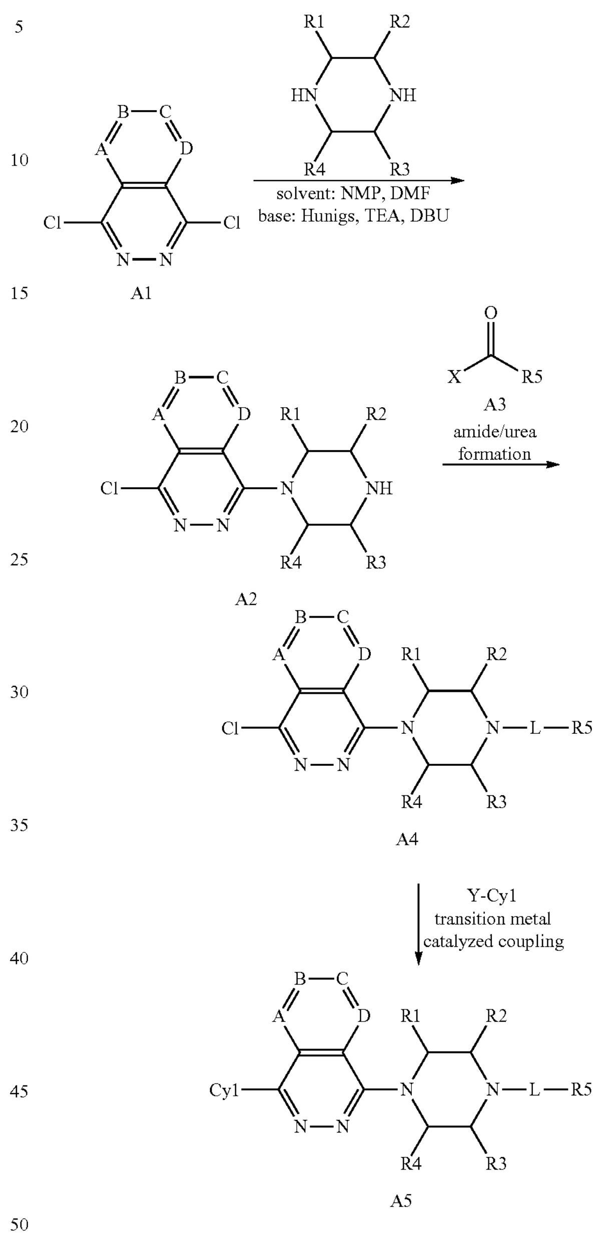

Method A: The dichloro-heterocycle A1 may be directly substituted with an appropriately substituted or unsubstituted piperazine in the presence or absence of base (inorganic or organic) and the presence or absence of solvent (DMF, NMP, etc) to obtain, following separation, both possible regioisomers A2. The product A2 may be transformed to L linked compounds using the reagent A3 where X may be chosen from an appropriate group such as OH, Cl, or from any group capable of activating a carbonyl group by an amine (imidazole, p-nitrophenol, etc.) to effectively form an amide or urea (A4). The coupling to produce A4 may be assisted by the use of organic or inorganic bases, activating agents such as EDC/HOAT, and catalysts such as DMAP or HOBT, etc. Installation of the $Cy^1$ group may be accomplished by transition metal catalyzed carbon-carbon or carbon-nitrogen bond forming transformations known to the art such as Suzuki arylations, Stille couplings, Negishi couplings, Buchwald aminations, etc. to obtain A5.

Certain compounds of the invention may be conveniently prepared by a general process outlined in Method B.

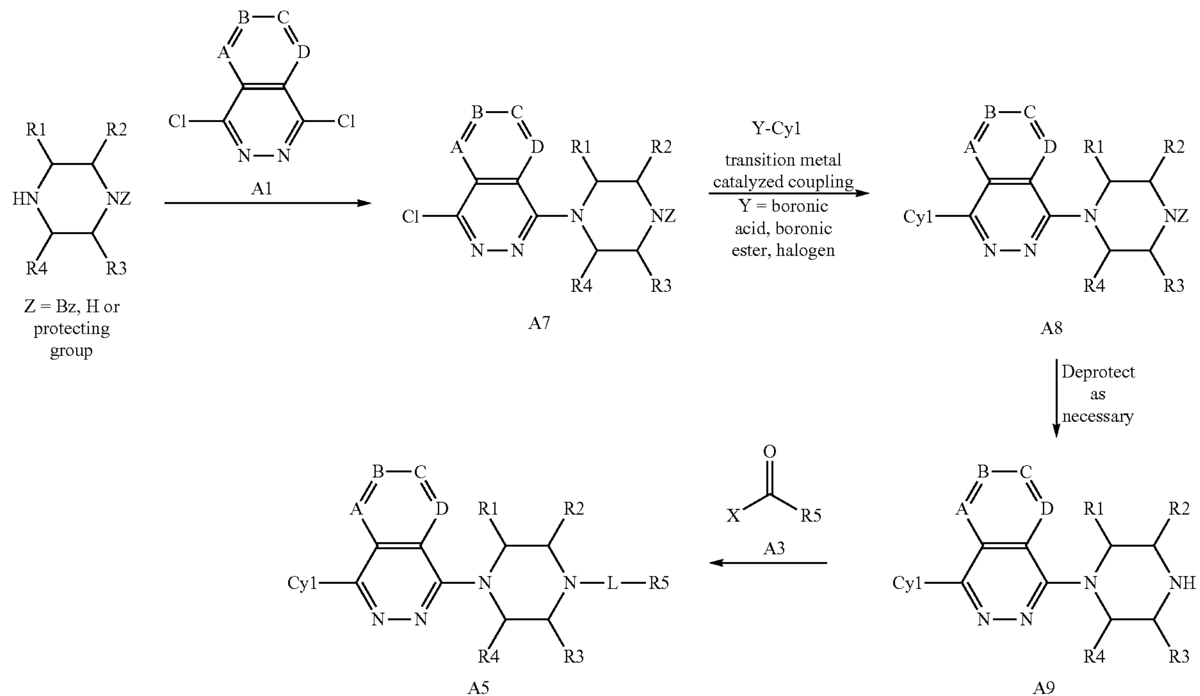

Method B: The dichloro-heterocycle A1 may be directly substituted in the presence or absence of base and the presence or absence of solvent with an appropriately substituted or unsubstituted, protected or unprotected at one of the two nitrogens, benzoylated or un-benzoylated at one of the two nitrogens piperazine A6 to obtain, following separation, both possible regioisomers A7. Installation of the $Cy^1$ group may be accomplished by transition metal catalyzed carbon-carbon or carbon-nitrogen bond forming transformations known to the art such as Suzuki arylations, Stille couplings, Negishi couplings, Buchwald aminations, etc. to obtain A8. The product A8 may be deprotected as appropriate (i.e., if Z=Boc, TFA in dichloromethane may be used, etc.) to obtain A9 which may then be transformed to the L linked compounds using the reagent A3 where X may be chosen from an appropriate group such as OH, Cl, or from any group capable of activating a carbonyl group by an amine (imidazole, p-nitrophenol, etc.) to effectively form an amide or urea (A5). The coupling to produce A5 may be assisted by the use of organic or inorganic bases, activating agents such as EDC/HOAT, and catalysts such as DMAP or HOBT, etc. In the event that Z=benzoyl, A5 is obtained directly from A7.

Certain compounds of the invention may be prepared by a general process outlined in Method C.

-continued

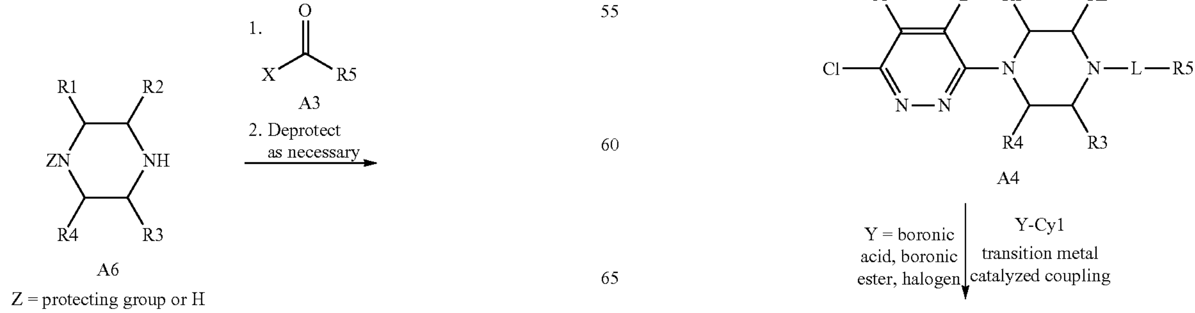

-continued

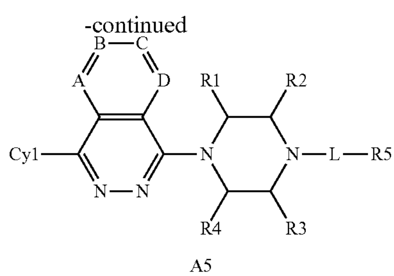

Method C: Intermediate A6 may alternatively be transformed to the L-linked compounds using the reagent A3 where X may be chosen from an appropriate group such as OH, Cl, or from any group capable of activating a carbonyl group by an amine (imidazole, p-nitrophenol, etc.) to effectively form an amide or urea. The coupling may be assisted by the use of organic or inorganic bases, activating agents such as EDC/HOAT, and catalysts such as DMAP or HOBT, etc. In examples where Z=H, A10 is directly obtained. In examples where Z=protecting group, standard methods for removal of the protecting group are applied to obtain A10 (i.e., if Z=Boc, TFA in dichloromethane may be used, etc.). The dichloroheterocycle A1 may be directly substituted in the presence or absence of base and the presence or absence of solvent (DMF, NMP, etc) with an appropriately substituted or unsubstituted piperazine to obtain, following separation, both possible regioisomers A4. Installation of the $Cy^1$ group may be accomplished by transition metal catalyzed carbon-carbon or carbon-nitrogen bond forming transformations known to the art such as Suzuki arylations, Stille couplings, Negishi couplings, Buchwald aminations, etc. to obtain A5.

Certain compounds of the invention may be conveniently prepared by a general process outlined in Method D.

Method D: Intermediate A11 may be cyclized to A12 by refluxing with hydrazine or hydrazine hydrate with or without solvent (water, various alcohols, mixtures thereof, etc.). Refluxing A12 with phosphorus oxychloride in the presence of an organic base (i.e. Hünig's base, triethylamine, pyridine, etc) produces A13 as a substrate for nucleophilic addition by excess A6 to obtain A8. In examples where Z=protecting group, standard methods for removal of the protecting group are applied to obtain A9 (i.e., if Z=Boc, TFA in dichloromethane may be used, etc.) can be used. Intermediate A9 may then be transformed to L linked compounds using the reagent A3 where X may be chosen from an appropriate group such as OH, Cl, or from any group capable of activating a carbonyl group by an amine (imidazole, p-nitrophenol, etc.) to effectively form an amide or urea (A5). The coupling to produce A5 may be assisted by the use of organic or inorganic bases, activating agents such as EDC/HOAT, and catalysts such as DMAP or HOBT, etc.

B. Pharmaceutical Compositions and Administration

Compounds useful in the present invention can be used in the form of pharmaceutically acceptable salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, mandelate, methanesulfonate, nicotinate, 2-naphthalenesulfonate, oxalate, palmoate, pectinate, persulfate, 2-phenylpropionate, picrate, pivalate, propionate, salicylate, succinate, sulfate, tartrate, thiocyanate, tosylate, mesylate, and undecanoate. When compounds of the invention include an

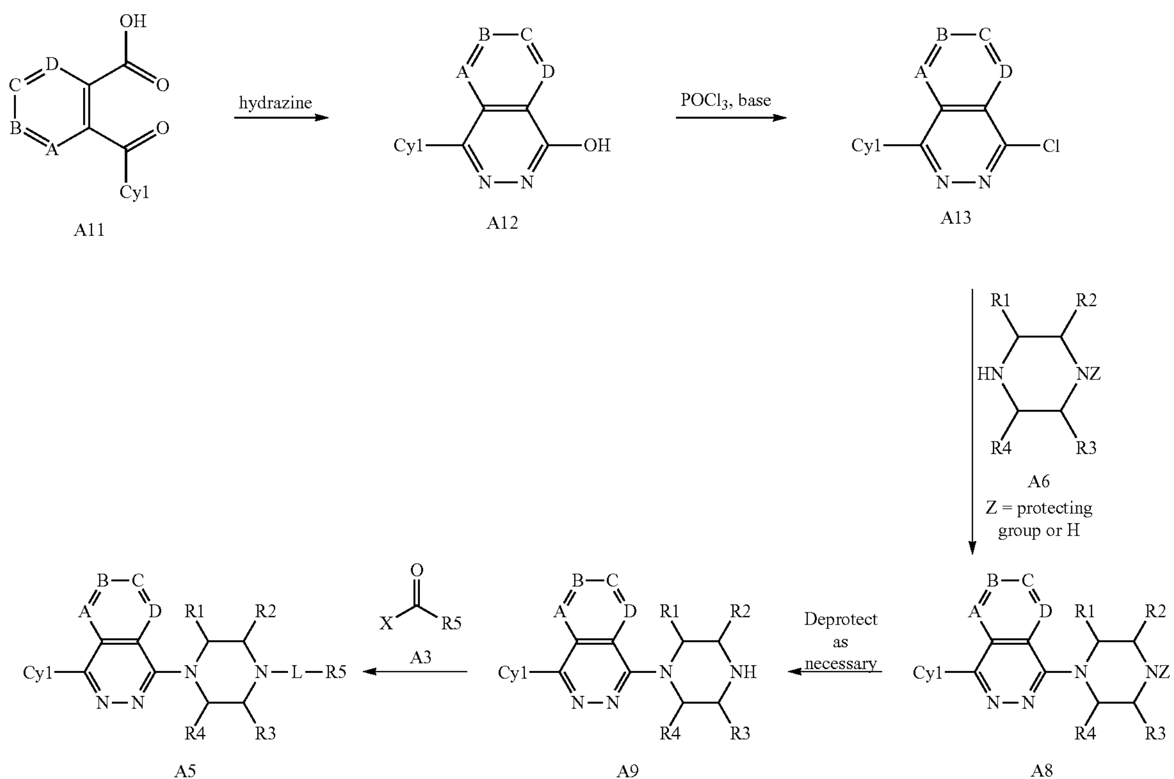

acidic function such as a carboxy group, then suitable pharmaceutically acceptable salts for the carboxy group are well known to those skilled in the art and include, for example, alkaline, alkaline earth, ammonium, quaternary ammonium cations and the like. For additional examples of "pharmacologically acceptable salts," see infra and Berge et al. *J. Pharm. Sci.* 66: 1, 1977. In certain embodiments of the invention salts of hydrochloride and salts of methanesulfonic acid can be used.

For administration, the compounds useful in this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds useful in this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

The therapeutically effective amount of the smoothed receptor modulator in the compositions useful in the invention can range from about 0.1 mg to about 180 mg, for example from about 5 mg to about 180 mg, or from about 1 mg to about 100 mg of the smoothened antagonist per subject. In some aspects, the therapeutically effective amount of the compound in the composition can be chosen from about 0.1 mg, about 1 mg, 5 mg, about 15 mg, about 20 mg, about 30 mg, about 50 mg, about 60 mg, about 75 mg, about 90 mg, about 120 mg, about 150 mg, about 180 mg.

While it may be possible to administer a compound of the invention to a subject alone, the compound administered will normally be present as an active ingredient in a pharmaceutical composition. Thus, a pharmaceutical composition of the invention may comprise a therapeutically effective amount of at least one smoothed receptor modulator compound, or an effective dosage amount of at least one smoothed receptor modulator compound.

As used herein, an "effective dosage amount" is an amount that provides a therapeutically effective amount of the smoothened antagonist when provided as a single dose, in multiple doses, or as a partial dose. Thus, an effective dosage amount of the smoothened antagonist of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the smoothed receptor modulator compound is administered by administering a portion of the composition.

Alternatively, a pharmaceutical composition in which two or more unit dosages, such as in tablets, capsules and the like, are required to administer an effective amount of the smoothed receptor modulator may be administered in less than an effective amount for one or more periods of time (e.g., a once-a-day administration, and a twice-a-day administration), for example to ascertain the effective dose for an individual subject, to desensitize an individual subject to potential side effects, to permit effective dosing readjustment or depletion of one or more other therapeutics administered to an individual subject, and/or the like.

The effective dosage amount of the pharmaceutical composition useful in the invention can range from about 1 mg to about 360 mg from a unit dosage form, for example about 5 mg, about 15 mg, about 30 mg, about 50 mg, about 60 mg, about 75 mg, about 90 mg, about 120 mg, about 150 mg, about 180 mg, about 210 mg, about 240 mg, about 300 mg, or about 360 mg from a unit dosage form.

III. Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "combination-therapy", in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents, which may be used in combination with compounds of the present invention, consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents, which may be used in combination with compounds of the present invention, consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-11707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzamab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 ocreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), VECTIBIX™ (panitumumab), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM disintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sima, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors and CDK inhibitors, TNF inhibitors, metallomatrix proteases inhibitors (MMP), COX-2 inhibitors including celecoxib, NSAID's, or $\alpha_v\beta_3$ inhibitors.

IV. Therapeutic Uses of the Compounds of the Invention

Compounds and compositions of the present application may thus be used, in one aspect, for the treatment or prevention of angiogenesis related diseases. "Angiogenesis" refers to any alteration of an existing vascular bed or the formation of new vasculature, which benefits tissue perfasion. This includes the formation of new vessels by sprouting of endothelial cells from existing blood vessels or the remodelling of existing vessels to alter size, maturity, direction or flow properties to improve blood perfusion of tissue.

Hh is known to stimulate angiogenesis. It has been demonstrated that Matrigel plugs impregnated with hedgehog protein and inserted into mice evince substantial neovascularization, whereas Matrigel plugs not carrying hedgehog show comparatively little vascularization. Hedgehog protein is also capable of increasing vascularization of the normally avascular mouse cornea. The PTCH1 gene is expressed in normal vascular tissues, including the endothelial cells of the aorta, vascular smooth muscle cells, adventitial fibroblasts of the aorta, the coronary vasculature and cardiomyocytes of the atria and ventricles. These tissues are also sensitive to hedgehog protein. Treatment with exogenous hedgehog causes upregulation of PTCH1 expression. In addition, hedgehog proteins have been shown to stimulate proliferation of vascular smooth muscle cells in vivo. Hedgehog proteins also cause fibroblasts to increase expression of angiogenic growth factors such as VEGF, bFGF, Ang-1 and Ang-2. Lastly, hedgehog proteins are known to stimulate recovery from ischemic injury and stimulate formation of collateral vessels. Given that Hh promotes angiogenesis, antagonists of Hh pathway, such as SMO antagonists of the present invention are useful as angiogenesis inhibitors, particularly in situations where some level of hedgehog signaling is necessary for angiogenesis.

Angiogenesis is fundamental to many disorders. Persistent, unregulated angiogenesis occurs in a range of disease states, tumor metastases and abnormal growths by endothelial cells. The vasculature created as a result of angiogenic processes supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

The compounds and compositions of the current invention can be used to treat diseases supported by or associated with angiogenesis. These diseases include ocular neovascular disease, age-related macular degeneration, diabetic retinopathy, retinopathy of prematurity, corneal graft rejection, neovascular glaucoma, retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, corneal graph rejection, rheumatoid arthritis, osteoarthritis chronic inflammation (e.g., ulcerative colitis or Crohn's disease), hemangioma, Osler-Weber-Rendu disease, and hereditary hemorrhagic telangiectasia.

In addition, angiogenesis plays a critical role in cancer. A tumor cannot expand without a blood supply to provide nutrients and remove cellular wastes. Tumors in which angiogenesis is important include solid tumors such as rhabdomyosarcomas, retinoblastoma, Ewing sarcoma, neuroblastoma, and osteosarcoma, and benign tumors such as acoustic neuroma, neurofibroma, trachoma and pyogenic granulomas. Angiogenic factors have been found associated with several solid tumors. Prevention of angiogenesis could halt the growth of these tumors and the resultant damage to the animal due to the presence of the tumor. Angiogenesis is also associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

In addition to tumor growth, angiogenesis is important in metastasis. Initially, angiogenesis is important in the vascularization of the tumor which allows cancerous cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

It is further contemplated that the use of the smoothened antagonists of the present invention may be specifically targeted to disorders where the affected tissue and/or cells evince high Hh pathway activation. Expression of GLI genes is activated by the hedgehog signaling pathway, including GLI1, GLI2 and GLI3. GLI1 expression is most consistently correlated with hedgehog signaling activity across a wide range of tissues and disorders, while GLI3 is somewhat less so. The GLI genes encode transcription factors that activate expression of many genes needed to elicit the full effects of Hh signaling. However, the GLI3 transcription factor can also act as a repressor of hedgehog effector genes, and therefore, expression of GLI3 can cause a decreased effect of the hedgehog signaling pathway. Whether GLI3 acts as a transcriptional activator or repressor depends on post-translational events, and therefore it is expected that methods for detecting the activating form (versus the repressing form) of GLI3 protein would also be a reliable measure of hedgehog pathway activation. GLI2 gene expression is expected to provide a reliable marker for Hh pathway activation. The GLI1 gene is strongly expressed in a wide array of cancers, hyperplasias and immature lungs, and serves as a marker for the relative activation of the hedgehog pathway. In addition, tissues, such as immature lung, that have high GLI gene expression are strongly affected by hedgehog inhibitors. Accordingly, it is contemplated that the detection of GLI gene expression may be used as a powerful predictive tool to identify tissues and disorders that will particularly benefit from treatment with an antagonist of Hh pathway.

In one aspect, GLI1 expression levels can be detected, either by direct detection of the transcript or by detection of protein levels or activity. Transcripts may be detected using any of a wide range of techniques that depend primarily on hybridization of probes to the GLI1 transcripts or to cDNAs synthesized therefrom. Well-known techniques include Northern blotting, reverse-transcriptase PCR and microarray analysis of transcript levels. Methods for detecting GLI protein levels include Western blotting, immunoprecipitation, two-dimensional polyacrylamide gel electrophoresis (2D SDS-PAGE) (for example, compared against a standard wherein the position of the GLI proteins has been determined), and mass spectroscopy. Mass spectroscopy may be coupled with a series of purification steps to allow high-throughput identification of many different protein levels in a particular sample. Mass spectroscopy and 2D SDS-PAGE can also be used to identify post-transcriptional modifications to proteins including proteolytic events, ubiquitination, phosphorylation, lipid modification etc. GLI activity may also be assessed by analyzing binding to substrate DNA or in vitro transcriptional activation of target promoters. Gel shift assays, DNA footprinting assays and DNA-protein crosslinking assays are all methods that may be used to assess the presence of a protein capable of binding to GLI binding sites on DNA. (*J Mol Med* 1999; 77(6):459-68; *Cell* 2000 Feb. 18; 100(4): 423-34; *Development* 2000; 127(19):4293-4301).

In another aspect, GLI transcript levels are measured and diseased or disordered tissues showing abnormally high GLI levels are treated with a hedgehog antagonist. Premature lung issue, lung cancers (e.g., adenocarcinomas, broncho-alveolar adenocarcinomas, small cell carcinomas), breast cancers (e.g., inferior ductal carcinomas, inferior lobular carcinomas, tubular carcinomas), prostate cancers (e.g., adenocarcinomas), pancreatic adenocarcinomas, gastric cancers, and benign prostatic hyperplasias all show strongly elevated GLI1 expression levels in certain cases. Accordingly, GLI1 expression levels are a powerful diagnostic device to determine which of these tissues should be treated with a smoothened antagonist. In addition, there is substantial correlative evidence that cancers of urothelial cells (e.g., bladder cancer, other urogenital cancers) will also have elevated GLI1 levels in certain cases. For example, it is known that loss of heterozygosity on chromosome 9q22 is common in bladder cancers. The ptc-1 gene is located at this position and ptc-1 loss of function is probably a partial cause of hyperproliferation, as in many other cancer types. Accordingly, such cancers would also show high GLI expression and would be particularly amenable to treatment with a smoothened antagonist.

It is anticipated that any degree of GLI overexpression may be useful in determining that a smoothened antagonist will be an effective therapeutic. In one aspect, GLI should be expressed at a level at least twice as high as normal.

The compounds and compositions of the present invention can be used in the treatment of neoplastic or hyperplastic transformations such as may occur in the central nervous system. For instance, the smoothened antagonists can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas. In one aspect, the subject method can be used as part of a treatment regimen for malignant medulloblastoma and other primary CNS malignant neuroectodermal tumors.

In another aspect, the methods of the invention can be used as part of treatment program for medulloblastoma. These tumors are also referred to as primitive neuroectodermal tumor (PNET). Medulloblastoma, a primary brain tumor, is the most common brain tumor in children. It is a primitive neuroectodermal tumor arising in the posterior fossa. Medulloblastomas account for approximately 25% of all pediatric brain tumors. Histologically, they are small round cell tumors commonly arranged in true rosettes, but may display some differentiation to astrocytes, ependymal cells or neurons. They may arise in other areas of the brain including the pineal gland (pineoblastoma) and cerebrum. Those arising in the supratentorial region generally fare worse than their counterparts. Medulloblastoma/PNETs are known to recur anywhere in the CNS after resection, and can even metastasize to bone. Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other aspects, the smoothened antagonists of the invention can be used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. In 51 children reported with ependymomas, ¾ were histologically benign. Approximately ⅔ arose from the region of the 4th ventricle. One third presented in the supratentorial region. Age at presentation peaks between birth and 4 years. The median age is about 5 years. Because so many children with this disease are babies, they often require multimodal therapy.

It has been reported that Sonic hedgehog regulates lung mesenchymal cell proliferation in vivo. Accordingly, methods of the present invention can be used to regulate regeneration of lung tissue, e.g., in the treatment of emphysema. It has also been demonstrated that Sonic hedgehog is expressed in human lung squamous carcinoma and adenocarcinoma cells. Fujita et al. (1997) *Biochem Biophys Res Commun* 238: 658. The expression of Sonic hedgehog was also detected in the human lung squamous carcinoma tissues, but not in the normal lung tissue of the same patient. They also observed that Sonic hedgehog stimulates the incorporation of BrdU into the carcinoma cells and stimulates their cell growth, while anti-Shh-antibody inhibited their cell growth. These results suggest that Hh, and/or SMO is involved in the cell growth of such transformed lung tissue and therefore indicate that the smoothened antagonists of the invention can be used as part of a treatment of lung carcinoma and adenocarcinomas, and other proliferative disorders involving the lung epithelia.

BCC is the most common human cancer, accounting for about 70% of human skin cancers, and representing at least one third of all cancer diagnosed in the US each year. More than 99% of BCC cases arise sporadically in the population, with only 0.5% of cases arising in individuals with Gorlin's Syndrome (GS). BCC rarely metastasizes, but can be locally aggressive and recurrent. Inactivating mutations in PTCH1 occur most commonly in these tumors. A subset of BCC is driven via mutations in SMO, and these mutations activate the pathway by generating proteins with decreased sensitivity to PTCH1 suppression. In one aspect, the methods of the current invention can be used for treatment of BCC.

Hh pathway has been implicated in many other types of cancer, including pancreatic cancer, other tumors of the gastrointestinal (GI) tract and prostate cancer. Abnormal expression of SHH, PTCH1 and SMO has been shown early in the formation of human pancreatic tumors. Thayer, S. P. et al. (2003) *Nature* 425: 313-317. Several pancreatic cancer cell lines were found to be PTCH1 and SMO-positive and growth inhibited in vitro by cyclopamine, suggesting an active autocrine loop through which tumor cells both make and respond to Hh ligand. Furthermore, systemic treatment with cyclopamine slowed the growth of tumors formed by these cell lines when implanted into nude mice. Similar observations were made for pancreatic and other GI tumors. Berman, D. M. et al. (2003) *Nature* 425: 846-851. Similar data was provided for prostate cancer as well, including SHH overexpression in tumor biopsies, especially in higher Gleason grade tumors, and in vitro and in vivo inhibitory effects of cyclopamine on growth of prostate cancer cell lines. The Hh pathway was further implicated in prostate tumor metastasis, as the capacity of AT6.3 cells to metastasize to the lung was completely abrogated by cyclopamine, and AT2.1, a rarely metastasizing clone, could be induced to metastasize by overexpression of GLI1, in a cyclopamine-insensitive manner. Thus, the smoothened antagonists of the invention can be used for the treatment of pancreatic and prostatic cancers.

Many other tumors may, based on evidence such as involvement of the Hh pathway in these tumors, or detected expression of hedgehog or its receptor in these tissues during development, be affected by treatment with the subject compounds. Such tumors include, but are by no means limited to, tumors related to Gorlin's syndrome (e.g., medulloblastoma, meningioma, etc.), tumors evidenced in PTCH1 knock-out mice (e.g., hemangioma, rhabdomyosarcoma, etc.), tumors resulting from GLI1 amplification (e.g., glioblastoma, sarcoma, etc.), tumors connected with TRC8, a PTCH1 homolog (e.g., renal carcinoma, thyroid carcinoma, etc.), Ext-1-related tumors (e.g., bone cancer, etc.), Shh-induced tumors (e.g., lung cancer, chondrosarcomas, etc.), and other tumors (e.g., breast cancer, urogenital cancer (e.g., kidney, bladder, ureter, prostate, etc.), adrenal cancer, and gastrointestinal cancer (e.g., stomach, intestine, etc.).

Further, the pharmaceutical preparations of the invention can be used for the treatment of hyperplastic epidermal conditions, such as keratosis, as well as for the treatment of neoplastic epidermal conditions such as those characterized by a high proliferation rate for various skin cancers, as for example squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

The present invention, thus generally described, will be understood more readily by reference to the following examples, which are provided by way of illustration and are not intended to be limiting of the present invention. Compounds of the invention may be synthesized from simple starting molecules and commercially available materials as illustrated in the Examples. Various modifications of the invention in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence. The structure of the prepared compounds is verified by mass spectral data. For some compounds, ions having mass greater than M+H are reported. These ions generally represent dimers or trimers of the synthesized compound, and in some instances represent trifluoroacetate adducts generated from the mobile phase of the LC/MS. The trifluoroacetate adducts will have a weight of M+115.

EXAMPLE 1

Synthesis of (S)-(2-methyl-4-(1-phenylpyrido[3,4-d]pyridazin-4-yl)piperazin-1-yl)(phenyl)methanone

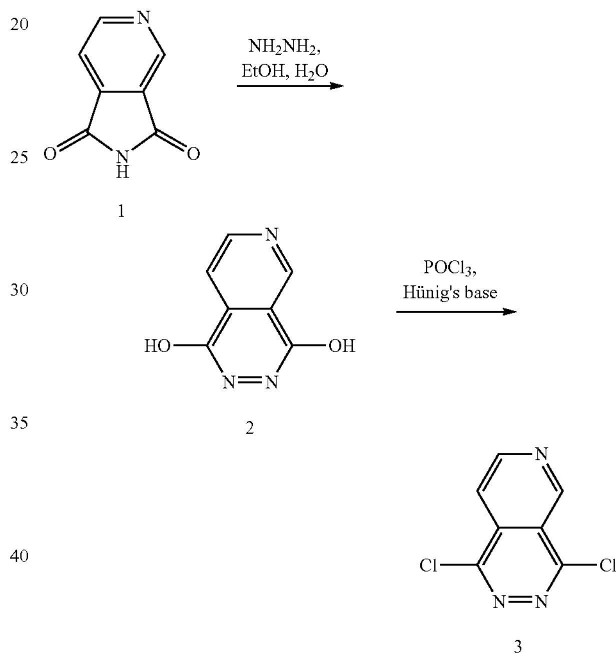

Step 1. To 2H-pyrrolo[3,4-c]pyridine-1,3-dione 1 (25.01 g, 169 mmol) dissolved in EtOH (250 mL) and $H_2O$ (250 mL) was added hydrazine hydrate (23 ml, 464 mmol). The solution was warmed to reflux and stirred for 1 h. After cooling to 40° C., the solution was brought to pH 4 with 5 N HCl whereupon precipitation of a light yellow solid occurred. After cooling to room temperature, the precipitate was filtered, washed with water, air dried for 2 h, and dried under high vacuum for 24 h at 40° C. to provide a quantitative yield of pyrido[3,4-d]pyridazine-1,4-diol 2. $^1H$ NMR (d6-DMSO) δ 11.67 (bs, 2H), 9.33 (s, 1H), 9.02 (d, J=5.5 Hz, 1H), 7.89 (d, J=5.5 Hz, 1H).

Step 2. 1,4-Dichloropyrido[3,4-d]pyridazine 3 was prepared from pyrido[3,4-d]pyridazine-1,4-diol 2 by two methods:

Method 1: A mixture of pyrido[3,4-d]pyridazine-1,4-diol 2 (24.2 g, 148 mmol) and $POCl_3$ (200 mL) was brought to reflux and stirred for 5 h. $POCl_3$ was removed by distillation and rotary evaporation at 60° C. The residue was taken up in ethyl acetate (700 mL) and stirred at 50° C. for 15 minutes and the suspension was filtered. The filtrate was concentrated in vacuo to yield 12 g of 1,4-dichloropyrido[3,4-d]pyridazine 3

(40% yield). $^{1}$H NMR ($CDCl_3$) δ 9.79 (s, 1H), 9.26 (d, J=5.5 Hz, 1H), 8.12 (d, J=5.5 Hz, 1H).

Method 2: Pyrido[3,4-d]pyridazine-1,4-diol 2 (5.00 g, 30.6 mmol) was suspended in phosphorus oxychloride (36.3 ml, 389 mmol) and Hünig's base (6.62 ml, 38.0 mmol). The reaction was stirred at reflux for 5 h and the $POCl_3$ was removed by rotary evaporation. The residue was suspended in $CH_2Cl_2$ (150 ml) and washed with ice/saturated $NaHCO_3$ (150 ml). Organics were sequestered and the aqueous phase was extracted further with $CH_2Cl_2$ (150 mL). Combined organics were dried with $MgSO_4$ and removed in vacuo. Recrystallization from hexane/ethyl acetate gave 4.9 g of yellow crystals. Residual Hünig's base was removed by dissolving the crystals in $CH_2Cl_2$ (200 mL), washing organics with saturated $NaHCO_3$ (150 mL), drying sequestered organics over $MgSO_4$ and removal of solvent. In this way 4.1 g of 1,4-dichloropyrido[3,4-d]pyridazine 3 were obtained.

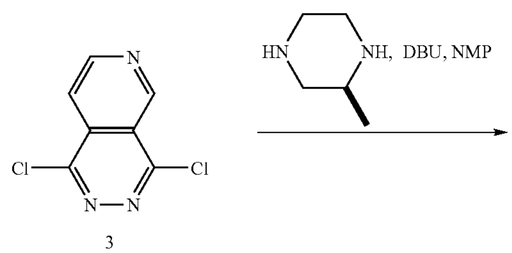

Step 3. To 1,4-dichloropyrido[3,4-d]pyridazine 3 (0.500 g, 2.50 mmol) in NMP (2.5 ml) was added (S)-2-methylpiperazine (0.300 g, 3.00 mmol). The reaction was stirred at 25° C. for 2 h. After one hour reaction contents were diluted with water (20×) and extracted with 10% MeOH in $CH_2Cl_2$ (3×25 mL). The combined organics were dried with $Na_2SO_4$ and concentrated in vacuo. Silica gel chromatography (gradient elution 0 to 5% MeOH in $CH_2Cl_2$) afforded (S)-1-chloro-4-(3-methylpiperazin-1-yl)pyrido[3,4-d]pyridazine 4 plus 10-15% substitution at the 4-position. $^{1}$H NMR ($CDCl_3$) δ 9.48 (s, 1H), 9.03 (d, J=5.5 Hz, 1H), 7.94 (d, J=5.5 Hz, 1H) 3.96 (m, 2H), 3.11-3.88 (m, 5H), 2.93 (dd, J=12.8, 10.4, 1H). MS (calc'd) 263.1 (M+H, found) 264.1.

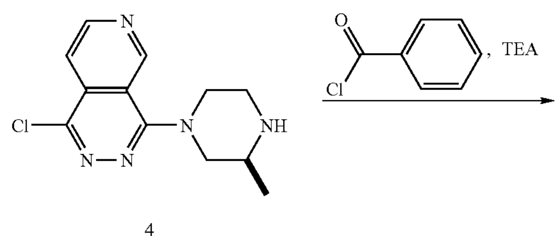

-continued

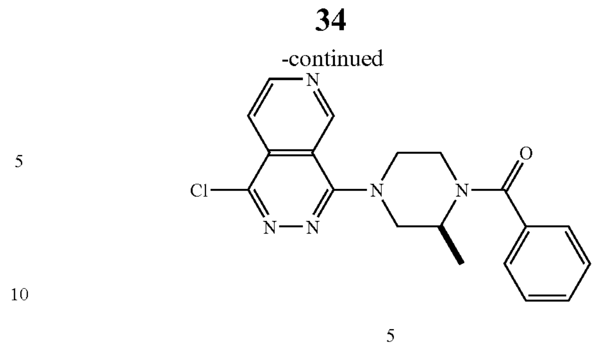

Step 4. To (S)-1-chloro-4-(3-methylpiperazin-1-yl)pyrido[3,4-d]pyridazine 4 (0.190 g, 0.720 mmol) in dichloromethane (3 ml) was added benzoyl chloride (0.0920 ml, 0.792 mmol) and triethylamine (0.220 ml, 1.58 mmol). The reaction was stirred at 25° C. After 2 h, the reaction contents were poured into saturated sodium bicarbonate (6 mL). The aqueous layer was brought to pH 11 with 5 N NaOH and extracted with 10% methanol in dichloromethane (3×15 mL). Silica gel chromatography (gradient elution 30 to 60% EtOAc in hexanes with 2.5% TEA additive) afforded 210 mg of (S)-(4-(1-chloropyrido[3,4-d]pyridazin-4-yl)-2-methylpiperazin-1-yl)(phenyl)methanone 5. $^{1}$H NMR ($CDCl_3$) δ 9.55 (s, 1H), 9.08 (d, J=5.9 Hz, 1H), 8.00 (d, J=5.1 Hz, 1H) 7.41-7.51 (m, 5H) 4.70 (m, 1H), 4.02 (app d, J=11.7 Hz, 1H), 3.86 (app d, J=12.1 Hz, 1H) 3.62-3.72 (m, 1H), 3.47 (dd, J=13.1, 3.3 Hz, 1H), 3.30 (td, J=12.6, 3.3 Hz, 1H), 1.61 (bs, 1H), 1.57 (d, J=6.3 Hz, 3H).

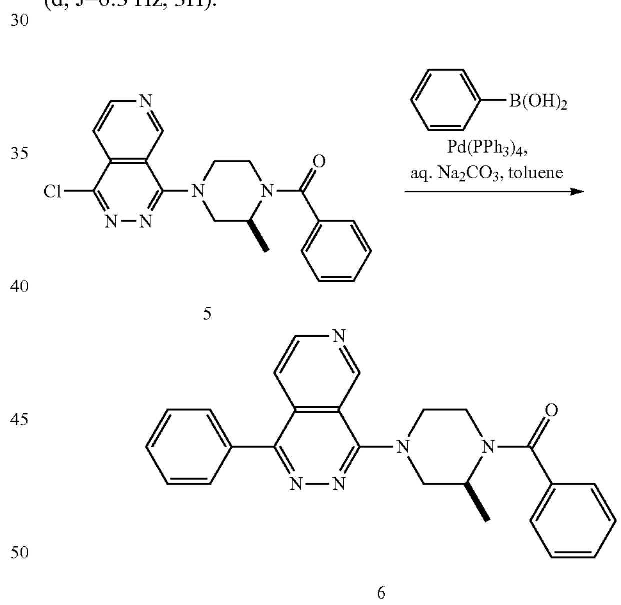

Step 5. (S)-(4-(1-chloropyrido[3,4-d]pyridazin-4-yl)-2-methylpiperazin-1-yl)(phenyl)methanone 5 (0.100 g, 0.272 mmol), tetrakis(triphenylphosphine)palladium(0) (0.0220 g, 0.0190 mmol), and phenylboronic acid (0.050 mg, 0.41 mmol) were combined in a screw cap vial and solvated under argon atmosphere with degassed toluene (2.70 ml) and 2 M $Na_2CO_3$ (0.270 ml, 0.540 mmol). The reaction was briefly sparged with argon, then sealed and stirred at 95° C. After 16 h, the reaction contents were poured into water (10 ml). The aqueous layer was extracted with dichloromethane (3×20 mL). Combined organics were dried with $Na_2SO_4$ and removed in vacuo. Silica gel chromatography (gradient elution 0 to 5% MeOH in $CH_2Cl_2$) afforded 70 mg of 6. MS (calc'd) 409.2 (M+H, found) 410.2.

EXAMPLE 2

Preparation of (S)-(2-methyl-4-(1-(4-(trifluoromethyl)phenyl)pyrido[3,4-d]pyridazin-4-yl)piperazin-1-yl)(phenyl)methanone

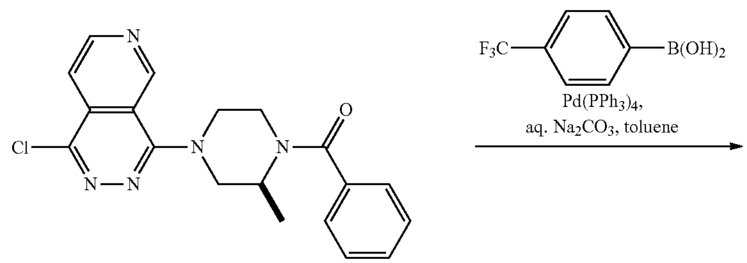

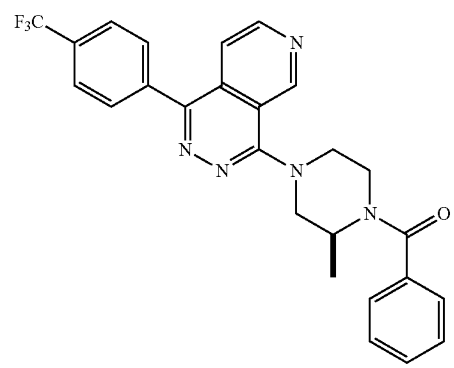

Using methods described in Example 1, and starting with 4-(trifluoromethyl)phenylboronic acid, (S)-(2-methyl-4-(1-(4-(trifluoromethyl)phenyl)pyrido[3,4-d]pyridazin-4-yl)piperazin-1-yl)(phenyl)methanone 6 was prepared. MS (calc'd) 477.2 (M+H, found) 478.1.

EXAMPLE 3

Preparation of (S)-(2-methyl-4-(1-(4-(trifluoromethyl)phenyl)pyrido[3,4-d]pyridazin-4-yl)piperazin-1-yl)(piperidin-1-yl)methanone

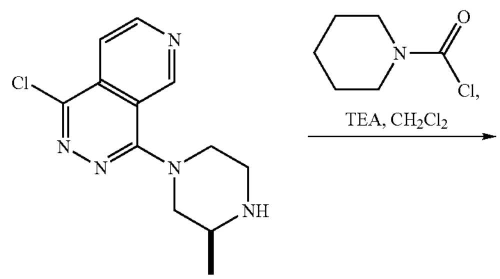

-continued

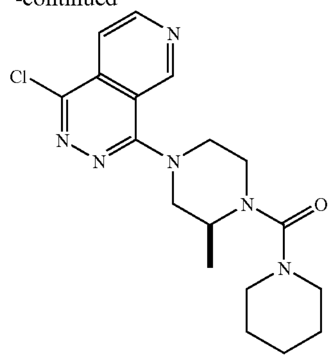

Step 1. To a solution of (S)-1-chloro-4-(3-methylpiperazin-1-yl)pyrido[3,4-d]pyridazine 4 (500 mg, 1.90 mmol) in 10 mL of $CH_2Cl_2$ was added triethylamine (529 µl, 3.79 mmol), followed by 1-piperidinecarbonyl chloride (364 µl, 2.47 mmol). The reaction was allowed to stir overnight and then diluted with 100 mL of ethyl acetate. The crude mixture was washed with 1×10 mL of sat. $NaHCO_3$, 1×10 mL of water, and 1×10 mL of brine. The organic layer was dried over $MgSO_4$, filtered, and concentrated. Purification by column chromatography afforded (S)-(4-(1-chloropyrido[3,4-d]pyridazin-4-yl)-2-methylpiperazin-1-yl)(piperidin-1-yl)methanone 7.

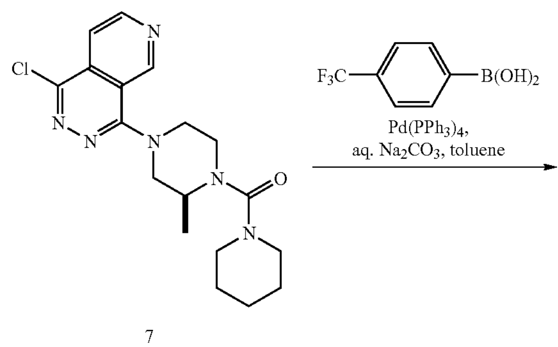

7

-continued

9

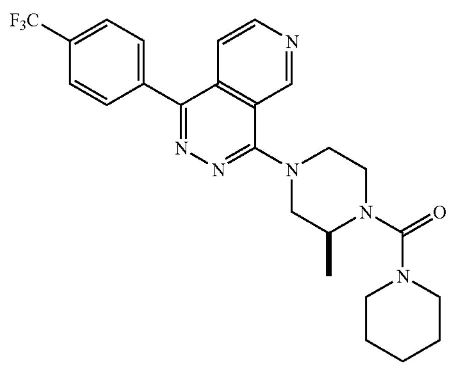

8

Step 2. Using methods described in Example 1, and starting with (S)-(4-(1-chloropyrido[3,4-d]pyridazin-4-yl)-2-methylpiperazin-1-yl)(piperidin-1-yl)methanone 7 (150 mg, 400 μmol), $Pd(PPh_3)_4$ (23 mg, 20 μmol), 4-(trifluoromethyl)phenylboronic acid (106 mg, 560 μmol), and 2 M sodium carbonate (400 μl, 800 μmol), (S)-(2-methyl-4-(1-(4-(trifluoromethyl)phenyl)pyrido[3,4-d]pyridazin-4-yl)piperazin-1-yl)(piperidin-1-yl)methanone 8 was obtained. MS 484.2 (calc'd) 485.2 (M+H, found).

EXAMPLE 4

Preparation of (S)-(4-(1-(4-(hydroxymethyl)phenyl)pyrido[3,4-d]pyridazin-4-yl)-2-methylpiperazin-1-yl)(piperidin-1-yl)methanone

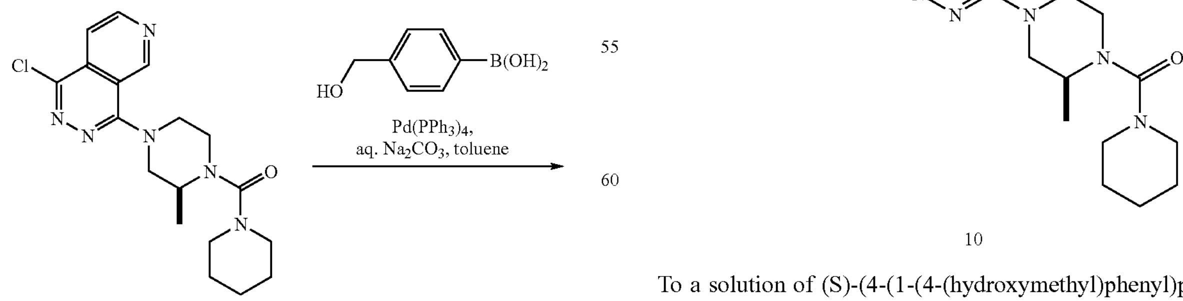

7

Using methods described in Example 1, and starting with (S)-(4-(1-chloropyrido[3,4-d]pyridazin-4-yl)-2-methylpiperazin-1-yl)(piperidin-1-yl)methanone 7 (200 mg, 534 μmol), tetrakis(triphenylphosphine)palladium (31 mg, 27 μmol), 4-(hydroxymethyl)phenylboronic acid (122 mg, 800 μmol) and 2 M sodium carbonate (534 μl, 1067 μmol), (S)-(4-(1-(4-(hydroxymethyl)phenyl)pyrido[3,4-d]pyridazin-4-yl)-2-methylpiperazin-1-yl)(piperidin-1-yl)methanone 9 was obtained. MS 446.2 (calc'd) 447.3 (M+H, found).

EXAMPLE 5

Preparation of (S)-(4-(4-(3-methyl-4-(piperidine-1-carbonyl)piperazin-1-yl)pyrido[3,4-d]pyridazin-1-yl)phenyl)methyl carbamate

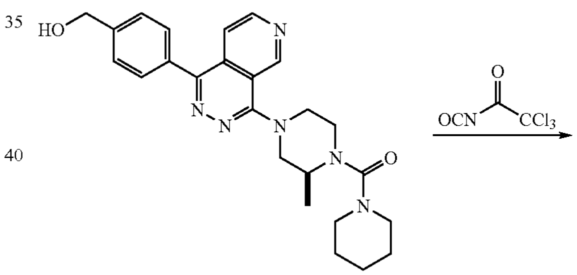

9

10

To a solution of (S)-(4-(1-(4-(hydroxymethyl)phenyl)pyrido[3,4-d]pyridazin-4-yl)-2-methylpiperazin-1-yl)(piperidin-1-yl)methanone 9 (100 mg, 224 μmol) in chloroform (2 mL) was added 2,2,2-trichloroacetyl isocyanate (39 μl, 314

μmol). The reaction was stirred at RT for 1 h and deposited on 3 g of Alumina (Brockmann II). After 1 h, the product was eluted from the alumina with 10% MeOH in dichloromethane. The crude reaction product was concentrated and purified by column chromatography to afford (S)-(4-(4-(3-methyl-4-(piperidine-1-carbonyl)piperazin-1-yl)pyrido[3,4-d]pyridazin-1-yl)phenyl)methyl carbamate 10. MS 489.2 (calc'd) 490.1 (M+H, found).

EXAMPLE 6

Preparation of ((R)-4-(1-(4-chloro-2-fluorophenyl) pyrido[3,4-d]pyridazin-4-yl)-3-methylpiperazin-1-yl) (phenyl)methanone

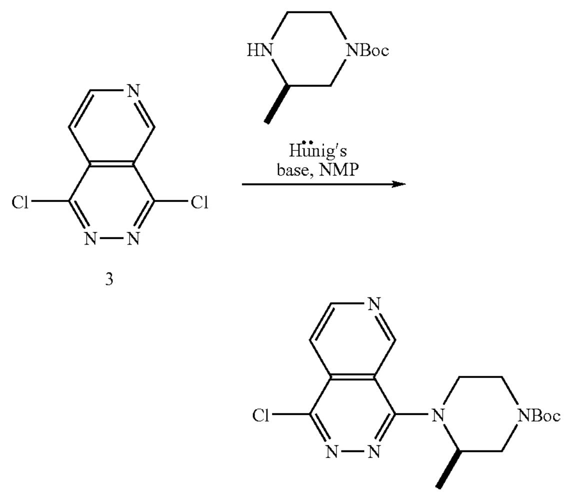

Step 1. 1,4-dichloropyrido[3,4-d]pyridazine 3 (3.50 g, 17.5 mmol), (R)-tert-butyl 3-methylpiperazine-1-carboxylate (3.85 g, 19.2 mmol), N,N-diisopropylethylamine (10.7 ml, 61.2 mmol), and 1-methyl-2-pyrrolidinone (7 ml) were placed in a 50 ml flask and heated for 18 hours at 100° C. The reaction was the taken up in ethyl acetate (80 ml) and washed with aqueous $K_2CO_3$ (10%), water, and brine. The organic phase was dried ($MgSO_4$) and evaporated to give a brown oil. The residue was chromatographed over silica with a gradient of hexane to 100% ethyl acetate. The product 11 was isolated as a tan solid. $^1$H NMR (500 MHz, $CDCl_3$) δ ppm 9.47 (s, 1H) 9.05 (d, J=5.62 Hz, 1H) 7.96 (d, J=5.62 Hz, 1H) 3.21-4.32 (m, 7H) 1.51 (s, 9H) 1.31 (d, J=6.60 Hz, 3H). LC/MS m/z=364 (M+H$^+$).

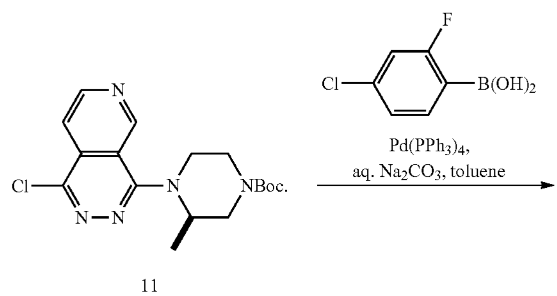

-continued

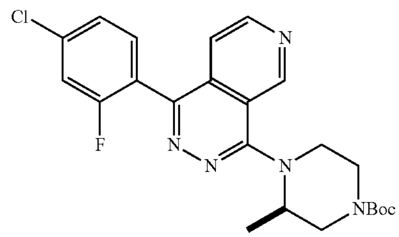

Step 2. Using methods described in Example 1 and starting with (R)-tert-butyl 4-(1-chloropyrido[3,4-d]pyridazin-4-yl)-3-methylpiperazine-1-carboxylate 11 and 4-chloro-2-fluorophenylboronic acid, (3R)-tert-butyl 4-(1-(4-chloro-2-fluorophenyl)pyrido[3,4-d]pyridazin-4-yl)-3-methylpiperazine-1-carboxylate 12 was prepared. $^1$H NMR (500 MHz, 500 MHz, $CDCl_3$)) δ ppm 9.52 (s, 1H) 8.91 (d, J=5.62 Hz, 1H) 7.68 (t, J=7.95 Hz, 1H) 7.44-7.50 (m, 1H) 7.38 (d, J=8.31, 1.71 Hz, 1H) 7.32 (d, J=9.78, 1.71 Hz, 1H) 3.25-4.52 (m, 7H) 1.52 (s, 9H) 1.39 (d, J=6.36 Hz, 3H). LC/MS m/z=458 (M+H$^+$).

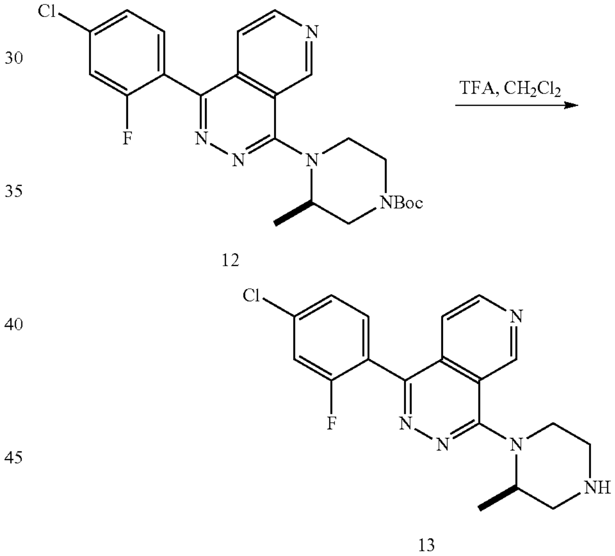

Step 3. (3R)-tert-butyl 4-(1-(4-chloro-2-fluorophenyl)pyrido[3,4-d]pyridazin-4-yl)-3-methylpiperazine-1-carboxylate 12 (310 mg, 0.68 mmol) was dissolved in dichloromethane (6 ml). Trifluoroacetic acid (1.30 ml, 16 mmol) was added and the reaction stirred for 2 hours. The reaction was poured in saturated aqueous $NaHCO_3$ (30 ml) and then extracted three times with dichloromethane (30 ml). The combined organic phases were dried ($MgSO_4$) and evaporated to give an off white solid 13, 236 mg. $^1$H NMR (500 MHz, 500 MHz, $CDCl_3$) δ ppm 9.54 (s, 1H) 8.90 (d, J=5.62 Hz, 1H) 7.69 (t, J=8.07 Hz, 1H) 7.43-7.47 (m, 1H) 7.38 (d, J=8.31, 1.47 Hz, 1H) 7.32 (d, J=9.78, 1.71 Hz, 1H) 4.28-4.43 (m, J=6.48, 3.30 Hz, 1H) 3.76-3.82 (m, 1H) 3.68-3.76 (m, 1H) 3.36 (dd, J=12.23, 3.42 Hz, 1H) 3.20 (dd, J=6.36, 3.67 Hz, 2H) 2.95 (dd, J=12.23, 3.42 Hz, 1H) 1.44 (d, J=6.36 Hz, 3H). LC/MS m/z=358 (M+H$^+$).

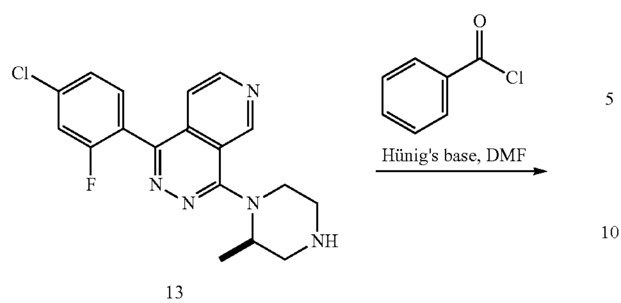

-continued

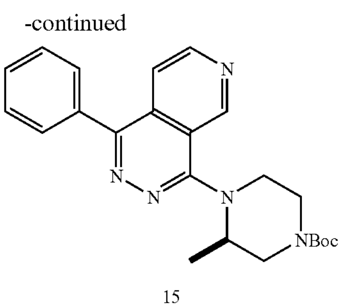

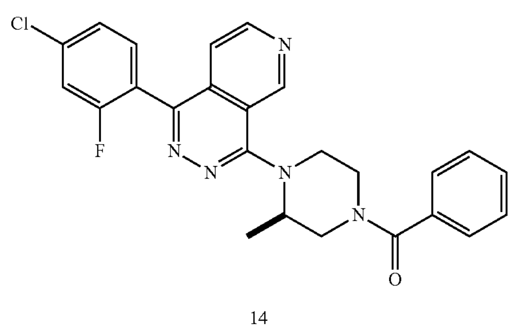

Step 4. 1-(4-chloro-2-fluorophenyl)-4-((R)-2-methylpiperazin-1-yl)pyrido[3,4-d]pyridazine (118 mg, 330 μmol) was dissolved in Hünig's base 13 (0.200 ml, 1148 μmol) and DMF (2 ml). Benzoyl chloride (0.0478 ml, 412 μmol) was added and the solution stirred at RT for 2 days. The reaction was then taken up in ethyl acetate (30 ml) and washed with aqueous $K_2CO_3$ (10%), water, and brine. The organic phase was dried ($MgSO_4$) and evaporated to give an orange oil. Chromatography of the residue over silica with a gradient of hexane to 100% ethyl acetate gave ((R)-4-(1-(4-chloro-2-fluorophenyl)pyrido[3,4-d]pyridazin-4-yl)-3-methylpiperazin-1-yl)(phenyl)methanone 14 as a yellow solid. LC/MS m/z=462 ($M+H^+$).

EXAMPLE 7

Preparation of (R)-(4,4-difluorocyclohexyl)(3-methyl-4-(1-phenylpyrido[3,4-d]pyridazin-4-yl)piperazin-1-yl)methanone

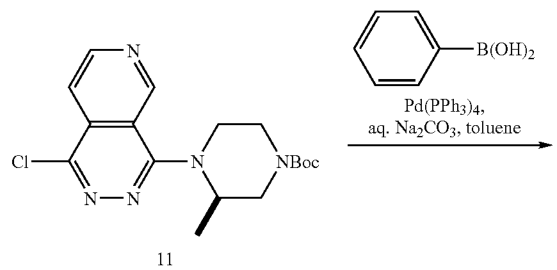

Step 1. Using methods described in Example 1 and starting with (R)-tert-butyl 4-(1-chloropyrido[3,4-d]pyridazin-4-yl)-3-methylpiperazine-1-carboxylate 11 (800 mg, 2.20 mmol) and phenylboronic acid (375 mg, 3.08 mmol), (R)-tert-butyl 3-methyl-4-(1-phenylpyrido[3,4-d]pyridazin-4-yl)piperazine-1-carboxylate 15 was prepared. $^1H$ NMR (500 MHz, $CDCl_3$) δ ppm 9.54 (s, 1H) 8.92 (d, J=5.62 Hz, 1H) 7.83 (d, J=5.62 Hz, 1H) 7.78 (d, J=6.36 Hz, 2H) 7.53-7.62 (m, 3H) 4.29-4.38 (m, 1H) 3.34-4.18 (m, 6H) 1.52 (s, 9H) 1.36 (d, J=6.36 Hz, 3H). LC/MS m/z=406 ($M+H^+$).

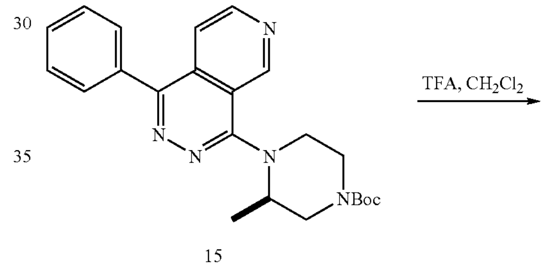

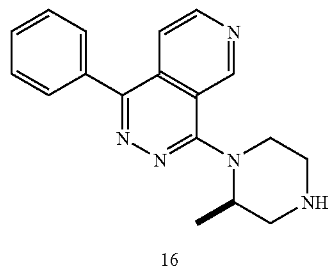

Step 2. Using methods described in Example 6 and starting with (R)-tert-butyl 3-methyl-4-(1-phenylpyrido[3,4-d]pyridazin-4-yl)piperazine-1-carboxylate 15, (R)-4-(2-methylpiperazin-1-yl)-1-phenylpyrido[3,4-d]pyridazine 16 was prepared. $^1H$ NMR (500 MHz, $CDCl_3$) δ ppm 9.57 (s, 1H) 8.91 (d, J=5.62 Hz, 1H) 7.83 (d, J=5.62 Hz, 1H) 7.78 (d, J=6.36 Hz, 2H) 7.51-7.62 (m, 3H) 4.22-4.35 (m, 1H) 3.67-3.75 (m, 2H) 3.32-3.44 (m, J=12.47, 3.42 Hz, 1H) 3.18-3.25 (m, J=4.89, 4.89 Hz, 2H) 2.90-3.03 (m, J=12.47, 4.16 Hz, 1H) 1.41 (d, J=6.60 Hz, 3H). LC/MS m/z=306 ($M+H^+$).

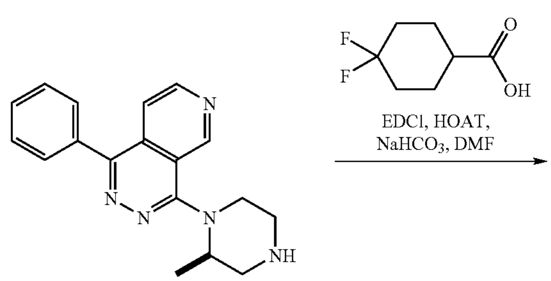

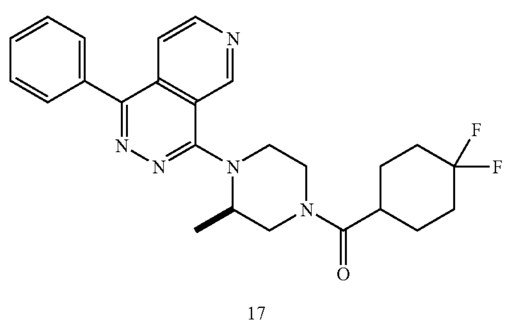

Step 3. (R)-4-(2-methylpiperazin-1-yl)-1-phenylpyrido[3,4-d]pyridazine 16 (150 mg, 491 μmol), 4,4-difluorocyclohexanecarboxylic acid (88.7 mg, 540 μmol), N1-((ethylimino)methylene)-N3,N3-dimethylpropane-1,3-diamine hydrochloride (113 mg, 589 μmol), 3H-[1,2,3]triazolo[4,5-b]pyridin-3-ol (80.2 mg, 589 μmol), sodium bicarbonate (82.5 mg, 982 μmol) were stirred in DMF (3 ml) for one hour. The reaction was then taken up in ethyl acetate (30 ml) and washed with aqueous $K_2CO_3$ (10%), water, and brine. The organic phase was dried ($MgSO_4$) and evaporated to give an orange oil. Chromatography of the residue over silica with a gradient of hexane to 100% ethyl acetate gave (R)-(4,4-difluorocyclohexyl)(3-methyl-4-(1-phenylpyrido[3,4-d]pyridazin-4-yl)piperazin-1-yl)methanone 17 as a yellow solid. LC/MS m/z=452 ($M+H^+$).

EXAMPLE 8

Preparation of (R)-cyclohexyl(3-methyl-4-(1-phenylpyrido[3,4-d]pyridazin-4-yl)piperazin-1-yl)methanone

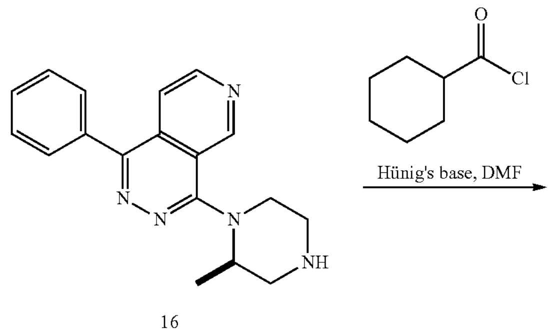

-continued

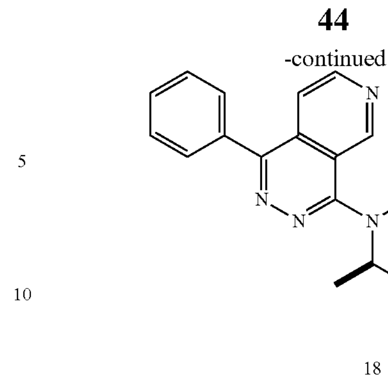

Using methods described in Example 6 and starting with (R)-4-(2-methylpiperazin-1-yl)-1-phenylpyrido[3,4-d]pyridazine 16 and cyclohexanecarbonyl chloride 16, (R)-cyclohexyl(3-methyl-4-(1-phenylpyrido[3,4-d]pyridazin-4-yl)piperazin-1-yl)methanone 18 was prepared. LC/MS m/z=416 ($M+H^+$).

EXAMPLE 9

Preparation of ((R)-4-(1-(4-chloro-2-fluorophenyl)pyrido[3,4-d]pyridazin-4-yl)-3-methylpiperazin-1-yl)(cyclohexyl)methanone

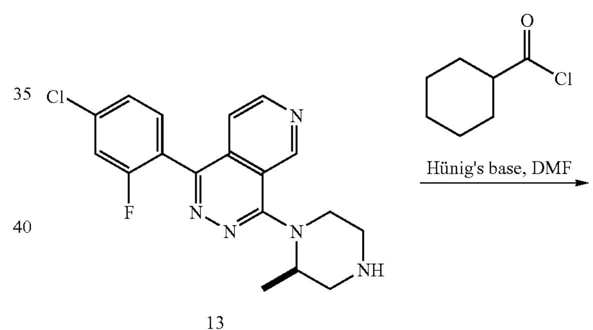

19

Using methods described in Example 6 and starting with 1-(4-chloro-2-fluorophenyl)-4-((R)-2-methylpiperazin-1-yl)pyrido[3,4-d]pyridazine and cyclohexanecarbonyl chloride 13, ((R)-4-(1-(4-chloro-2-fluorophenyl)pyrido[3,4-d]pyridazin-4-yl)-3-methylpiperazin-1-yl)(cyclohexyl)methanone 19 was prepared. LC/MS m/z=468 ($M+H^+$).

EXAMPLE 10

Preparation of (R)-(3-methyl-4-(1-(4-(trifluoromethyl)phenyl)pyrido[3,4-d]pyridazin-4-yl)piperazin-1-yl)(phenyl)methanone

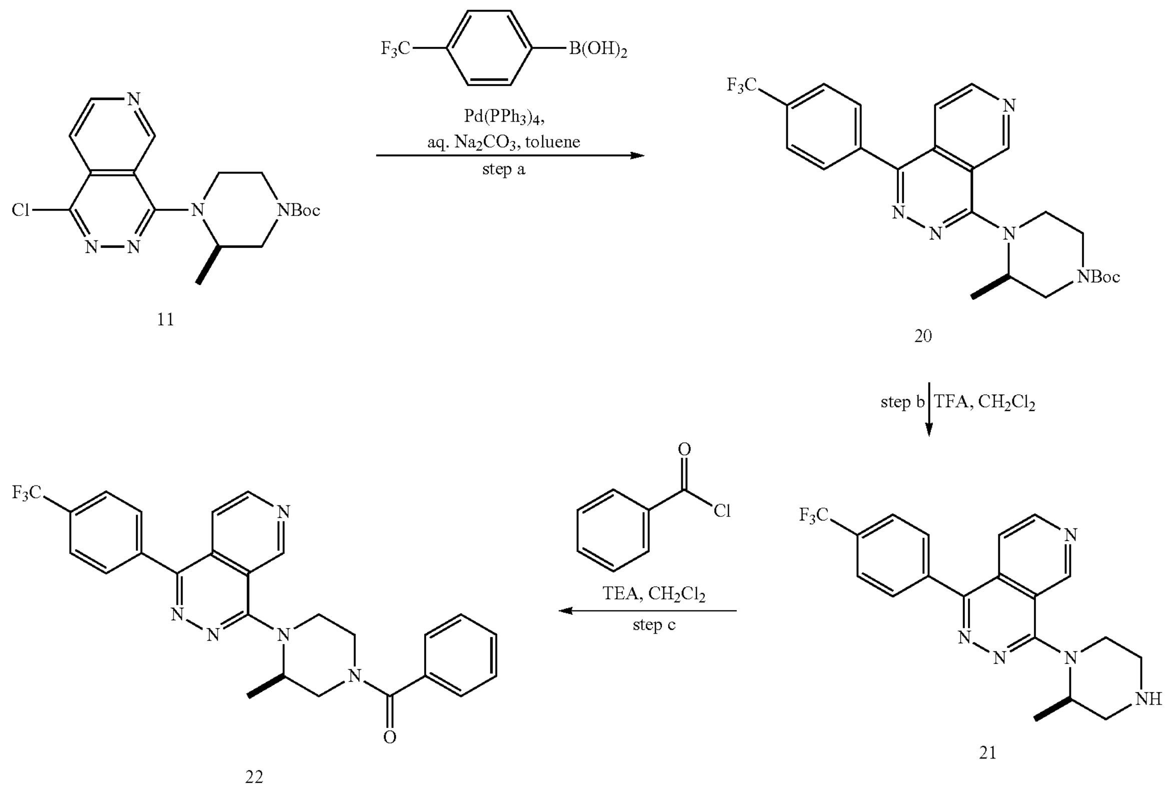

Step 1. Using methods described in Example 1, and starting with (R)-tert-butyl 4-(1-chloropyrido[3,4-d]pyridazin-4-yl)-3-methylpiperazine-1-carboxylate 11 and 4-(trifluoromethyl)phenylboronic acid, (R)-tert-butyl 3-methyl-4-(1-(4-(trifluoromethyl)phenyl)pyrido[3,4-d]pyridazin-4-yl) piperazine-1-carboxylate 20 was prepared. The crude material was carried on to Step 2 without further purification.

Step 2. Using methods described in Example 6 and starting with (R)-tert-butyl 3-methyl-4-(1-(4-(trifluoromethyl)phenyl)pyrido[3,4-d]pyridazin-4-yl)piperazine-1-carboxylate 20 prepared above, (R)-4-(2-methylpiperazin-1-yl)-1-(4-(trifluoromethyl)phenyl)pyrido[3,4-d]pyridazine 21 was prepared. The crude material was carried on to step c without further purification.

Step 3. To triethylamine (0.315 ml, 2.26 mmol) and (R)-4-(2-methylpiperazin-1-yl)-1-(4-(trifluoromethyl)phenyl)pyrido[3,4-d]pyridazine 21 (0.352 g, 0.943 mmol), in $CH_2Cl_2$ (3.1 ml) was added benzoyl chloride (0.120 ml, 1.04 mmol). The reaction was stirred at 25° C. After 2 h, the reaction contents were poured into saturated sodium bicarbonate (10 mL) and extracted with dichloromethane (3×15 mL). The combined organics were dried with $Na_2SO_4$ and concentrated in vacuo. Silica gel chromatography (gradient elution 20 to 90% EtOAc in $CH_2Cl_2$) afforded 347 mg of desired product (R)-(3-methyl-4-(1-(4-(trifluoromethyl)phenyl)pyrido[3,4-d]pyridazin-4-yl)piperazin-1-yl)(phenyl)methanone 22 (77% yield). $^1$H NMR (500 MHz, $CDCl_3$) δ ppm 9.57 (s, 1H) 8.96 (d, J=6.1 Hz, 1H) 7.81-7.97 (m, 4H) 7.77 (d, J=5.5 Hz, 1H) 7.47 (s, 5H) 3.30-4.82 (m, 7H) 1.29-1.53 (m, 3H).

EXAMPLE 11

Preparation of (R)-(3-methyl-4-(1-phenylpyrido[3,4-d]pyridazin-4-yl)piperazin-1-yl)(phenyl)methanone

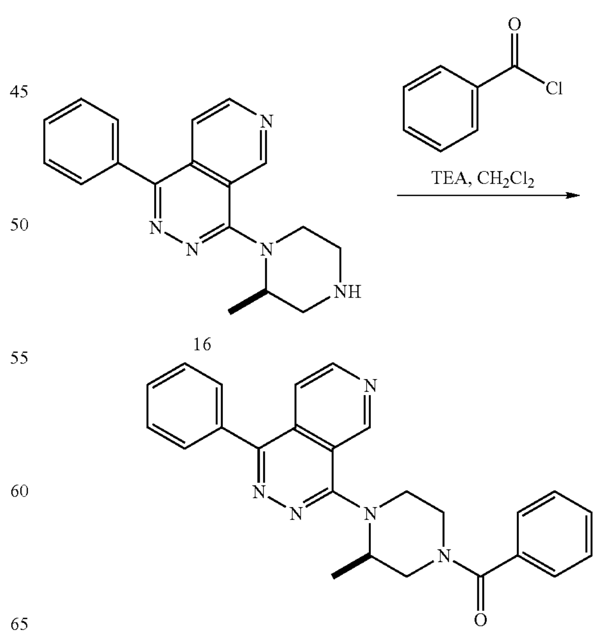

Using methods described in Example 10 step c, and starting with (R)-4-(2-methylpiperazin-1-yl)-1-phenylpyrido[3,4-d]pyridazine 16, (R)-(3-methyl-4-(1-phenylpyrido[3,4-d]pyridazin-4-yl)piperazin-1-yl)(phenyl)methanone 23 was prepared. $^1$H NMR (500 MHz, $CDCl_3$) δ ppm 9.56 (s, 1H) 8.94 (d, J=5.5 Hz, 1H) 7.84 (d, J=5.5 Hz, 1H) 7.77 (d, J=6.1 Hz, 2H) 7.54-7.66 (m, 3H) 7.40-7.52 (m, 5H) 3.28-4.82 (m, 7H) 1.30-1.52 (m, 3H).

EXAMPLE 12

Preparation of ((1s,4S)-4-hydroxycyclohexyl)((R)-3-methyl-4-(1-phenylpyrido[3,4-d]pyridazin-4-yl)piperazin-1-yl)methanone

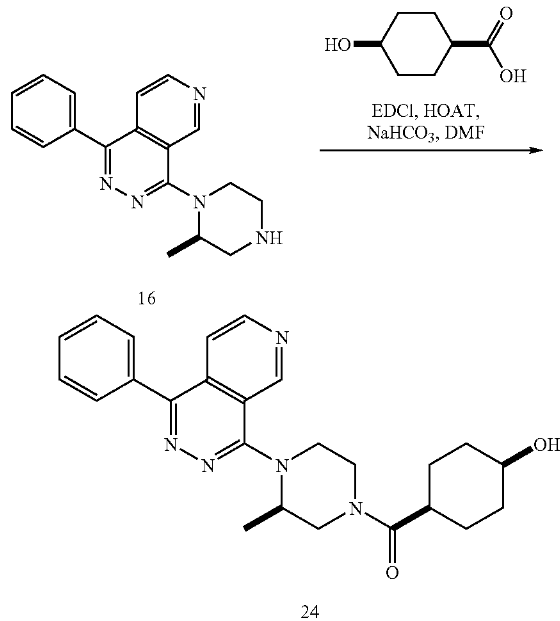

Using methods described in Example 7, and starting with (1s,4s)-4-hydroxycyclohexanecarboxylic acid, ((1s,4S)-4-hydroxycyclohexyl)((R)-3-methyl-4-(1-phenylpyrido[3,4-d]pyridazin-4-yl)piperazin-1-yl)methanone 24 was prepared. MS (calc'd) 431.2 (M+H, found) 432.2.

EXAMPLE 13

Preparation of ((1r,4R)-4-hydroxycyclohexyl)((R)-3-methyl-4-(1-phenylpyrido[3,4-d]pyridazin-4-yl)piperazin-1-yl)methanone

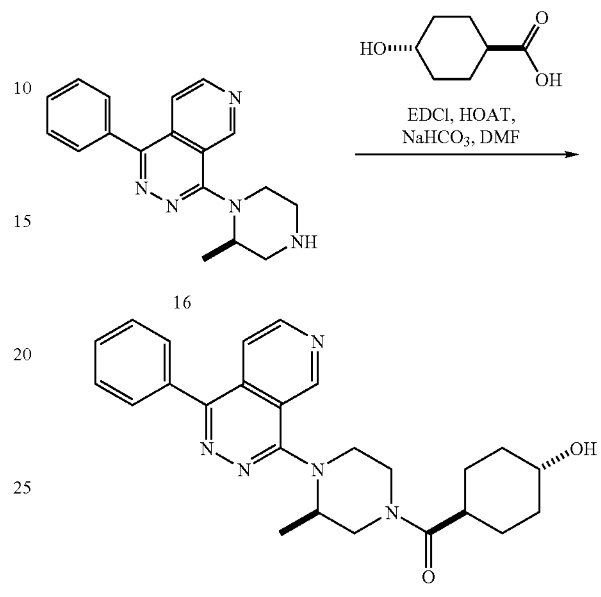

Using methods described in Example 7, and starting with (1r,4r)-4-hydroxycyclohexanecarboxylic acid, ((1r,4R)-4-hydroxycyclohexyl)((R)-3-methyl-4-(1-phenylpyrido[3,4-d]pyridazin-4-yl)piperazin-1-yl)methanone 25 was prepared. $^1$H NMR (500 MHz, $CDCl_3$) δ ppm 9.57 (s, 1H) 8.96 (d, J=5.6 Hz, 1H) 7.87 (d, J=5.6 Hz, 1H) 7.72-7.81 (m, 2H) 7.51-7.65 (m, 3H) 4.29-4.61 (m, 2H) 3.94-4.09 (m, 1H) 3.61-3.82 (m, 3H) 3.35-3.51 (m, 1H) 2.45-2.64 (m, 1H) 2.03-2.20 (m, 2H) 1.57-1.97 (m, 6H) 1.28-1.47 (m, 5H).

EXAMPLE 14

Preparation of (R)-(3-methyl-4-(4-phenylpyrido[4,3-d]pyridazin-1-yl)piperazin-1-yl)(phenyl)methanone

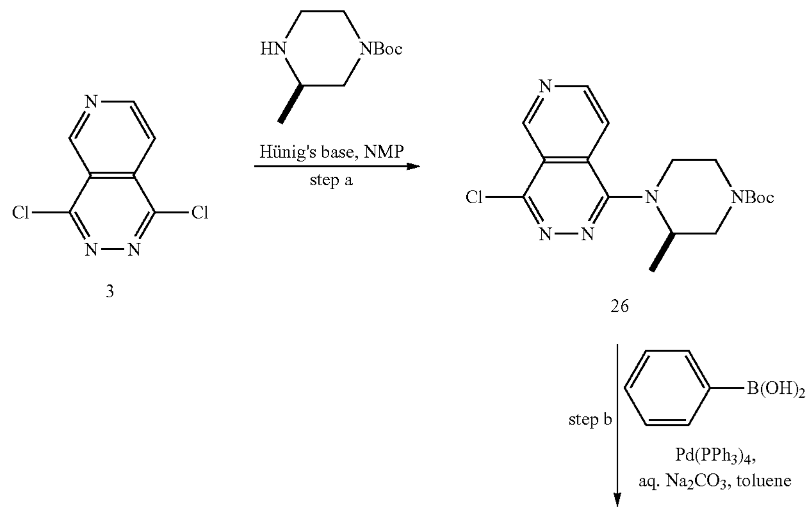

-continued

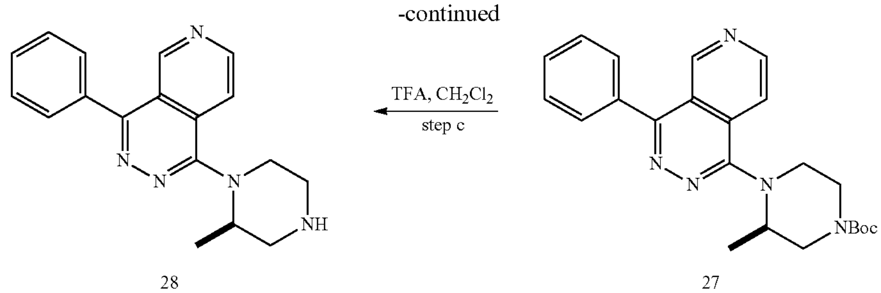

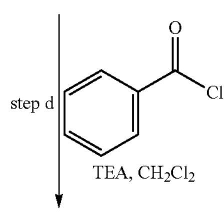

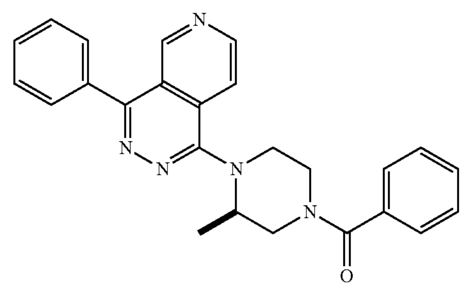

Step 1. To (R)-tert-butyl 3-methylpiperazine-1-carboxylate (3.30 g, 16.5 mmol) and 1,4-dichloropyrido[4,3-d]pyridazine 3 (3.00 g, 15.0 mmol), suspended in Hünig's base (9.14 ml, 52.5 mmol) was added NMP (6 ml). The reaction was stirred at 100° C. The reaction contents were poured into water (120 mL) and extracted with dichloromethane (3×50 mL). Silica gel chromatography (gradient elution 20 to 80% EtOAc in hexanes) afforded 110 mg of (R)-tert-butyl 4-(4-chloropyrido[4,3-d]pyridazin-1-yl)-3-methylpiperazine-1-carboxylate 26 eluting after the 1-substitution product. $^1H$ NMR (500 MHz, $CDCl_3$) δ ppm 9.66 (s, 1H) 9.06 (d, J=6.1 Hz, 1H) 7.77 (d, J=5.5 Hz, 1H) 3.28-4.23 (m, 7H) 1.51 (s, 9H) 1.28 (d, J=6.7 Hz, 3H).

Step 2. Using methods described in Example 1, and starting with (R)-tert-butyl 4-(4-chloropyrido[4,3-d]pyridazin-1-yl)-3-methylpiperazine-1-carboxylate 26, (R)-tert-butyl 3-methyl-4-(4-phenylpyrido[4,3-d]pyridazin-1-yl)piperazine-1-carboxylate 27 was prepared. The crude material was carried on to the next step without purification.

Step 3. Using methods described in Example 6, and starting with (R)-tert-butyl 3-methyl-4-(4-phenylpyrido[4,3-d]pyridazin-1-yl)piperazine-1-carboxylate 27, (R)-1-(2-methylpiperazin-1-yl)-4-phenylpyrido[4,3-d]pyridazine 28 was prepared. The crude material was carried on to the next step without purification.

Step 4. Using methods described in Example 10 Step 3, and starting with (R)-1-(2-methylpiperazin-1-yl)-4-phenylpyrido[4,3-d]pyridazine 28, (R)-(3-methyl-4-(4-phenylpyrido[4,3-d]pyridazin-1-yl)piperazin-1-yl)(phenyl)methanone 29 was prepared. MS (calc'd) 409.2 (M+H, found) 410.2.

EXAMPLE 15

Preparation of (R)-(3-methyl-4-(1-phenylpyrido[4,3-d]pyridazin-4-yl)piperazin-1-yl)(tetrahydro-2H-pyran-4-yl)methanone

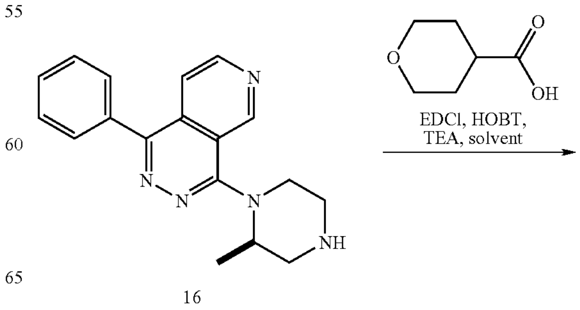

-continued

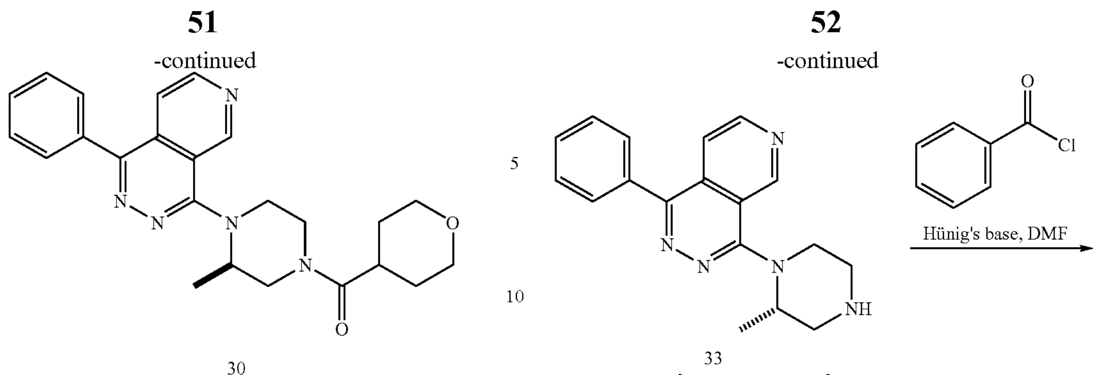

To a solution of (R)-4-(2-methylpiperazin-1-yl)-1-phenylpyrido[4,3-d]pyridazine 16 (125 mg, 409 μmol) in dichloromethane (5 mL) was added HOBT (3.1 mg, 20 μmol), EDCI (86 mg, 450 μmol), triethylamine (114 μl, 819 μmol), and tetrahydro-2H-pyran-4-carboxylic acid (64 mg, 491 μmol). After 1 hour, 10 mL of sat $NaHCO_3$ and 100 mL of ethyl acetate were added. The layers were separated and the organic layer was washed with 1×10 mL of brine, dried over $MgSO_4$, filtered, and concentrated. Purified by column chromatography (hexanes:acetone) to isolate (R)-(3-methyl-4-(1-phenylpyrido[4,3-d]pyridazin-4-yl)piperazin-1-yl)(tetrahydro-2H-pyran-4-yl)methanone 30. MS: 417.2 (calc'd) 418.1 (M+H, found).

EXAMPLE 16

Preparation of (S)-(3-methyl-4-(1-phenylpyrido[3,4-d]pyridazin-4-yl)piperazin-1-yl)(phenyl)methanone

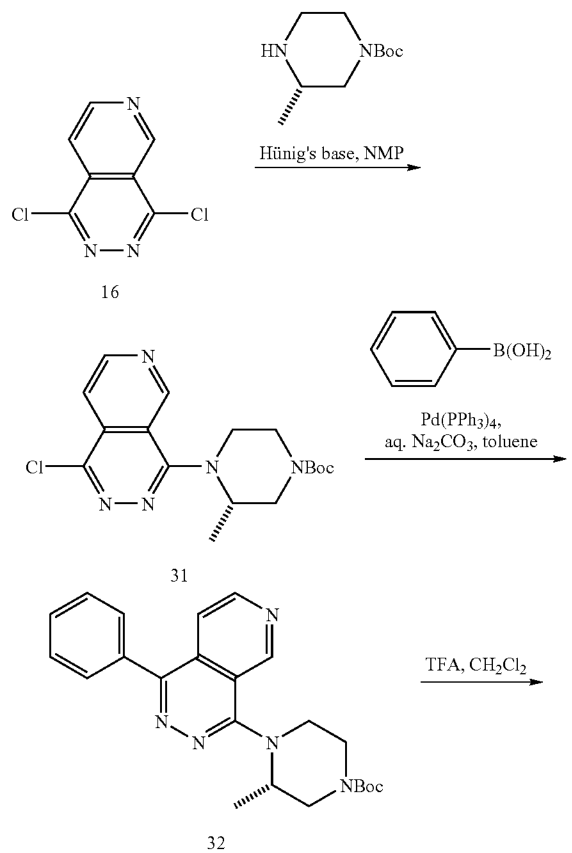

34

Step 1. Using methods described in Example 6 starting with 1,4-dichloropyrido[3,4-d]pyridazine 3 and (S)-tert-butyl 3-methylpiperazine-1-carboxylate, 4-(1-chloropyrido[3,4-d]pyridazin-4-yl)-3-methylpiperazine-1-carboxylate 31 was prepared. LC/MS m/z=364 (M+H$^+$).

Step 2. Using methods described in Example 6 starting with 4-(1-chloropyrido[3,4-d]pyridazin-4-yl)-3-methylpiperazine-1-carboxylate 31 and phenylboronic acid, 3-methyl-4-(1-phenylpyrido[3,4-d]pyridazin-4-yl)piperazine-1-carboxylate 32 was prepared. LC/MS m/z=406 (M+H$^+$).

Step 3. Using methods described in Example 6 starting with 3-methyl-4-(1-phenylpyrido[3,4-d]pyridazin-4-yl)piperazine-1-carboxylate 32, (S)-4-(2-methylpiperazin-1-yl)-1-phenylpyrido[3,4-d]pyridazine 33 was prepared. LC/MS m/z=306 (M+H$^+$).

Step 4. Using methods described in Example 6 starting with (S)-4-(2-methylpiperazin-1-yl)-1-phenylpyrido[3,4-d]pyridazine 33 and benzoyl chloride, (S)-(3-methyl-4-(1-phenylpyrido[3,4-d]pyridazin-4-yl)piperazin-1-yl)(phenyl)methanone 34 was prepared. LC/MS m/z=410 (M+H$^+$).

EXAMPLE 17

Preparation of (S)-(4,4-difluorocyclohexyl)(3-methyl-4-(1-phenylpyrido[3,4-d]pyridazin-4-yl)piperazin-1-yl)methanone

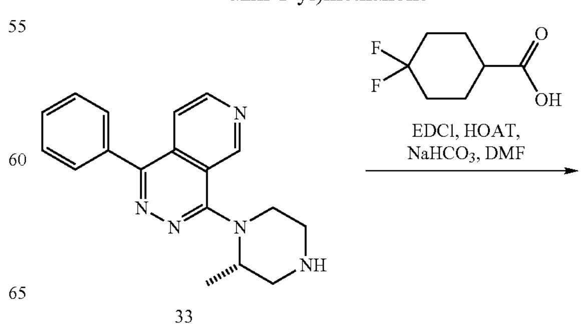

-continued

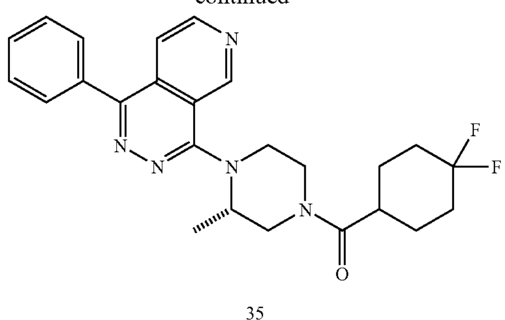

35

Using methods described in Example 7 starting with (S)-4-(2-methylpiperazin-1-yl)-1-phenylpyrido[3,4-d]pyridazine 33 and 4,4-difluorocyclohexanecarboxylic acid, (S)-(4,4-difluorocyclohexyl)(3-methyl-4-(1-phenylpyrido[3,4-d]pyridazin-4-yl)piperazin-1-yl)methanone 35 was prepared. LC/MS m/z=452 (M+H$^+$).

EXAMPLE 18

Preparation of (R)-(3-methyl-4-(1-phenylpyrido[3,4-d]pyridazin-4-yl)piperazin-1-yl)(morpholino)methanone

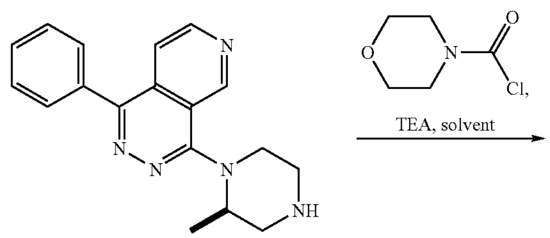

16

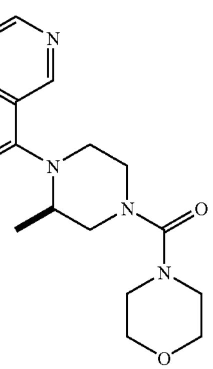

36

To a solution of (R)-4-(2-methylpiperazin-1-yl)-1-phenylpyrido[3,4-d]pyridazine 16 (105 mg, 344 μmol) in 5 mL of $CH_2Cl_2$ was added triethylamine (96 μl, 688 μmol) followed by 4-morpholinylcarbonyl chloride (55 μl, 413 μmol). After 4 h, the reaction was diluted with 60 mL of EtOAc and washed with sat. $NaHCO_3$ and brine. The organic layer was dried over $MgSO_4$, filtered, and concentrated. Purification by column chromatography afforded (R)-(3-methyl-4-(1-phenylpyrido[3,4-d]pyridazin-4-yl)piperazin-1-yl)(morpholino)methanone 36. MS 418.2 (calc'd) 419.2 (M+H, found).

EXAMPLE 19

Preparation of (R)—N,3-dimethyl-N-phenyl-4-(1-phenylpyrido[3,4-d]pyridazin-4-yl)piperazine-1-carboxamide

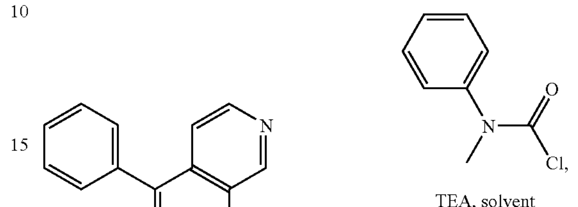

16

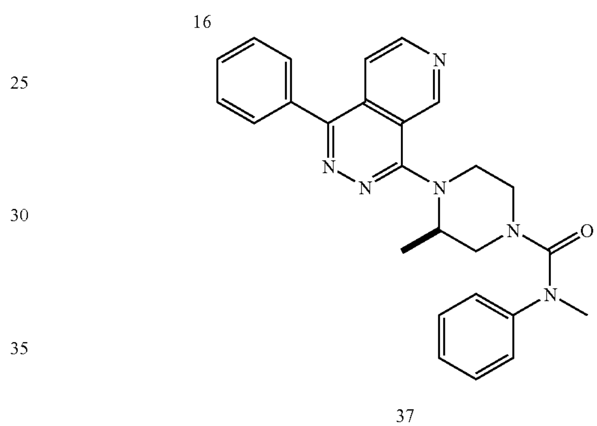

37

Using methods described in Example 18, and starting with (R)-4-(2-methylpiperazin-1-yl)-1-phenylpyrido[3,4-d]pyridazine 16 (100 mg, 327 μmol), triethylamine (91.3 μl, 655 μmol), and n-methyl-n-phenylcarbamoyl chloride (69.4 mg, 409 μmol) afforded (R)—N,3-dimethyl-N-phenyl-4-(1-phenylpyrido[3,4-d]pyridazin-4-yl)piperazine-1-carboxamide 37. MS 438.2 (calc'd) 439.1 (M+H, found)

EXAMPLE 20

Preparation of (R)-(3-methyl-4-(1-phenylpyrido[3,4-d]pyridazin-4-yl)piperazin-1-yl)(piperidin-1-yl)methanone

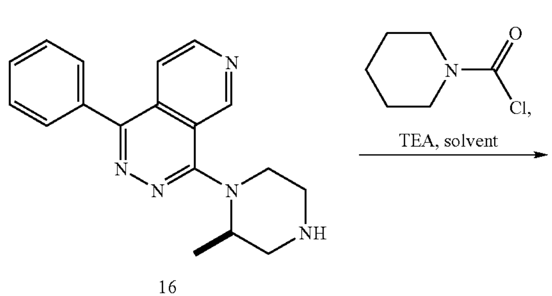

16

-continued

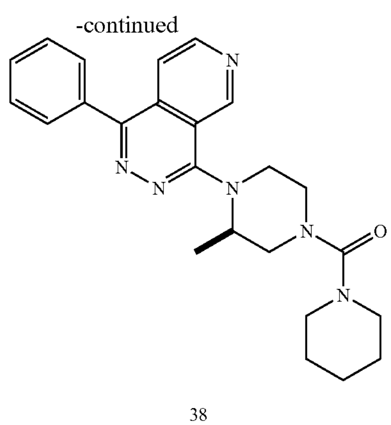

38

Using methods described in Example 18, and starting with (R)-4-(2-methylpiperazin-1-yl)-1-phenylpyrido[4,3-d]pyridazine 16 (125 mg, 409 μmol, triethylamine (80 μl, 614 μmol), and piperidine-1-carbonyl chloride (67 μl, 532 μmol) afforded (R)-(3-methyl-4-(1-phenylpyrido[4,3-d]pyridazin-4-yl)piperazin-1-yl)(piperidin-1-yl)methanone 38. MS 416.2 (calc'd) 417.3 (M+H, found).

EXAMPLE 21

Preparation of (R)—N,N,3-trimethyl-4-(1-phenylpyrido[3,4-d]pyridazin-4-yl)piperazine-1-carboxamide

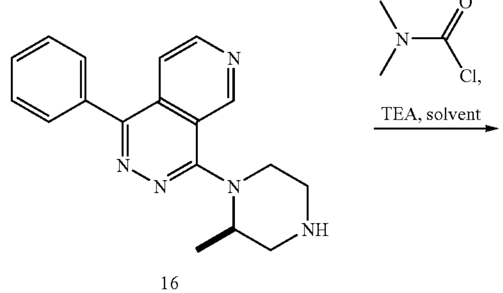

16

39

Using methods described in Example 18, and starting with (R)-4-(2-methylpiperazin-1-yl)-1-phenylpyrido[4,3-d]pyridazine 16 (125 mg, 409 μmol), triethylamine (86 μl, 614 μmol) and N,N-dimethylcarbamoyl chloride (41 μl, 450 μmol) afforded (R)—N,N,3-trimethyl-4-(1-phenylpyrido[4,3-d]pyridazin-4-yl)piperazine-1-carboxamide 39. MS 376.2 (calc'd) 377.2 (M+H, found).

EXAMPLE 22

Preparation of (R)-(4,4-difluoropiperidin-1-yl)(3-methyl-4-(1-phenylpyrido[3,4-d]pyridazin-4-yl)piperazin-1-yl)methanone

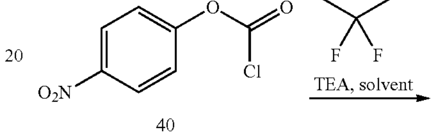

40

41

Step 1. To a solution of 4,4-difluoropiperidin hydrochloride (2.15 g, 14 mmol) in 30 mL of dichloromethane was added triethylamine (5.7 ml, 41 mmol), followed by 4-nitrophenyl chloroformate 40 (3.0 g, 15 mmol). After 1 h, the reaction was diluted with ethyl acetate and was washed with 3×30 mL of sat. $NaHCO_3$, and 1×30 mL brine. The organic layer was dried over MgSO4, filtered, and concentrated to afford 4-nitrophenyl 4,4-difluoropiperidin-1-carboxylate 41 (3.9 g, 100% yield). $^1$H-NMR (400 MHz, $CDCl_3$): δ 8.26 (m, 2H), 7.30 (m, 2H), 3.76 (m, 4H), 2.09 (m, 4H). MS 286.1 (calc'd) 287.1 (M+H, found).

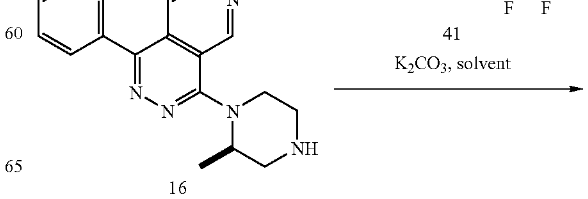

16

-continued

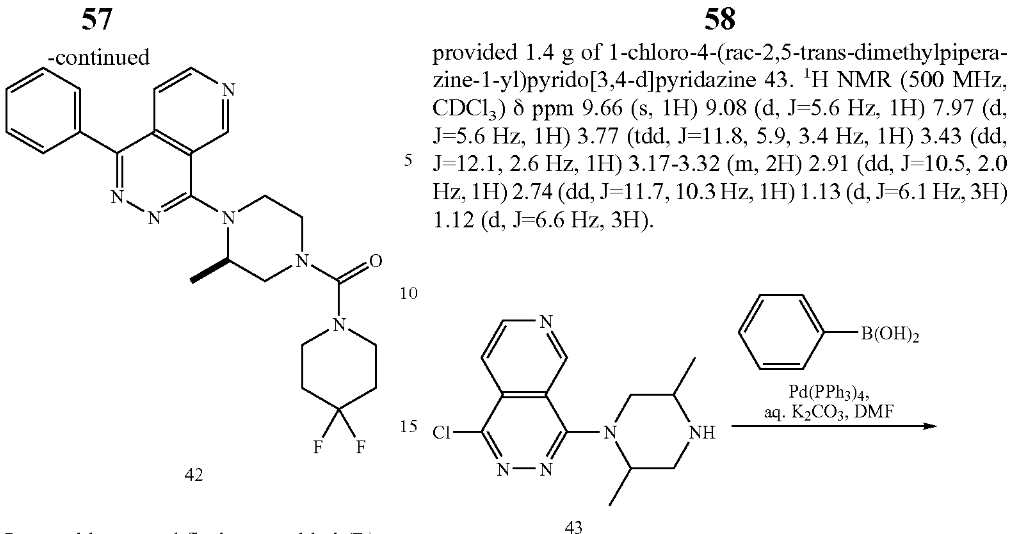

Step 2. To a 10 mL round bottomed flask was added (R)-4-(2-methylpiperazin-1-yl)-1-phenylpyrido[3,4-d]pyridazine 16 (110 mg, 360 μmol), 4-nitrophenyl 4,4-difluoropiperidin-1-carboxylate (124 mg, 432 μmol), and potassium carbonate (100 mg, 720 μmol). The reaction was heated to 80° C. overnight. After cooling to room temperature, the solvent was removed under vacuum, and the residue was redissolved in ethyl acetate and washed with water (10 mL), followed by $NaHCO_3$ (10 mL) and brine (10 mL). The organic layer was dried over $MgSO_4$, filtered, and concentrated. Purification by column chromatography afforded (R)-(4,4-difluoropiperidin-1-yl)(3-methyl-4-(1-phenylpyrido[3,4-d]pyridazin-4-yl)piperazin-1-yl)methanone 42. MS 452.2 (calc'd) 453.3 (M+H, found).

EXAMPLE 23

Preparation of (4,4-difluorocyclohexyl)((2S,5R)-2,5-dimethyl-4-(1-phenylpyrido[3,4-d]pyridazin-4-yl)piperazin-1-yl)methanone

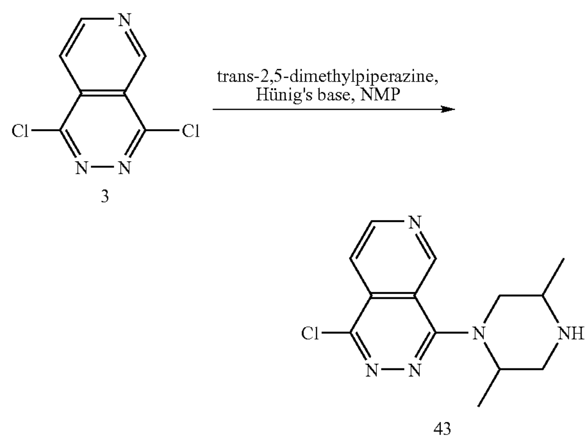

Step 1. To 1,4-dichloropyrido[3,4-d]pyridazine 3 (4.80 g, 24.0 mmol) and Hünig's Base (14.7 ml, 84.0 mmol) in NMP (10 ml) was added (2R,5S)-2,5-dimethylpiperazine (4.11 g, 36.0 mmol). The reaction was stirred at 100° C. After 2 h, the reaction contents were poured into saturated sodium bicarbonate (10× volume) and extracted with dichloromethane (4×50 mL). Silica gel chromatography (gradient 0 to 2.5% MeOH in 30% EtOAc in $CH_2Cl_2$ with 2.5% TEA additive) provided 1.4 g of 1-chloro-4-(rac-2,5-trans-dimethylpiperazine-1-yl)pyrido[3,4-d]pyridazine 43. $^1$H NMR (500 MHz, $CDCl_3$) δ ppm 9.66 (s, 1H) 9.08 (d, J=5.6 Hz, 1H) 7.97 (d, J=5.6 Hz, 1H) 3.77 (tdd, J=11.8, 5.9, 3.4 Hz, 1H) 3.43 (dd, J=12.1, 2.6 Hz, 1H) 3.17-3.32 (m, 2H) 2.91 (dd, J=10.5, 2.0 Hz, 1H) 2.74 (dd, J=11.7, 10.3 Hz, 1H) 1.13 (d, J=6.1 Hz, 3H) 1.12 (d, J=6.6 Hz, 3H).

44

Step 2. Tetrakis(triphenylphosphine)palladium (146 mg, 126 μmol), phenylboronic acid (461 mg, 3.78 mmol), 2 M sodium carbonate (2520 μl, 5.04 mmol), and 1-chloro-4-(trans-2,5-dimethylpiperazine-1-yl)pyrido[3,4-d]pyridazine 43 (700 mg, 2.52 mmol) were added to a round bottom flask. The reaction vessel was purged with nitrogen and toluene (25 mL) was added. The reaction was heated to 100° C. overnight. After cooling to RT, the reaction was diluted with 250 mL of ethyl acetate and washed with 1×50 mL of sat. $NaHCO_3$ and 1×50 mL of brine. The organic layer was dried over $MgSO_4$, filtered, and concentrated. Purification by column chromatography (10:0.5:0.1 $CH_2Cl_2$:MeOH, $Et_3N$) afforded racemic 4-(trans-2,5-dimethylpiperazine-1-yl)-1-phenylpyrido[3,4-d]pyridazine 44 (750 mg, 93% yield). $^1$H-NMR (400 MHz, $CDCl_3$): δ 9.76 (d, J=1.2 Hz, 1H), 8.94 (d, J=5.5 Hz, 1H), 7.84 (dd, J=5.9, 1.2 Hz, 1H), 7.78 (m, 2H), 7.57 (m, 2H), 3.83 (dqd, J=10.2, 5.9, 3.1 Hz, 1H), 3.47 (dd, J=12.1, 2.7 Hz, 1H), 3.30 (dqd, J=9.8, 6.3, 2.7 Hz, 1H), 3.25 (dd, J=12.5, 3.1 Hz, 1H), 2.94 (dq J=12.1, 10.2 Hz, 1H), 2.73 (dd, J=12.1, 9.8 Hz, 1H), 1.17 (d, J=6.3 Hz, 1H), 1.11 (d, J=6.6 Hz, 1H). MS 319.2 (calc'd) 320.2 (M+H, found).

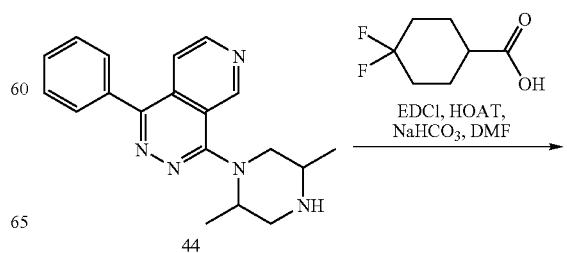

-continued

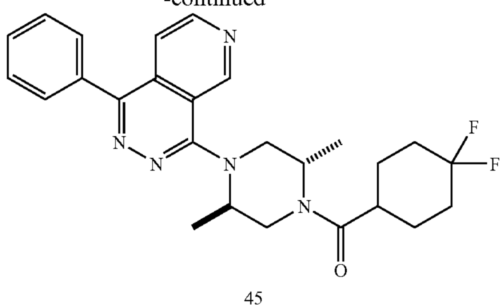

45

Step 3. To racemic trans 4-(2,5-dimethylpiperazine-1-yl)-1-phenylpyrido[3,4-d]pyridazine 44 (360 mg, 1127 μmol) dissolved in 4 mL of DMF was added EDCI (259 mg, 1.35 mmol), 4,4-difluorocyclohexanecarboxylic acid (204 mg, 1.24 mmol), 3H-[1,2,3]triazolo[4,5-b]pyridin-3-ol (184 mg, 1.35 mmol) (HOAT), and sodium carbonate (239 mg, 2.25 mmol). The reaction was stirred at RT for 4 h, and the solvent was removed in vacuo. The crude reaction mixture was dissolved in 100 mL of ethyl acetate and washed with 1×25 mL of water, 1×25 mL of sat. $NaHCO_3$, and 1×25 mL of brine. The organic layer was dried over $MgSO_4$, filtered, and concentrated. Purified by column chromatography to isolate racemic (4,4-difluorocyclohexyl)(trans-2,5-dimethyl-4-(1-phenylpyrido[3,4-d]pyridazin-4-yl)piperazin-1-yl)methanone 45. MS 465.2 (calc'd) 466.1 (M+H, found).

EXAMPLE 24

Preparation of (4,4-difluorocyclohexyl)((2R,5S)-2,5-dimethyl-4-(1-phenylpyrido[3,4-d]pyridazin-4-yl)piperazin-1-yl)methanone

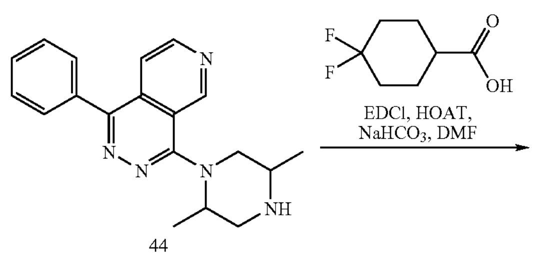

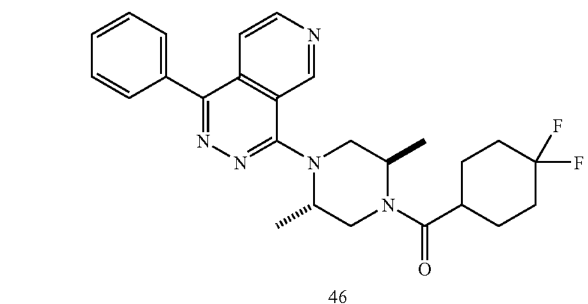

46

Isolated from chiral SFC chromatography as described in Example 23. MS 465.2 (calc'd) 466.1 (M+H, found).

EXAMPLE 25

Preparation of (S)-(4,4-difluoropiperidin-1-yl)(2-methyl-4-(1-(4-(trifluoromethyl)phenyl)pyrido[3,4-d]pyridazin-4-yl)piperazin-1-yl)methanone

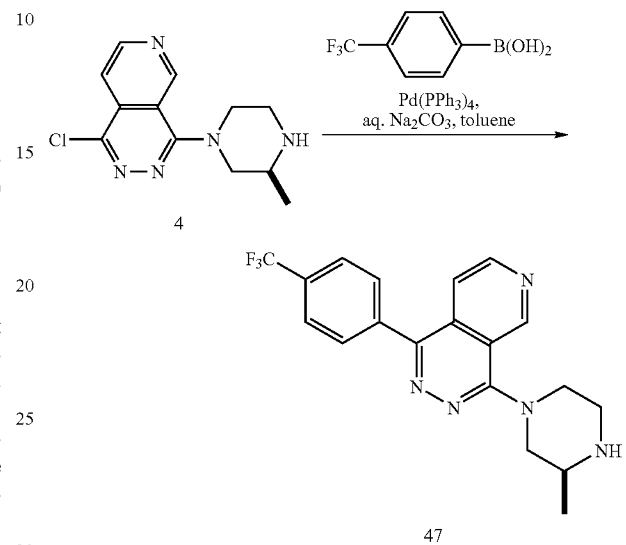

Step 1. To a round bottomed flask was added (S)-1-chloro-4-(3-methylpiperazin-1-yl)pyrido[3,4-d]pyridazine 4 (155 mg, 588 μmol), 4-trifluoromethylphenylboronic acid (167 mg, 882 μmol), tetrakis(triphenylphosphine)palladium (34 mg, 29 μmol), and 2 M aqueous sodium carbonate (588 μl, 1.18 mmol). Toluene (5.9 mL) was added and the reaction was heated to 100° C. After 16 h, the reaction was cooled to RT and diluted with ethyl acetate (70 mL). The organic layer was washed with 1×10 mL of sat. $NaHCO_3$, 1×10 mL of brine. The organic layer was dried over $MgSO_4$, filtered, and concentrated. Purification by column chromatography (10:0.5:0.1) ($CH_2Cl_2$:MeOH:$Et_3N$) afforded (S)-4-(3-methylpiperazin-1-yl)-1-(4-(trifluoromethyl)phenyl)pyrido[3,4-d]pyridazine 47 (154 mg, 70% yield). $^1$H-NMR (400 MHz, $CDCl_3$): δ 9.55 (d, J=0.8 Hz, 1H), 8.90 (d, J=5.5 Hz, 1H), 7.86 (m, 4H), 7.73 (dd, J=5.5, 0.8 Hz, 1H), 4.09 (m, 2H), 3.37 (ddd, J=12.5, 11.0, 3.5 Hz, 1H), 2.23 (m, 3H), 2.99 (dd, J=12.5, 10.2 Hz, 1H), 2.85 (br s, 1H), 1.17 (d, J=6.3 Hz, 1H). MS 373.1 (calc'd) 374.0 (M+H, found).

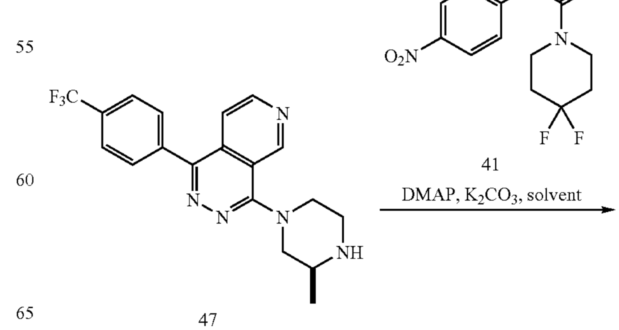

-continued

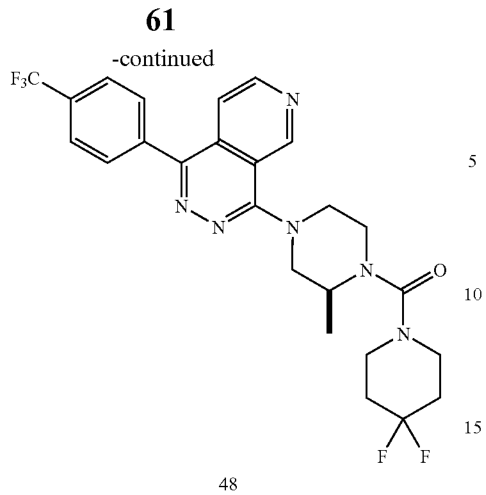

48

Step 2. DMF (3 mL) was added to (S)-4-(3-methylpiperazin-1-yl)-1-(4-(trifluoromethyl)phenyl)pyrido[3,4-d]pyridazine 47 (150 mg, 402 μmol), 4-nitrophenyl 4,4-difluoropiperidin-1-carboxylate 41 (230 mg, 803 μmol), potassium carbonate (167 mg, 1.2 mmol), 4-dimethylaminopyridine (9.8 mg, 80 μmol). The reaction was heated to 75° C. for 72 h. The reaction was diluted with ethyl acetate (70 mL) and washed with 1×10 mL water, 1×10 mL $NaHCO_3$, and 1×10 mL brine. The organic layer was dried over $MgSO_4$, filtered, and concentrated. Purification by column chromatography afforded (S)-(4,4-difluoropiperidin-1-yl)(2-methyl-4-(1-(4-(trifluoromethyl)phenyl)pyrido[3,4-d]pyridazin-4-yl)piperazin-1-yl)methanone 48. MS 520.2 (calc'd) 521.2 (M+H, found).

EXAMPLE 26

Preparation of (S)-methyl (4-(4-(4-(4,4-difluorocyclohexanecarbonyl)-3-methylpiperazin-1-yl)pyrido[3,4-d]pyridazin-1-yl)phenyl)methylcarbamate

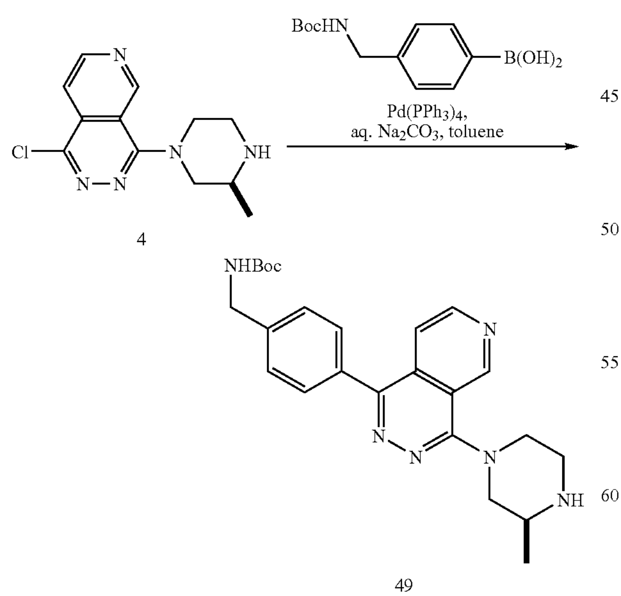

Step 1. Using methods described in Example 1 starting with (S)-1-chloro-4-(3-methylpiperazin-1-yl)pyrido[3,4-d]pyridazine 4 and 4-((tert-butoxycarbonyl)-methyl)phenylboronic acid, (S)-tert-butyl 4-(4-(3-methylpiperazin-1-yl)pyrido[3,4-d]pyridazin-1-yl)benzylcarbamate 49 was prepared. LC/MS m/z=435 (M+H$^+$).

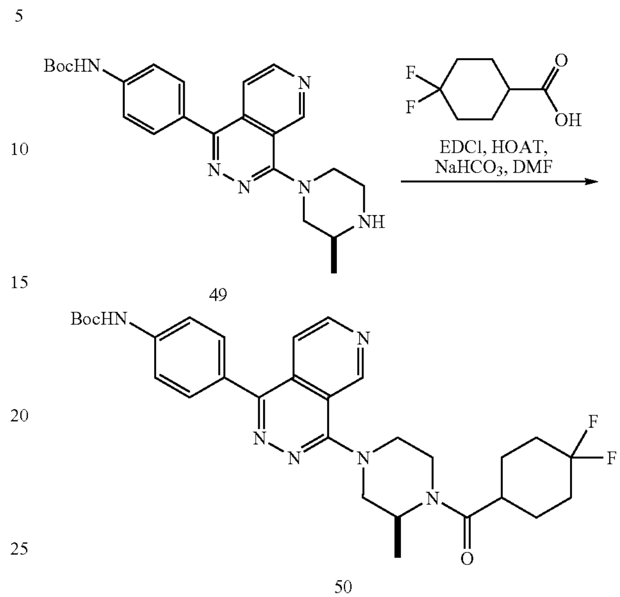

Step 2. Using methods described in Example 7 starting with 4-(4-(3-methylpiperazin-1-yl)pyrido[3,4-d]pyridazin-1-yl)benzylcarbamate 49 and 4,4-difluorocyclohexanecarboxylic acid, 4-(4-(4-(4,4-difluorocyclohexanecarbonyl)-3-methylpiperazin-1-yl)pyrido[3,4-d]pyridazin-1-yl) benzylcarbamate 50 was prepared. LC/MS m/z=581 (M+H$^+$).

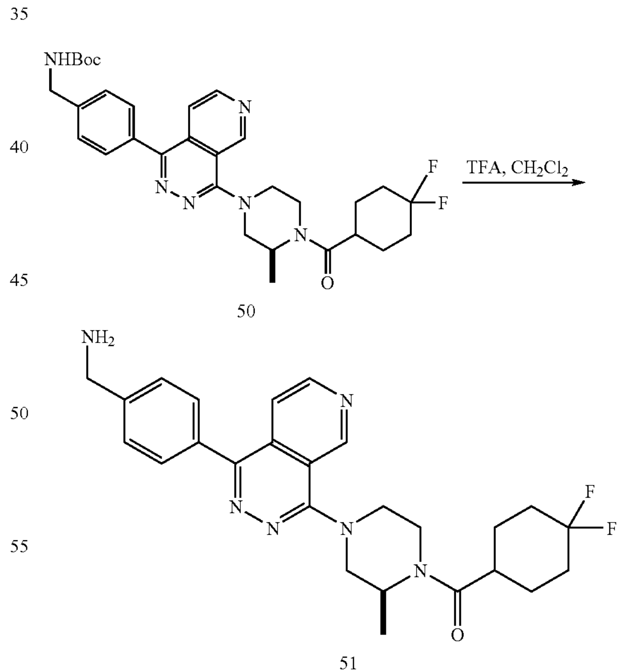

Step 3. (S)-tert-butyl 4-(4-(4-(4,4-difluorocyclohexanecarbonyl)-3-methylpiperazin-1-yl)pyrido[3,4-d]pyridazin-1-yl)benzylcarbamate 50 (588 mg, 1.01 mmol) was dissolved in dichloromethane (25 ml). Trifluoroacetic acid (1.56 ml, 2.02 mmol) was added and the reaction stirred at RT for three hours. The reaction was added carefully to saturated $NaHCO_3$ (80 ml) and extracted three times with dichloromethane (50 ml). The combined organic extracts were dried ($MgSO_4$) and evaporated to give 51 as a yellow solid, 444 mg (91% of theoretical). LC/MS m/z=481 (M+H$^+$).

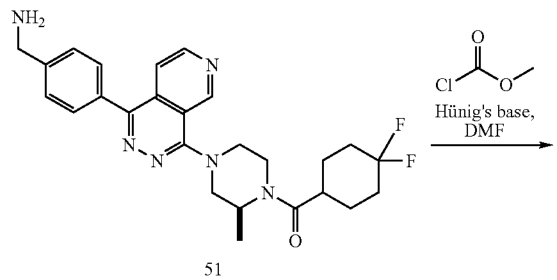

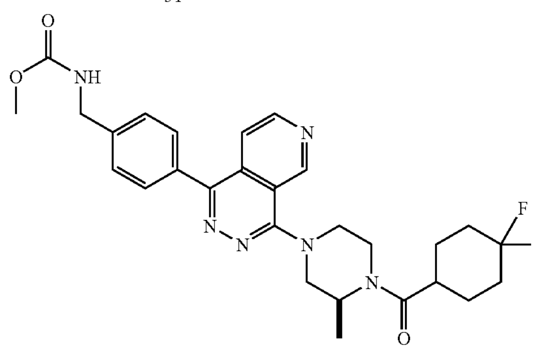

Step 4. (S)-(4-(1-(4-(aminomethyl)phenyl)pyrido[3,4-d]pyridazin-4-yl)-2-methylpiperazin-1-yl)(4,4-difluorocyclohexyl)methanone 51 (120 mg, 250 μmol) was dissolved in DMF (3 ml) and N,N-diisopropylethylamine (0.300 ml, 1.72 mmol). Methyl chloroformate (0.0211 ml, 275 μmol) was added and the reaction stirred at RT for 2 hours. The reaction was the taken up in ethyl acetate (80 ml) and washed with aqueous $K_2CO_3$ (10%), water, and brine. The organic phase was dried ($MgSO_4$) and evaporated to give an orange oil. The residue was chromatographed over silica with a gradient of dichloromethane with 2.5% triethylamine and 0-5% methanol. The product (S)-methyl (4-(4-(4-(4,4-difluorocyclohexanecarbonyl)-3-methylpiperazin-1-yl)pyrido[3,4-d]pyridazin-1-yl)phenyl)methylcarbamate 52 was isolated as a yellow solid. LC/MS m/z=539 (M+H$^+$).

EXAMPLE 27

Preparation of (S)—N-((4-(4-(4-(4,4-difluorocyclohexanecarbonyl)-3-methylpiperazin-1-yl)pyrido[3,4-d]pyridazin-1-yl)phenyl)methyl)acetamide

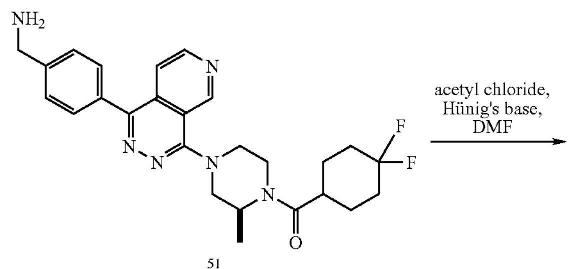

-continued

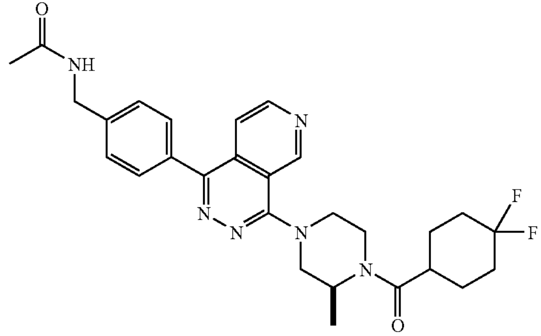

Using methods described in Example 26 starting with (S)-(4-(1-(4-(aminomethyl)phenyl)pyrido[3,4-d]pyridazin-4-yl)-2-methylpiperazin-1-yl)(4,4-difluorocyclohexyl)methanone 51 and acetyl chloride, (S)—N-((4-(4-(4-(4,4-difluorocyclohexanecarbonyl)-3-methylpiperazin-1-yl)pyrido[3,4-d]pyridazin-1-yl)phenyl)methyl)acetamide 53 was prepared. LC/MS m/z=523 (M+H$^+$).

EXAMPLE 28

Preparation of (S)-(4-(4-(4-(4,4-difluorocyclohexanecarbonyl)-3-methylpiperazin-1-yl)pyrido[3,4-d]pyridazin-1-yl)phenyl)methyl Carbamate

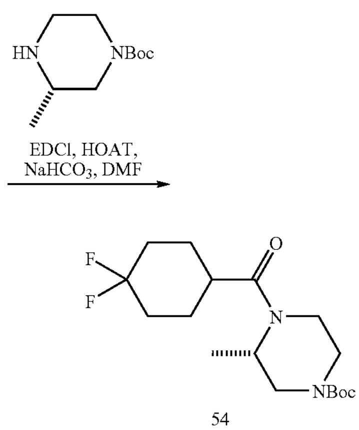

Step 1. 4,4-difluorocyclohexanecarboxylic acid, (S)-tert-butyl 3-methylpiperazine-1-carboxylate, N1-((ethylimino)methylene)-N3,N3-dimethylpropane-1,3-diamine hydrochloride (1.37 g, 7.13 mmol), 3H-[1,2,3]triazolo[4,5-b]pyridin-3-ol (0.970 g, 7.13 mmol), and sodium bicarbonate (0.998 g, 11.9 mmol) were stirred in DMF (20 ml) for 15 hours. The reaction was the taken up in ethyl acetate (80 ml) and washed with aqueous $K_2CO_3$ (10%), water, and brine. The organic phase was dried ($MgSO_4$) and evaporated to give an orange oil. The residue was chromatographed over silica with a gradient of hexane and 0-50% ethyl acetate. The product 54 was isolated as a white solid, 1.89 g (92% of theoretical).

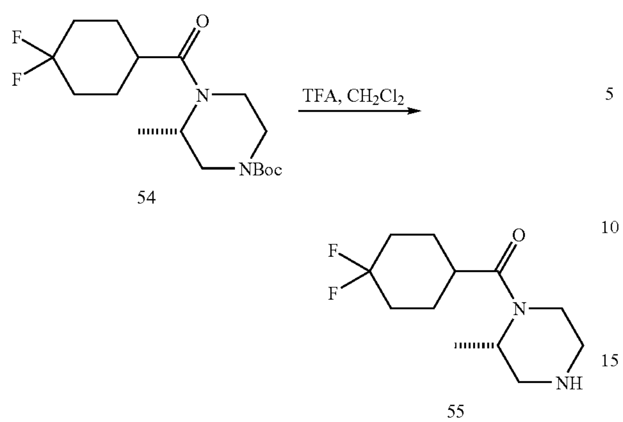

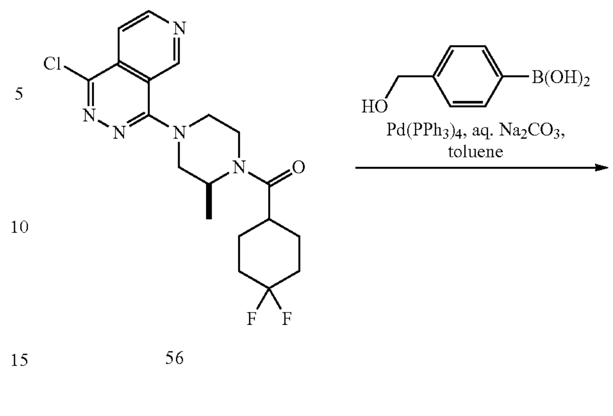

Step 2. (R)-tert-butyl 4-(4,4-difluorocyclohexanecarbonyl)-3-methylpiperazine-1-carboxylate 54 (1.89 g, 5.46 mmol) was dissolved in dichloromethane (30 ml). Trifluoroacetic acid (4.20 ml, 54.6 mmol) was added and the reaction stirred at RT for 1.5 hours. The reaction was added to aqueous $K_2CO_3$ (100 ml) and extracted three times with dichloromethane (50 ml). The combined organic extracts were dried ($MgSO_4$) and evaporated to give (S)-(4,4-difluorocyclohexyl)(2-methylpiperazin-1-yl)methanone 55 as a yellow oil, 1.35 g. LC/MS m/z=247 (M+H$^+$).

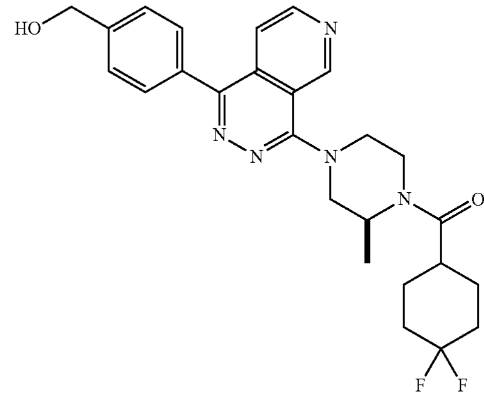

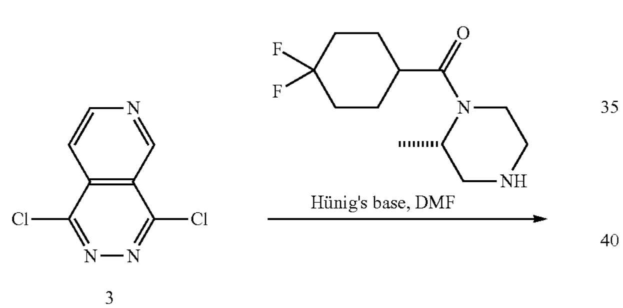

56

Step 3. Using methods described in Example 6 starting with 1,4-dichloropyrido[3,4-d]pyridazine 3 and (R)-(4,4-difluorocyclohexyl)(2-methylpiperazin-1-yl)methanone 55, (S)-(4-(1-chloropyrido[3,4-d]pyridazin-4-yl)-2-methylpiperazin-1-yl)(4,4-difluorocyclohexyl)methanone 56 was prepared.

Step 4. Using methods described in Example 1 starting with (S)-(4-(1-chloropyrido[3,4-d]pyridazin-4-yl)-2-methylpiperazin-1-yl)(4,4-difluorocyclohexyl)-methanone 56 and 4-(hydroxymethyl)phenylboronic acid, (S)-(4,4-difluorocyclohexyl)(4-(1-(4-(hydroxymethyl)phenyl)pyrido[3,4-d]pyridazin-4-yl)-2-methylpiperazin-1-yl)methanone 57 was prepared. The crude material was carried to the next step.

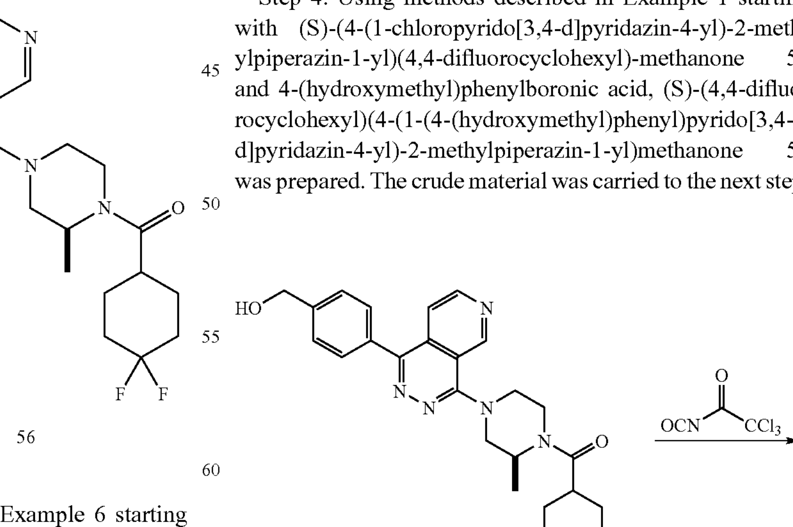

-continued

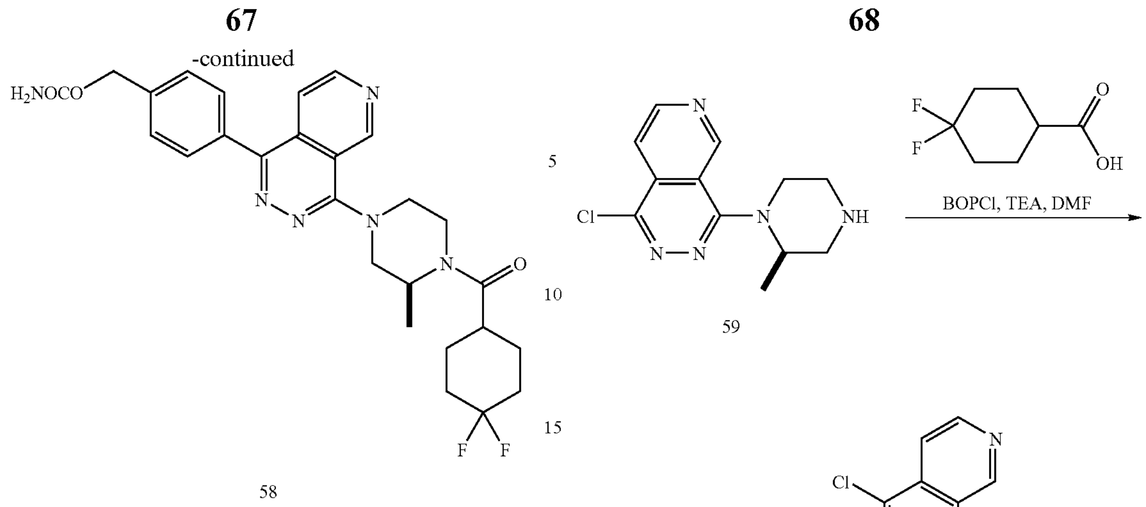

58

Step 5. Using methods described in Example 5 starting with (S)-(4,4-difluorocyclohexyl)(4-(1-(4-(hydroxymethyl)phenyl)pyrido[3,4-d]pyridazin-4-yl)-2-methylpiperazin-1-yl)methanone 57, (S)-(4-(4-(4-(4,4-difluorocyclohexanecarbonyl)-3-methylpiperazin-1-yl)pyrido[3,4-d]pyridazin-1-yl)phenyl)methyl carbamate 58 was prepared. LC/MS m/z=525 $(M+H^+)$

EXAMPLE 29

Preparation of (R)-(4,4-difluorocyclohexyl)(3-methyl-4-(1-(4-(trifluoromethyl)phenyl)pyrido[3,4-d]pyridazin-4-yl)piperazin-1-yl)methanone

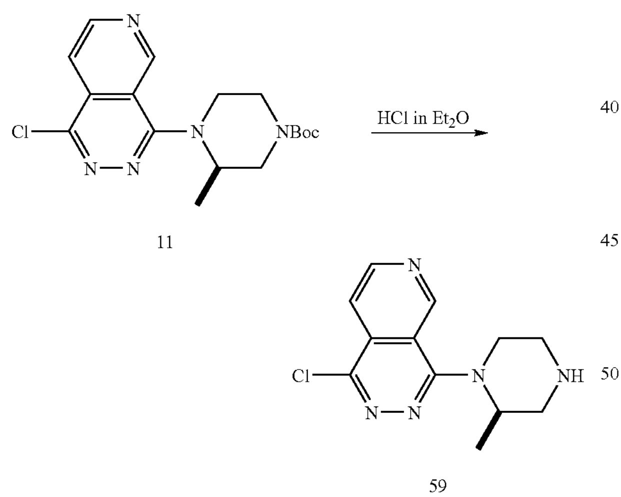

11

59

Step 1. (R)-tert-butyl 4-(1-chloropyrido[3,4-d]pyridazin-4-yl)-3-methylpiperazine-1-carboxylate 11 was suspended in diethyl ether (50 ml) and saturated with hydrogen chloride gas. The reaction was stirred at RT for about 2 hours, then the reaction contents were added carefully to 200 ml saturated $NaHCO_3$. The mixture was extracted four times with dichloromethane (100 ml) and one time with ethyl acetate (100 ml). Combined organics were dried ($MgSO_4$) and evaporated to give a yellow solid, 387 mg. The crude (R)-1-chloro-4-(2-methylpiperazin-1-yl)pyrido[3,4-d]pyridazine 59 was carried to the next step.

59

60

Step 2. 4,4-difluorocyclohexanecarboxylic acid (277 mg, 169 mmol) and bis(2-oxo-3-oxazolidinyl)phosphinic chloride (411 mg, 1.61 mmol) were stirred in DMF (3 ml) and triethylamine (0.4 ml) for 2 minutes. The solution was added to (R)-1-chloro-4-(2-methylpiperazin-1-yl)pyrido[3,4-d]pyridazine 59 (387 mg, 1.47 mmol) and washed in with an additional 1 ml DMF. The reaction was heated at 55° C. for 1.5 hours and then stirred at RT for 17 hours. The reaction was added to saturated $NaHCO_3$ (80 ml) and extracted three times with dichloromethane (50 ml). The combined organics were dried ($MgSO_4$) and evaporated to give a yellow solid. The residue was chromatographed over silica with a gradient of hexane and 0-100% ethyl acetate to give (R)-(4-(1-chloropyrido[3,4-d]pyridazin-4-yl)-3-methylpiperazin-1-yl)(4,4-difluorocyclohexyl)methanone 60 as a yellow solid, 236 mg. LC/MS m/z=410 $(M+H^+)$.

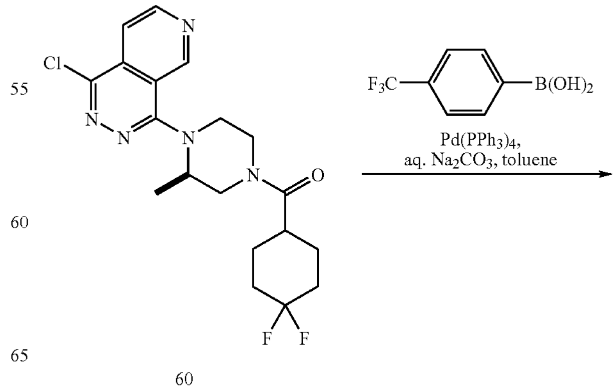

60

-continued

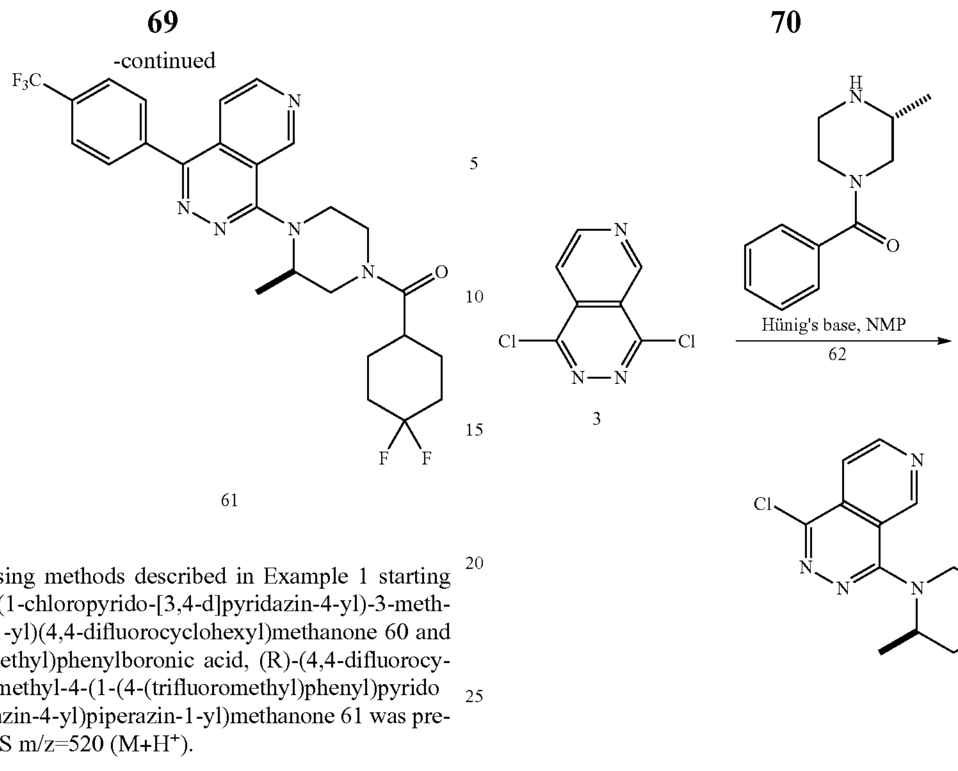

Step 3. Using methods described in Example 1 starting with (R)-(4-(1-chloropyrido-[3,4-d]pyridazin-4-yl)-3-methylpiperazin-1-yl)(4,4-difluorocyclohexyl)methanone 60 and 4-(trifluoromethyl)phenylboronic acid, (R)-(4,4-difluorocyclohexyl)(3-methyl-4-(1-(4-(trifluoromethyl)phenyl)pyrido[3,4-d]pyridazin-4-yl)piperazin-1-yl)methanone 61 was prepared. LC/MS m/z=520 (M+H$^+$).

EXAMPLE 30

Preparation of (R)-(3-methyl-4-(1-(4-(trifluoromethoxy)phenyl)pyrido[3,4-d]pyridazin-4-yl)piperazin-1-yl)(phenyl)methanone Step 2. Using methods described in Example 6 starting with 1,4-dichloropyrido[3,4-d]pyridazine 3 and (R)-(3-methylpiperazin-1-yl)(phenyl)methanone 62, (R)-(4-(1-chloropyrido[3,4-d]pyridazin-4-yl)-3-methylpiperazin-1-yl)(phenyl)methanone 63 was prepared. LC/MS m/z=368 (M+H$^+$).

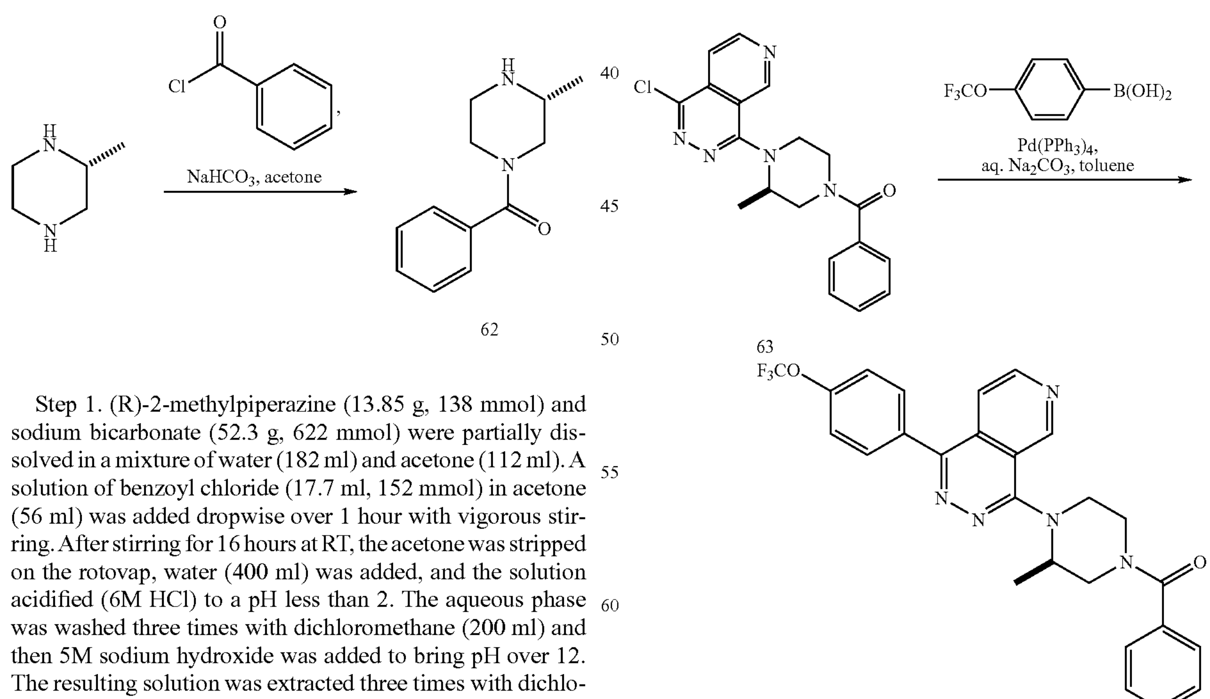

Step 1. (R)-2-methylpiperazine (13.85 g, 138 mmol) and sodium bicarbonate (52.3 g, 622 mmol) were partially dissolved in a mixture of water (182 ml) and acetone (112 ml). A solution of benzoyl chloride (17.7 ml, 152 mmol) in acetone (56 ml) was added dropwise over 1 hour with vigorous stirring. After stirring for 16 hours at RT, the acetone was stripped on the rotovap, water (400 ml) was added, and the solution acidified (6M HCl) to a pH less than 2. The aqueous phase was washed three times with dichloromethane (200 ml) and then 5M sodium hydroxide was added to bring pH over 12. The resulting solution was extracted three times with dichloromethane (200 ml), dried ($MgSO_4$) and evaporated to give (R)-(3-methylpiperazin-1-yl)(phenyl)methanone 62 as a yellow oil, 15.1 g (54% of theoretical). LC/MS m/z=205 (M+H$^+$).

Step 3. Using methods described in Example 1 starting with (R)-(4-(1-chloropyrido-[3,4-d]pyridazin-4-yl)-3-methylpiperazin-1-yl)(phenyl)methanone 63 and 4-(trifluoromethoxy)phenylboronic acid, (R)-(3-methyl-4-(1-(4-(trifluoromethoxy)phenyl)pyrido[3,4-d]pyridazin-4-yl)piperazin-1-yl)(phenyl)methanone 64 was prepared. LC/MS m/z=494 (M+H$^+$).

EXAMPLE 31

Preparation of (R)-4-(4-(4-(4,4-difluorocyclohexanecarbonyl)-2-methylpiperazin-1-yl)pyrido[3,4-d]pyridazin-1-yl)benzonitrile

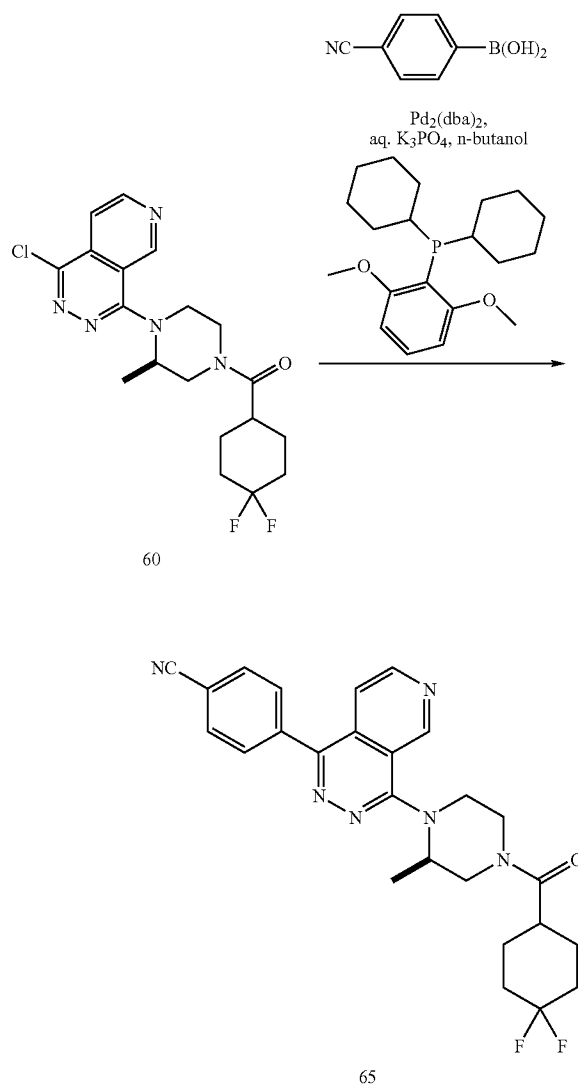

A 15 ml Schlenk tube was charged with (R)-(4-(1-chloropyrido[3,4-d]pyridazin-4-yl)-3-methylpiperazin-1-yl)(4,4-difluorocyclohexyl)methanone 60 (123 mg, 300 μmol), 4-cyanophenylboronic acid (66 mg, 450 μmol), tris(dibenzylideneacetone)-dipalladium (o) (5.5 mg, 6.0 μmol), dicyclohexyl(2,6-dimethoxyphenyl)phosphine (4.0 mg, 12 μmol), and potassium phosphate tribasic (127 mg, 600 μmol). The tube was evacuated and backfilled with argon 5 times and previously degassed n-butanol (1 ml) was added. The reaction was heated at 100° C. for 21 hours, then cooled and added to 30 ml aqueous $K_2CO_3$. This was extracted three times with dichloromethane (30 ml) and the combined extracts were dried ($MgSO_4$) and evaporated to give an orange oil. The residue was chromatographed over silica with a gradient of hexane with 2.5% triethylamine and 0-100% ethyl acetate with 2.5% triethylamine to give (R)-4-(4-(4-(4,4-difluorocyclohexanecarbonyl)-2-methylpiperazin-1-yl)pyrido[3,4-d]pyridazin-1-yl)benzonitrile 65 as a yellow solid. LC/MS m/z=477 (M+H$^+$).

EXAMPLE 32

Preparation of (R)-4-(4-(4-benzoyl-2-methylpiperazin-1-yl)pyrido[3,4-d]pyridazin-1-yl)benzonitrile

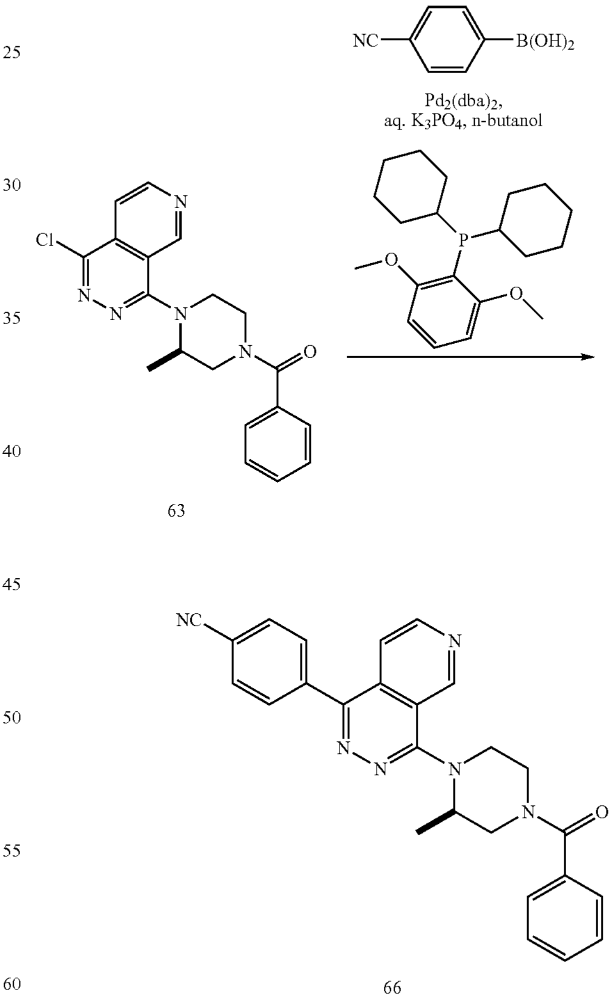

Using methods described in Example 31, and starting with (R)-(4-(1-chloropyrido[3,4-d]pyridazin-4-yl)-3-methylpiperazin-1-yl)(phenyl)methanone 63, (R)-4-(4-(4-benzoyl-2-methylpiperazin-1-yl)pyrido[3,4-d]pyridazin-1-yl)benzonitrile 66 was prepared. MS (calc'd) 434.2 (M+H, found) 435.1.

EXAMPLE 33

Preparation of (R)-4-(4-(4-benzoyl-2-methylpiperazin-1-yl)pyrido[3,4-d]pyridazin-1-yl)benzamide

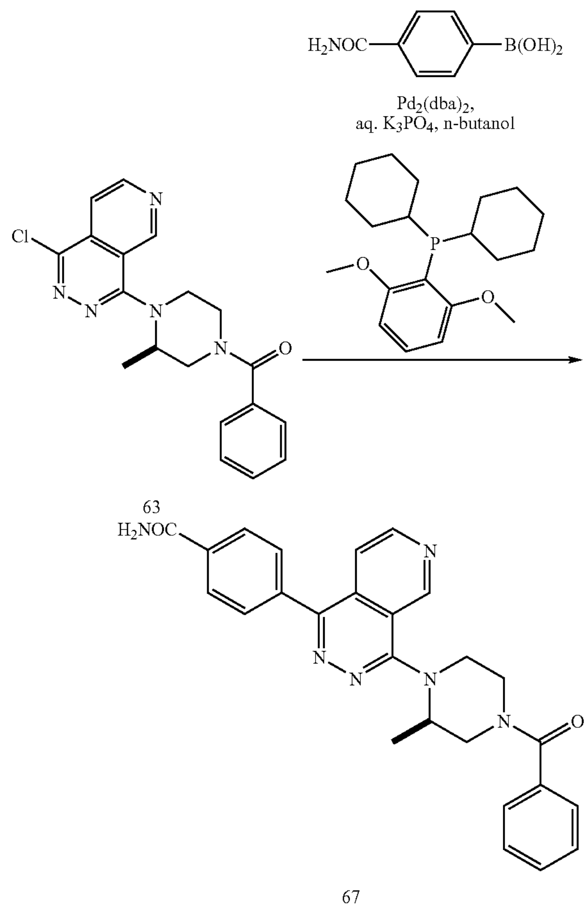

Using methods described in Example 31, and starting with (R)-(4-(1-chloropyrido[3,4-d]pyridazin-4-yl)-3-methylpiperazin-1-yl)(phenyl)methanone 63 and 4-carbamoylphenylboronic acid, (R)-4-(4-(4-benzoyl-2-methylpiperazin-1-yl)pyrido[3,4-d]pyridazin-1-yl)benzamide 67 was prepared. MS (calc'd) 452.2 (M+H, found) 452.1.

EXAMPLE 34

Preparation of (R)-(4-(1-(4-fluorophenyl)pyrido[3,4-d]pyridazin-4-yl)-3-methylpiperazin-1-yl)(phenyl)methanone

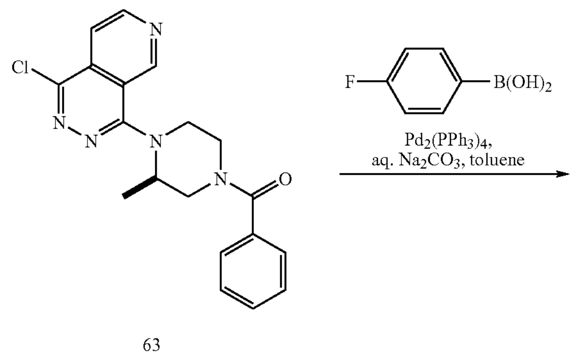

-continued

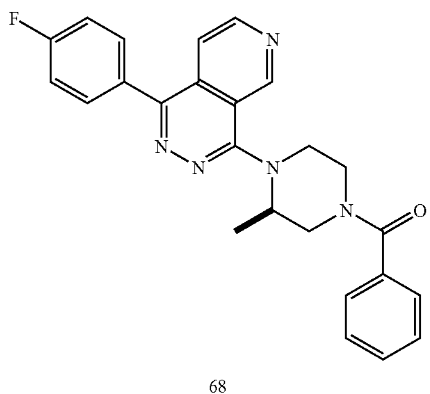

Using methods described in Example 1, and starting with (R)-(4-(1-chloropyrido[3,4-d]pyridazin-4-yl)-3-methylpiperazin-1-yl)(phenyl)methanone 63 and 4-fluorophenylboronic acid, (R)-(4-(1-(4-fluorophenyl)pyrido[3,4-d]pyridazin-4-yl)-3-methylpiperazin-1-yl)(phenyl)methanone 68 was prepared. MS (calc'd) 427.2 (M+H, found) 428.2.

EXAMPLE 35

Preparation of (R)-(4-(1-(4-(hydroxymethyl)phenyl)pyrido[3,4-d]pyridazin-4-yl)-3-methylpiperazin-1-yl)(phenyl)methanone

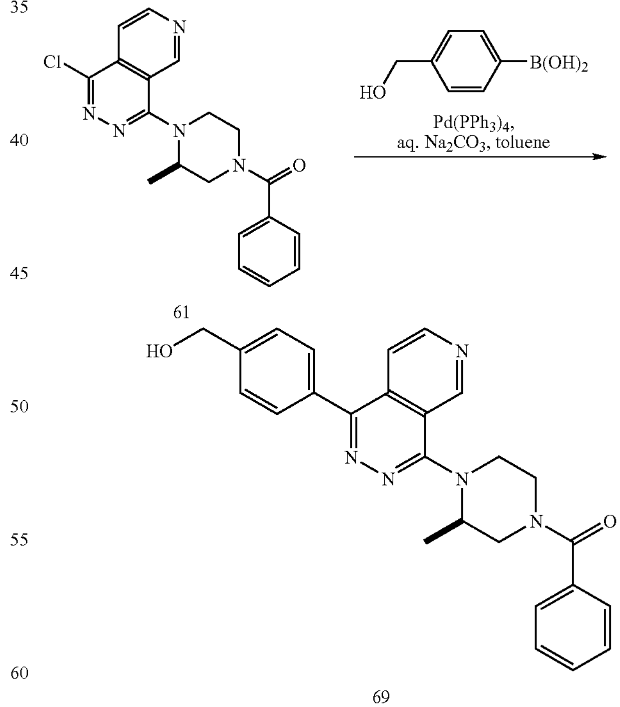

Using methods described in Example 1, and starting with (R)-(4-(1-chloropyrido[3,4-d]pyridazin-4-yl)-3-methylpiperazin-1-yl)(phenyl)methanone 63 and 4-(hydroxymethyl)phenylboronic acid, (R)-(4-(1-(4-(hydroxymethyl)phenyl)

pyrido[3,4-d]pyridazin-4-yl)-3-methylpiperazin-1-yl)(phenyl)methanone 69 was prepared. MS (calc'd) 439.2 (M+H, found) 440.2.

EXAMPLE 36

Preparation of (S)-(2-methyl-4-(5-phenylpyrido[2,3-d]pyridazin-8-yl)piperazin-1-yl)(phenyl)methanone

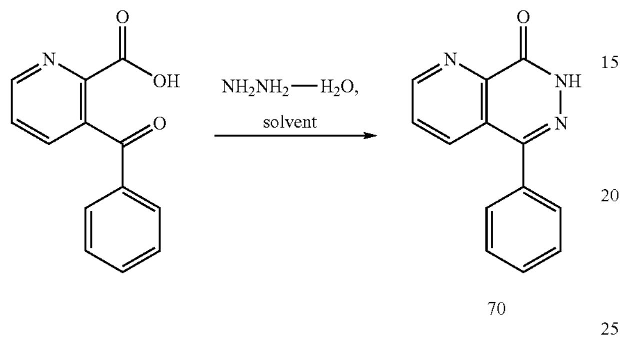

Step 1. To a round bottomed flask containing 3-benzoylpicolinic acid (2.00 g, 9 mmol) was added 50 mL of ethanol. Hydrazine hydrate (0.6 ml, 11 mmol) was added and the mixture was heated to reflux for 3 h. After cooling to rt, the solvent was removed in vacuo. The resulting yellow solid was recrystallized from 30 mL of boiling 1-propanol to afford 5-phenylpyrido[2,3-d]pyridazin-8(7H)-one 70 (1.4 g, 71% yield) as a white solid. $^1$H-NMR (400 MHz, $CDCl_3$): δ 10.55 (br s, 1H), 9.16 (dd, J=8.6, 1.6 Hz, 1H), 7.73 (dd, J=8.6, 4.7 Hz, 1H), 7.56 (m, 5H).

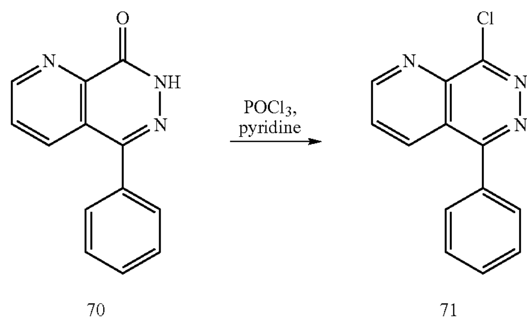

Step 2. To 5-phenylpyrido[2,3-d]pyridazin-8(7H)-one (1.39 g, 6.2 mmol) and pyridine (0.50 ml, 6.2 mmol) was added phosphorus oxychloride (12 ml, 125 mmol). The slurry was heated to 110° C. for 1 hour. After cooling to room temperature, the reaction was poured into 200 mL of ice-water. The mixture was extracted with 4×50 mL of chloroform. The chloroform layer was washed with 1×50 mL $H_2O$, 1×50 mL 1N NaOH, and 1×50 mL of $H_2O$. The organic layer was dried over $Na_2SO_4$, filtered, and concentrated. Silica gel column chromatography afforded 8-chloro-5-phenylpyrido[3,2-d]pyridazine 71 (1.2 g). $^1$H-NMR (400 MHz, $CDCl_3$): δ 9.42 (d, J=2.7 Hz, 1H), 8.45 (d, J=7.8 Hz, 1H), 7.89 (m, 1H), 7.73 (br s, 2H), 7.61 (br s, 3H). MS 241.0 (calc'd) 242.0 (M+H, found).

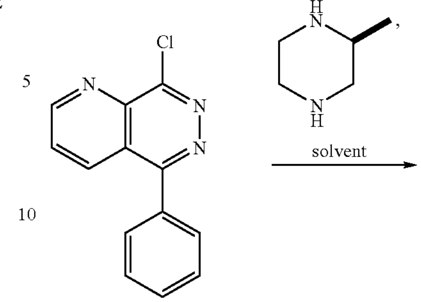

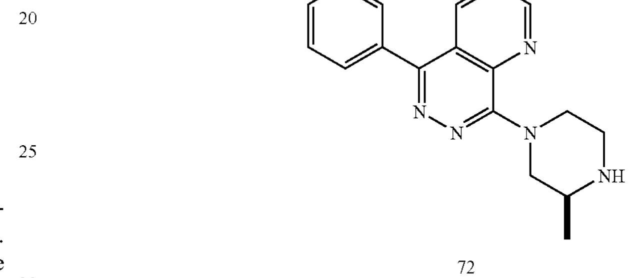

Step 3. In a 20 mL reaction vial was combined (S)-(+)-2-methylpiperazine (1252 mg, 12.5 mmol) and 8-chloro-5-phenylpyrido[3,2-d]pyridazine 71 (503.3 mg, 2 mmol). The solids were heated to melting and held at 130° C. for 1 h under $N_2$. After cooling to room temperature, the resulting solid was dissolved in 100 mL of $CH_2Cl_2$ and washed with 1×10 mL of sat. $NaHCO_3$, followed by 1×10 mL of brine. The combined organic layers were dried over $MgSO_4$, filtered and concentrated. The crude was carried on to the next step without purification. $^1$H-NMR (400 MHz, $CDCl_3$): δ 9.10 (dd, J=4.3, 1.6 Hz, 1H), 8.33 (dd, J=8.2, 1.6 Hz, 1H), 7.72 (m, 2H), 7.67 (dd, J=8.2, 4.3 Hz, 1H), 7.50 (m, 3H), 4.96 (dq, J=12.5, 2.7 Hz, 1H), 4.90 (dt, J=12.9, 2.7 Hz, 1H), 3.30-3.15 (series of m, 3H), 2.95 (dd, J=12.9, 10.6 Hz, 1H), 2.10 (br s, 1H), 1.20 (d, J=6.3 Hz, 3H). MS 305.2 306.1 (M+H, found).

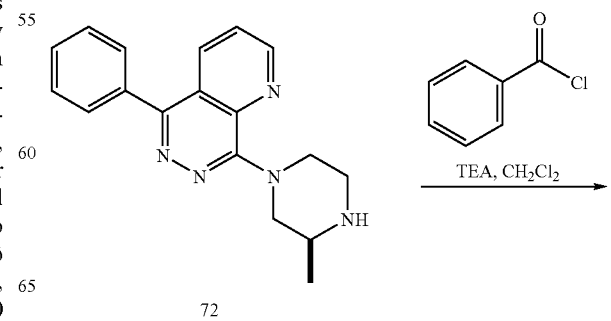

-continued

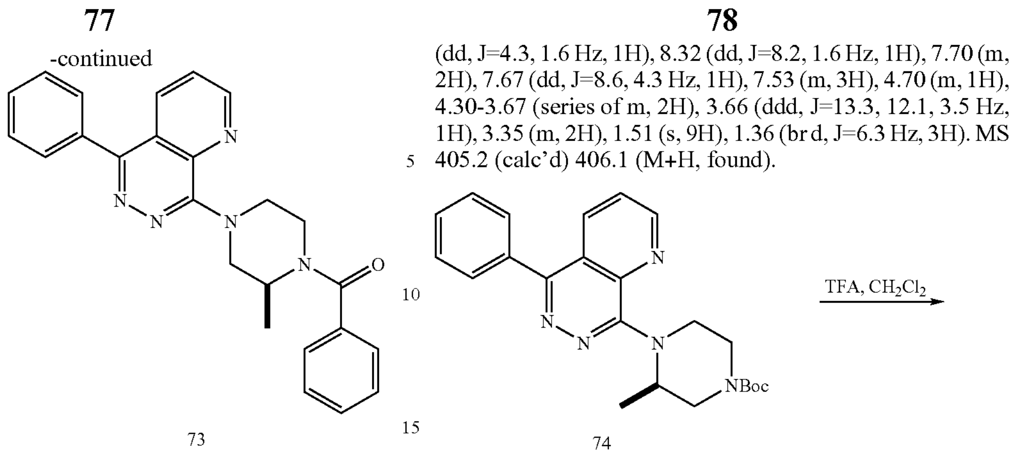

73

Step 4. Using methods described in Example 10, and starting with(S)-8-(3-methylpiperazin-1-yl)-5-phenylpyrido[3,2-d]pyridazine 72 (223 mg, 730 μmol), triethylamine (204 μl, 1460 μmol), and benzoyl chloride (102 μl, 876 μmol) afforded (S)-(2-methyl-4-(5-phenylpyrido[2,3-d]pyridazin-8-yl)piperazin-1-yl)(phenyl)methanone 73. MS 409.2 (calc'd) 410.2 (M+H, found).

EXAMPLE 37

Preparation of (R)-(3-methyl-4-(5-phenylpyrido[2,3-d]pyridazin-8-yl)piperazin-1-yl)(phenyl)methanone

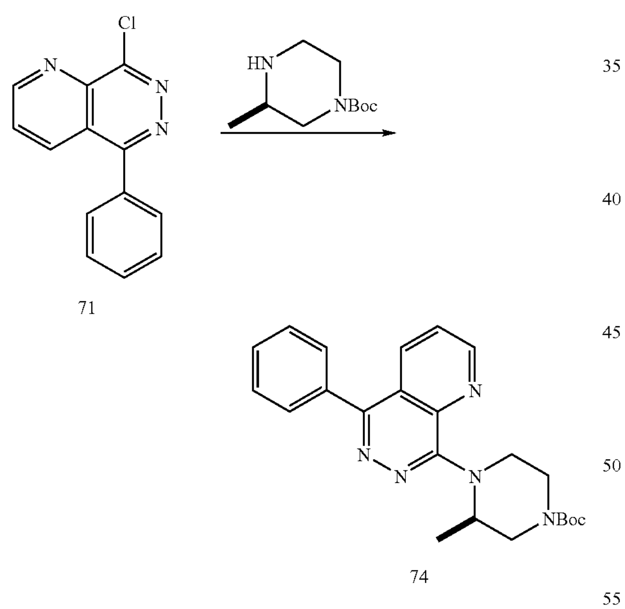

71

74

Step 1. 8-chloro-5-phenylpyrido[3,2-d]pyridazine 71 (374 mg, 1.548 mmol) and (R)-tert-butyl 3-methylpiperazine-1-carboxylate (1240 mg, 6.19 mmol) were combined in a reaction vial and heated to 130° C. for 3 h. After cooling to room temperature, the resulting solid was dissolved in 100 mL of $CH_2Cl_2$ and washed with 1×10 mL of saturated $NaHCO_3$, followed by 1×10 mL of brine. The combined organic layers were dried over $MgSO_4$, filtered and concentrated. Purification by column chromatography afforded pure (R)-tert-butyl 3-methyl-4-(5-phenylpyrido[3,2-d]pyridazin-8-yl)piperazine-1-carboxylate 74. $^1$H-NMR (400 MHz, $CDCl_3$): δ 9.08 (dd, J=4.3, 1.6 Hz, 1H), 8.32 (dd, J=8.2, 1.6 Hz, 1H), 7.70 (m, 2H), 7.67 (dd, J=8.6, 4.3 Hz, 1H), 7.53 (m, 3H), 4.70 (m, 1H), 4.30-3.67 (series of m, 2H), 3.66 (ddd, J=13.3, 12.1, 3.5 Hz, 1H), 3.35 (m, 2H), 1.51 (s, 9H), 1.36 (br d, J=6.3 Hz, 3H). MS 405.2 (calc'd) 406.1 (M+H, found).

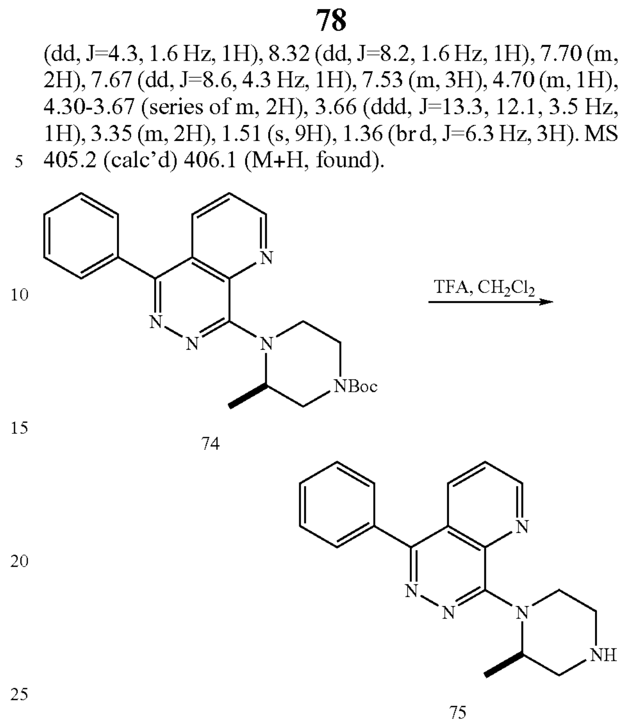

74

75

Step 2. Using methods described in Example 6, and starting with (R)-tert-butyl 3-methyl-4-(5-phenylpyrido[3,2-d]pyridazin-8-yl)piperazine-1-carboxylate 74 (325 mg, 801 μmol) and trifluoroacetic acid (3.09 ml, 40.1 mmol), yielded (R)-8-(2-methylpiperazin-1-yl)-5-phenylpyrido[3,2-d]pyridazine 75 (240 mg, 98.1% yield). $^1$H-NMR (400 MHz, $CDCl_3$): δ 9.07 (dd, J=4.3, 2.0 Hz, 1H), 8.31 (dd, J=8.6, 2.0 Hz, 1H), 7.72 (m, 2H), 7.64 (dd, J=8.6, 4.3 Hz, 1H), 7.52 (m, 3H), 5.38 (m, 1H), 4.60 (dt, J=13.3, 2.3 Hz, 1H), 3.64 (ddd, J=13.7, 10.6, 4.7 Hz, 1H), 3.31 (dd, J=12.5, 3.9 Hz, 1H), 3.15 (m, 2H), 2.95 (dd, J=12.5, 1.6 Hz, 1H), 1.43 (d, J=7.0 Hz, 1H). MS 305.2 306.1 (M+H, found).

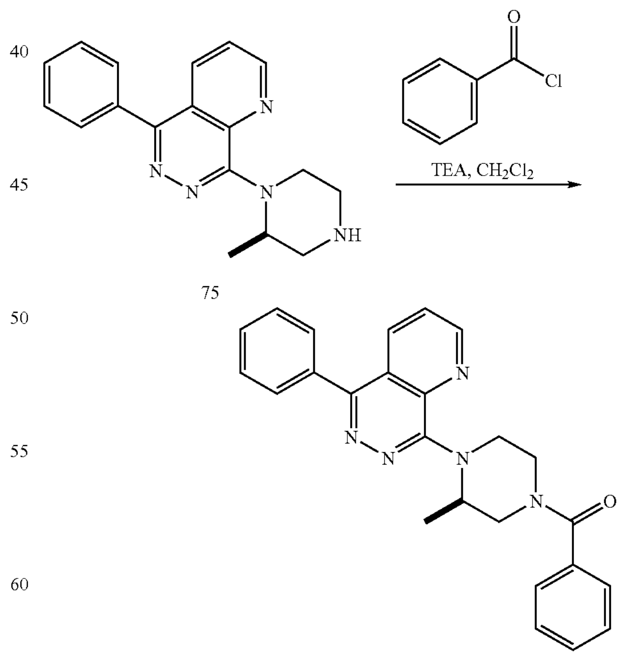

75

76

Step 3. Using methods described in Example 10 and starting with (R)-8-(2-methylpiperazin-1-yl)-5-phenylpyrido[3, 2-d]pyridazine 75 (245 mg, 802 μmol), triethylamine (224 μl, 1.60 mmol), and benzoyl chloride (116 μl, 1.00 mmol) afforded (R)-(3-methyl-4-(5-phenylpyrido[2,3-d]pyridazin-8-yl)piperazin-1-yl)(phenyl)methanone 76. MS 409.2 (calc'd) 410.2 (M+H, found).

EXAMPLE 38

Preparation of (R)-(3-methyl-4-(8-phenylpyrido[3,2-d]pyridazin-5-yl)piperazin-1-yl)(phenyl)methanone

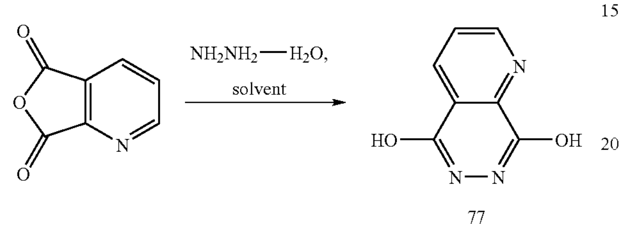

Step 1. To 25 mL of acetic acid at 100° C. was added 2,3-pyridinedicarboxylic anhydride (5.00 g, 34 mmol). Once the solution was homogeneous, it was removed from the oil bath and anhydrous hydrazine (2.0 ml, 64 mmol) was added dropwise over 5 minutes. The reaction was returned to reflux. After 3 min, the solution crystallized and became a solid mass. The reaction was heated in a 125° C. bath for 10 minutes then cooled to room temperature. The solid was transferred to a Büchner funnel and washed with 2×10 mL of acetic acid. The solid was dried under high vacuum to afford 6,7-dihydropyrido[2,3-d]pyridazine-5,8-dione 77. $^1$H-NMR (400 MHz, DMSO): δ 9.10 dd, J=4.7, 2.0 Hz, 1H), 8.50 (dd, J=7.8, 1.6 Hz, 1H), 7.86 (dd, J=8.2, 4.7 Hz, 1H).

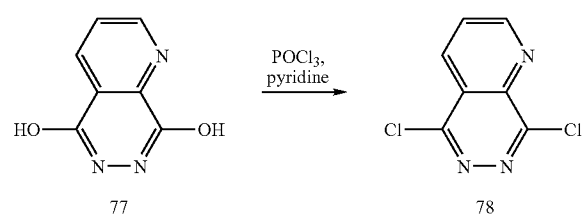

Step 2. Intermediate 77 (1.00 g, 6.1 mmol) and pyridine (0.97 g, 12.3 mmol) were slurried in phosphorus oxychloride (28.2 g, 184 mmol). The reaction was heated to 110° C. for 1 h, at which point the reflux condenser was switched to a distillation head and $POCl_3$ was removed at 100° C. under vacuum down to ~90% of the original volume. The resulting concentrated solution was quenched with 200 mL of ice-water. Chloroform (250 mL) was added and the organic layer was washed with 1×100 mL of $H_2O$, 1×50 mL 1N NaOH, and 1×100 mL $H_2O$. The organic layer was dried over $Na_2SO_4$, filtered, and concentrated. Purification by column chromatography (100% ether on 60 g silica gel) afforded 5,8-dichloropyrido[2,3-d]pyridazine 78. $^1$H-NMR (400 MHz, $CDCl_3$): δ 9.42 (dd, J=4.3, 1.6 Hz, 1H), 8.65 (dd, J=8.6, 1.6 Hz, 1H), 8.03 (J=8.2, 4.3 Hz, 1H). MS 199.0 (calc'd) 200.0 (M+H, found).

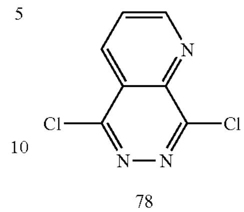

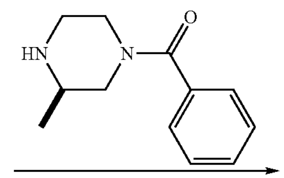

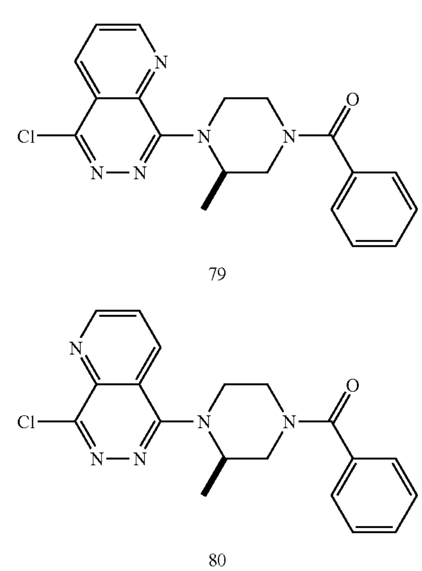

Step 3. To a reaction vial was added 5,8-dichloropyrido[2,3-d]pyridazine 78 (165 mg, 825 μmol) and (R)-(3-methylpiperazin-1-yl)(phenyl)methanone (337 mg, 1.65 mmol). The mixture was heated to 100° C. for 2 h. After cooling to room temperature, the resultant glassy product was dissolved in dichloromethane (40 mL) and washed with 1×5 mL $NaHCO_3$ and 1×5 mL of brine. The organic layer was dried over $MgSO_4$, filtered and concentrated. Purification by silica gel column chromatography using a gradient of 70% ethyl acetate in hexanes to 90% EtOAc in hexanes afforded the regioisomeric products. The first eluting product (R)-(4-(5-chloropyrido[2,3-d]pyridazin-8-yl)-3-methylpiperazin-1-yl)(phenyl)methanone 79 (132 mg, 44% yield) was the major product, the second eluting product (R)-(4-(8-chloropyrido[3,2-d]pyridazin-5-yl)-3-methylpiperazin-1-yl)(phenyl) methanone 80 (74 mg, 24% yield) was the minor product. Data for 79: $^1$H-NMR (400 MHz, $CDCl_3$): δ 9.10 (brs, 1H), 8.47 (dd, J=8.2, 1.6 Hz, 1H), 7.83 (dd, J=8.2, 4.3 Hz, 1H), 5.46 (br m, 1H), 4.97-4.40 (series of m, 2H), 3.99-3.20 (series of m, 4H), 1.40 (br m, 3H). MS 367.1 (calc'd) 368.0 (M+H, found). Data for (R)-(4-(8-chloropyrido[3,2-d]pyridazin-5-yl)-3-methylpiperazin-1-yl)(phenyl)methanone: $^1$H-NMR (400 MHz, $CDCl_3$): δ 9.27 (dd, J=4.3, 1.6, 1H), 8.39 (J=8.6, 1.6 Hz, 1H), 7.83 (dd, J=8.2, 4.3 Hz, 1H), 7.45 (s, 5H), 4.31 (br s, 1H), 4.11 (br s, 1H), 2.68 (m, 5H), 1.27 (br s, 3H). MS 367.1 (calc'd) 368.0 (M+H, found).

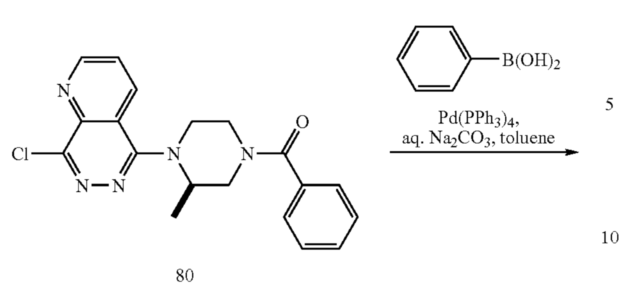

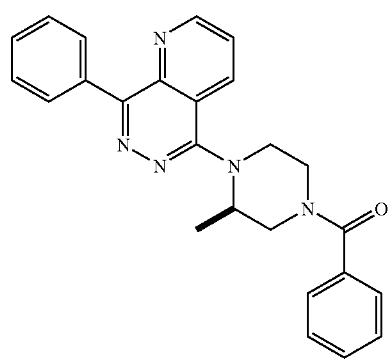

Step 4. Using methods described in Example 6, and starting with (R)-(4-(8-chloropyrido[3,2-d]pyridazin-5-yl)-3-methylpiperazin-1-yl)(phenyl)methanone 80 (68 mg, 185 μmol), tetrakis(triphenylphosphine)palladium (11 mg, 9 μmol), phenylboronic acid (34 mg, 277 μmol), and 2 M sodium carbonate (185 μl, 370 μmol) yielded (R)-(3-methyl-4-(8-phenylpyrido[3,2-d]pyridazin-5-yl)piperazin-1-yl)(phenyl)methanone 81 (58 mg, 77% yield) after chromatographic purification. MS 409.2 (calc'd) 410.2 (M+H, found).

EXAMPLE 39

Preparation of (R)-(4-(5-(4-(hydroxymethyl)phenyl)pyrido[2,3-d]pyridazin-8-yl)-3-methylpiperazin-1-yl)(phenyl)methanone

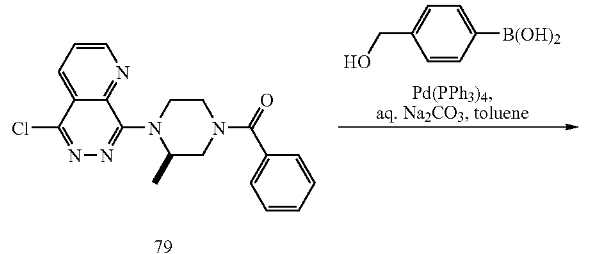

-continued

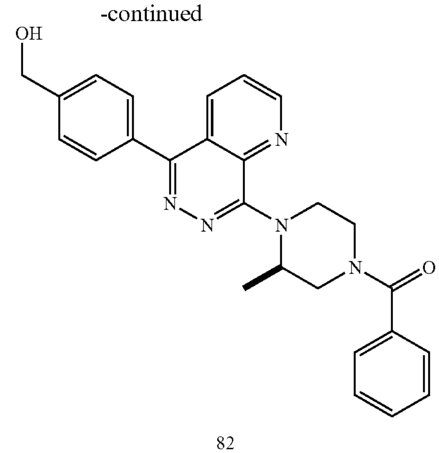

Using methods described in Example 6, and starting with (R)-(4-(5-chloropyrido[2,3-d]pyridazin-8-yl)-3-methylpiperazin-1-yl)(phenyl)methanone 79 (180 mg, 489 μmol), 4-(hydroxymethyl)phenylboronic acid (112 mg, 734 μmol), tetrakis(triphenylphosphine)palladium (28 mg, 24 μmol), and 2 M sodium carbonate (489 μl, 979 μmol) yielded (R)-(4-(5-(4-(hydroxymethyl)phenyl)pyrido[2,3-d]pyridazin-8-yl)-3-methylpiperazin-1-yl)(phenyl)methanone 82 (122 mg, 57% yield) after chromatographic purification. MS 439.2 (calc'd) 440.2 (M+H, found).

EXAMPLE 40

Preparation of ((R)-4-(5-(4-chloro-2-fluorophenyl)pyrido[2,3-d]pyridazin-8-yl)-3-methylpiperazin-1-yl)(phenyl)methanone

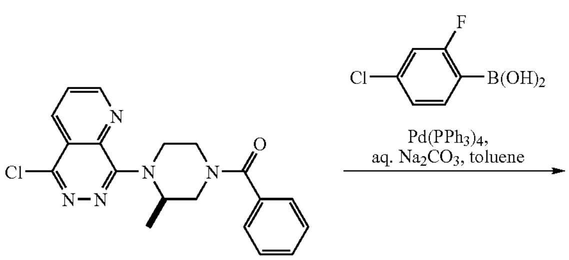

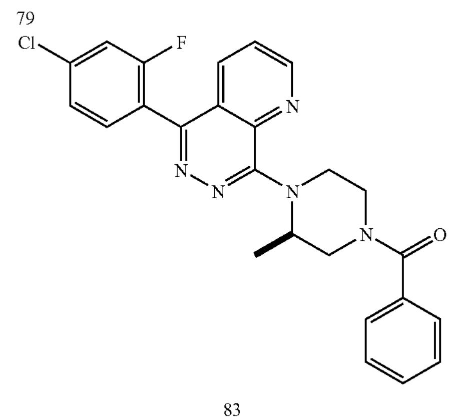

Using methods described in Example 6, and starting with (R)-(4-(5-chloropyrido[2,3-d]pyridazin-8-yl)-3-methylpiperazin-1-yl)(phenyl)methanone 79 (180 mg, 489 μmol), 4-chloro-2-fluorophenylboronic acid (128 mg, 734 μmol), tetrakis(triphenylphosphine)palladium (28 mg, 24 μmol), and 2 M sodium carbonate (489 μl, 979 μmol) afforded ((R)-4-(5-(4-chloro-2-fluorophenyl)pyrido[2,3-d]pyridazin-8-yl)-3-methylpiperazin-1-yl)(phenyl)methanone 83 after chromatographic purification. MS 461.1 (calc'd) 462.1 (M+H, found).

EXAMPLE 41

Preparation of (R)-(3-methyl-4-(5-(4-(trifluoromethyl)phenyl)pyrido[2,3-d]pyridazin-8-yl)piperazin-1-yl)(phenyl)methanone

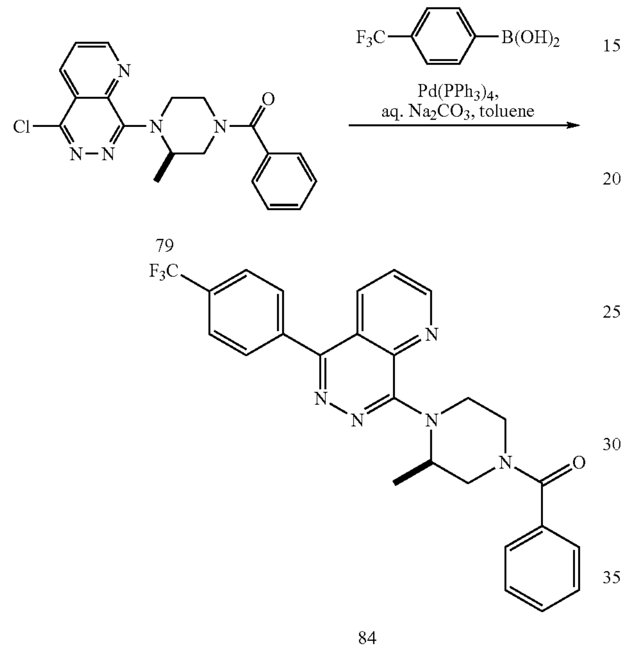

Using methods described in Example 6, and starting with (R)-(4-(5-chloropyrido[2,3-d]pyridazin-8-yl)-3-methylpiperazin-1-yl)(phenyl)methanone 79 (180 mg, 489 μmol), tetrakis(triphenylphosphine)palladium (283 mg, 245 μmol), 4-trifluoromethylphenylboronic acid (139 mg, 734 μmol), and 2 M sodium carbonate (489 μl, 979 μmol) afforded (R)-(3-methyl-4-(5-(4-(trifluoromethyl)phenyl)pyrido[2,3-d]pyridazin-8-yl)piperazin-1-yl)(phenyl)methanone 84 after chromatographic purification. MS 477.2 (calc'd) 478.1 (M+H, found).

EXAMPLE 42

Preparation of (R)-4-(8-(4-benzoyl-2-methylpiperazin-1-yl)pyrido[2,3-d]pyridazin-5-yl)benzonitrile

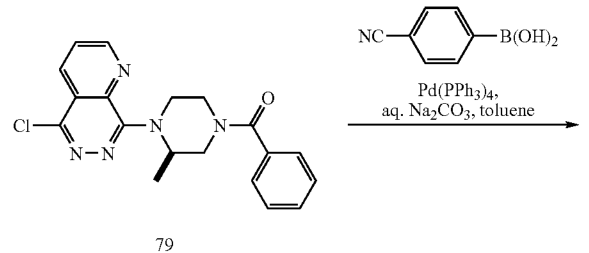

-continued

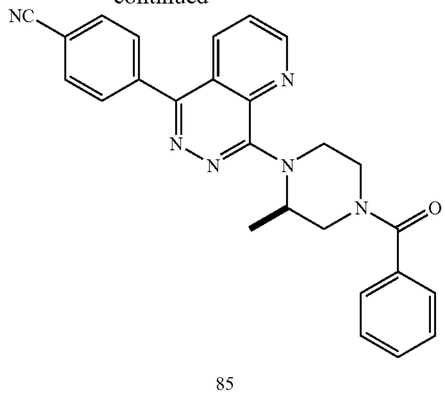

Using methods described in Example 6, and starting with (R)-(4-(5-chloropyrido[2,3-d]pyridazin-8-yl)-3-methylpiperazin-1-yl)(phenyl)methanone 79 (360 mg, 979 mmol), 2 M sodium carbonate (979 μl, 196 mmol), 4-cyanophenylboronic acid (216 mg, 1.47 mmol), and tetrakis(triphenylphosphine) palladium (57 mg, 49 μmol) afforded (R)-4-(8-(4-benzoyl-2-methylpiperazin-1-yl)pyrido[2,3-d]pyridazin-5-yl)benzonitrile 85 (138 mg, 32% yield) after chromatographic purification. MS 434.2 (calc'd) 435.1 (M+H, found).

EXAMPLE 43

Preparation of (R)-(3-methyl-4-(8-(4-(trifluoromethyl)phenyl)pyrido[3,2-d]pyridazin-5-yl)piperazin-1-yl)(phenyl)methanone

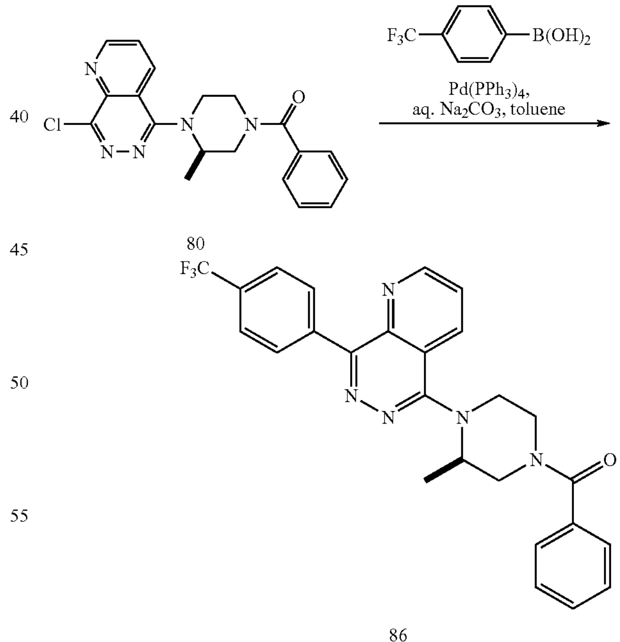

Using methods described in Example 6, and starting with (R)-(4-(8-chloropyrido[3,2-d]pyridazin-5-yl)-3-methylpiperazin-1-yl)(phenyl)methanone (180 mg, 489 μmol), 2 M sodium carbonate (489 μl, 979 μmol), tetrakis(triphenylphosphine)palladium (28 mg, 24 μmol), and 4-trifluoromethylphenylboronic acid (139 mg, 734 μmol) afforded (R)-(3- methyl-4-(8-(4-(trifluoromethyl)phenyl)pyrido[3,2-d]pyridazin-5-yl)piperazin-1-yl)(phenyl)methanone 86 after chromatographic purification. MS 477.2 (calc'd) 478.1 (M+H, found).

EXAMPLE 44

Smoothened Receptor Activity

Antagonist activity of compounds for mouse Smoothened was assessed by measuring inhibition of Luciferase activity in Shh-stimulated NIH-3T3 cells stably transfected with a luciferase reporter construct with 5 GLI binding sites upstream of a basal promoter, similar to methods described by others. Chen et al. (2002) *PNAS* 99 14071-14076; Taipale et al. (2000) *Nature* 406 1005-1009. Antagonist activity of compounds on human Smoothened was assessed by measuring inhibition of GLI1 transcription in Shh-stimulated HEPM cells (American Type Culture Collection, Manassas, Va. USA), similar to methods described by others. See U.S. Pat. No. 6,613,798. For this work GLI1 transcription in HEPM cells was measured using a Quantigene assay specific for GLI1 (Panomics Inc., Freemont, Calif., USA) in place of PCR based methods.

All exemplified compounds demonstrated antagonism of human Smoothened with $IC_{50}$'s of 1 μM or less.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of Formula I

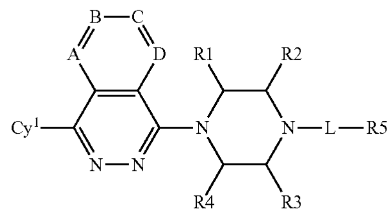

or a pharmaceutically acceptable salt thereof, wherein

A, B, C, and D are independently selected from CH or N, provided that at least one but no more than two of A, B, C, and D is N, $Cy^1$ is phenyl optionally substituted independently with 1-5 substituents, wherein the substituents are selected from the group consisting of $C_{1-8}$alkyl, $C_{2-8}$alkenyl, $C_{2-8}$alkynyl, $C_{1-6}$haloalkyl, halogen, cyano, hydroxy, oxo, —$OR^c$, —$NR^aR^b$, —$NR^aC$(═O)$R^b$, —C(═O)$OR^c$, —$R^cOC$(═O)$NR^aR^b$, —$R^cOH$, —C(═O)$NR^aR^b$, —OC(═O)$NR^aR^b$, —OC(═O)$R^c$—$NR^aC$(═O)$R^c$, —$R^bN(R^a)C$(═O)$R^c$, —$R^bN(R^a)C$(═O)$OR^c$, —$NR^aS$(═O)$_mR^c$, —S(═O)$_mNR^aR^b$, and —S(═O)$_mR^c$;

$R^1$, $R^2$, $R^3$, and $R^4$ are each independently selected from H, $C_{1-6}$alkyl, $C_{3-6}$cycloalkyl, $C_{1-6}$haloalkyl, oxo, —C(═O)$OR^a$, —$R^cOH$, —$OR^c$, —$NR^aR^b$, —$NR^aC$(═O)$R^b$, —C(═O)$OR^c$, —C(═O)$NR^aR^b$, —OC(═O)$R^c$, —$NR^aC$(═O)$R^c$, —$NR^aS$(═O)$_mR^c$, —S(═O)$_mNR^aR^b$, and —S(═O)$_mR^c$, provided that at least one of $R^1$, $R^2$, $R^3$, and $R^4$ is not H;

$R^a$, $R^b$, and $R^c$ are each independently selected from H, $C_{1-8}$alkyl, $C_{2-8}$alkenyl, $C_{2-8}$alkynyl, $C_{1-6}$haloalkyl, heterocyclyl, aryl, and heteroaryl;

m is 1 or 2;

L is —C(═O)— or —S(═O)$_m$—;

$R^5$ is —$NR^aR^b$ or $Cy^2$;

$Cy^2$ is a partially or fully saturated or unsaturated 6-membered monocyclic ring formed of carbon atoms optionally including 1-3 heteroatoms, wherein the ring is optionally substituted independently with 1-5 substituents, wherein the substituents are independently selected from the group consisting of $C_{1-8}$alkyl, $C_{2-8}$alkenyl, $C_{2-8}$alkynyl, $C_{1-6}$haloalkyl, halogen, cyano, hydroxy, oxo, —C(═O)$OR^c$, —$R^cOH$, —$OR^c$, —$NR^aR^b$, —$NR^aC$(═O)$R^b$, —C(═O)$NR^aR^b$, —OC(═O)$R^c$, —$NR^aC$(═O)$R^c$, —$NR^aS$(═O)$_mR^c$, —S(═O)$_mNR^aR^b$, and —S(═O)$_mR^c$.

2. The compound of claim 1 represented by Formula II

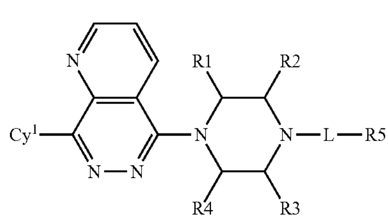

wherein $Cy^1$ is phenyl optionally substituted independently with 1-5 substituents, wherein the substituents are selected from the group consisting of $C_{1-8}$alkyl, $C_{2-8}$alkenyl, $C_{2-8}$alkynyl, $C_{1-6}$haloalkyl, halogen, cyano, hydroxy, oxo, —$OR^c$, —$NR^aR^b$, —$NR^aC$(═O)$R^b$, —C(═O)$OR^c$, —$R^cOC$(═O)$NR^aR^b$, —$R^cOH$, —C(═O)$NR^aR^b$, —OC(═O)$NR^aR^b$, —OC(═O)$R^c$—$NR^aC$(═O)$R^c$, —$R^bN(R^a)C$(═O)$R^c$, —$R^bN(R^a)C$(═O)$OR^c$, —$NR^aS$(═O)$_mR^c$, —S(═O)$_mNR^aR^b$, and —S(═O)$_mR^c$;

$R^1$, $R^2$, $R^3$, and $R^4$ are each independently selected from H, $C_{1-6}$alkyl, $C_{3-6}$cycloalkyl, $C_{1-6}$haloalkyl, oxo, —C(═O)$OR^a$, —$R^cOH$, —$OR^c$, —$NR^aR^b$, —$NR^aC$(═O)$R^b$, —C(═O)$OR^c$, —C(═O)$NR^aR^b$, —OC(═O)$R^c$, —$NR^aC$(═O)$R^c$, —$NR^aS$(═O)$_mR^c$, —S(═O)$_mNR^aR^b$, and —S(═O)$_mR^c$, provided that at least one of $R^1$, $R^2$, $R^3$, and $R^4$ is not H;

$R^a$, $R^b$, and $R^c$ are each independently selected from H, $C_{1-8}$alkyl, $C_{2-8}$alkenyl, $C_{2-8}$alkynyl, $C_{1-6}$haloalkyl, heterocyclyl, aryl, and heteroaryl;

m is 1 or 2;

L is —C(═O)— or —S(═O)$_m$—;

$R^5$ is —$NR^aR^b$ or $Cy^2$;

$Cy^2$ is a partially or fully saturated or unsaturated 6-membered monocyclic ring formed of carbon atoms optionally including 1-3 heteroatoms, wherein the ring is optionally substituted independently with 1-5 substituents, wherein the substituents are independently selected from the group consisting of $C_{1-8}$alkyl, $C_{2-8}$alkenyl, $C_{2-8}$alkynyl, $C_{1-6}$haloalkyl, halogen, cyano, hydroxy, oxo, —C(═O)$OR^c$, —$R^cOH$, —$OR^c$, —NR$^a$R$^b$, —NR$^a$C(=O)R$^b$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and —S(=O)$_m$R$^c$;

or a pharmaceutically salt thereof.

3. The compound of claim 1 represented by Formula III

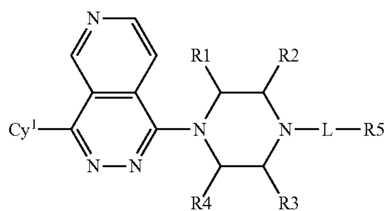

wherein

Cy$^1$ is phenyl optionally substituted independently with 1-5 substituents, wherein the substituents are selected from the group consisting of C$_{1-8}$alkyl, C$_{2-8}$alkenyl, C$_{2-8}$alkynyl, C$_{1-6}$haloalkyl, halogen, cyano, hydroxy, oxo, —OR$^c$, —NR$^a$R$^b$, —NR$^a$C(=O)R$^b$, —C(=O)OR$^c$, —R$^c$OC(=O)NR$^a$R$^b$, —R$^c$OH, —C(=O)NR$^a$R$^b$, —OC(=O)NR$^a$R$^b$, —OC(=O)R$^c$, —NR$^a$C(=O)R$^c$, —R$^b$N(R$^a$)C(=O)R$^c$, —R$^b$N(R$^a$)C(=O)OR$^c$, —NR$^a$S(=O)$_m$R$^c$, —S(=O)$_m$NR$^a$R$^b$, and —S(=O)$_m$R$^c$;

R$^1$, R$^2$, R$^3$, and R$^4$ are each independently selected from H, C$_{1-6}$alkyl, C$_{3-6}$cycloalkyl, C$_{1-6}$haloalkyl, oxo, —C(=O)OR$^a$, —R$^c$OH, —OR$^c$, —NR$^a$R$^b$, —NR$^a$C(=O)R$^b$, —C(=O)OR$^c$, —C(=O)NR$^a$R$^b$, —OC(=O)R$^c$—NR$^a$C(=O)R$^c$, —NR$^a$S(=O)$_m$R$^c$, —S(=O)$_m$NR$^a$R$^b$, and —S(=O)$_m$R$^c$, provided that at least one of R$^1$, R$^2$, R$^3$, and R$^4$ is not H;

R$^a$, R$^b$, and R$^c$ are each independently selected from H, C$_{1-8}$alkyl, C$_{2-8}$alkenyl, C$_{2-8}$alkynyl, C$_{1-6}$haloalkyl, heterocyclyl, aryl, and heteroaryl;

m is 1 or 2;

L is —C(=O)— or —S(=O)$_m$—;

R$^5$ is —NR$^a$R$^b$ or Cy$^2$;

Cy$^2$ is a partially or fully saturated or unsaturated 6-membered monocyclic ring formed of carbon atoms optionally including 1-3 heteroatoms, wherein the ring is optionally substituted independently with 1-5 substituents, wherein the substituents are independently selected from the group consisting of C$_{1-8}$alkyl, C$_{2-8}$alkenyl, C$_{2-8}$alkynyl, C$_{1-6}$haloalkyl, halogen, cyano, hydroxy, oxo, —C(=O)OR$^c$, —R$^c$OH, —OR$^c$, —NR$^a$R$^b$, —NR$^a$C(=O)R$^b$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and —S(=O)$_m$R$^c$;

or a pharmaceutically salt thereof.

4. The compound of claim 1 represented by Formula IV

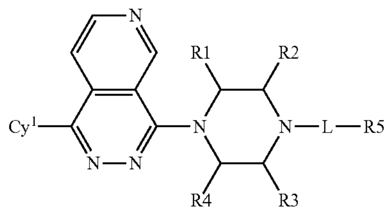

wherein

Cy$^1$ is phenyl optionally substituted independently with 1-5 substituents, wherein the substituents are selected from the group consisting of C$_{1-8}$alkyl, C$_{2-8}$alkenyl, C$_{2-8}$alkynyl, C$_{1-6}$haloalkyl, halogen, cyano, hydroxy, oxo, —OR$^c$, —NR$^a$R$^b$, NR$^a$C(=O)R$^b$, —C(=O)OR$^c$, —R$^c$OC(=O)NR$^a$R$^b$, —R$^c$OH, —C(=O)NR$^a$R$^b$, —OC(=O)NR$^a$R$^b$, —OC(=O)R$^c$, —NR$^a$C(=O)R$^c$, —R$^b$N(R$^a$)C(=O)R$^c$, —R$^b$N(R$^a$)C(=O)OR$^c$, —NR$^a$S(=O)$_m$R$^c$, —S(=O)$_m$NR$^a$R$^b$, and S(=O)$_m$R$^c$;

R$^1$, R$^2$, R$^3$, and R$^4$ are each independently selected from H, C$_{1-6}$alkyl, C$_{3-6}$cycloalkyl, C$_{1-6}$haloalkyl, oxo, —C(=O)OR$^a$, —R$^c$OH, —OR$^c$, —NR$^a$R$^b$, —NR$^a$C(=O)R$^b$, —C(=O)OR$^c$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and —S(=O)$_m$R$^c$, provided that at least one of R$^1$, R$^2$, R$^3$, and R$^4$ is not H;

R$^a$, R$^b$, and R$^c$ are each independently selected from H, C$_{1-8}$alkyl, C$_{2-8}$alkenyl, C$_{2-8}$alkynyl, C$_{1-6}$haloalkyl, heterocyclyl, aryl, and heteroaryl;

m is 1 or 2;

L is —C(=O)— or —S(=O)$_m$—;

R$^5$ is —NR$^a$R$^b$ or Cy$^2$;

Cy$^2$ is a partially or fully saturated or unsaturated 6-membered monocyclic ring formed of carbon atoms optionally including 1-3 heteroatoms, wherein the ring is optionally substituted independently with 1-5 substituents, wherein the substituents are independently selected from the group consisting of C$_{1-8}$alkyl, C$_{2-8}$alkenyl, C$_{2-8}$alkynyl, C$_{1-6}$haloalkyl, halogen, cyano, hydroxy, oxo, —C(=O)OR$^c$, —R$^c$OH, —OR$^c$, —NR$^a$R$^b$, —NR$^a$C(=O)R$^b$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and —S(=O)$_m$R$^c$;

or a pharmaceutically salt thereof.

5. The compound of claim 1 represented by Formula V

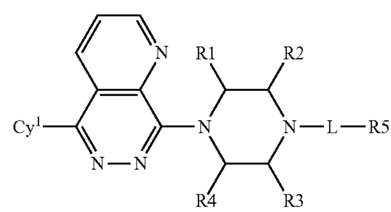

wherein

Cy$^1$ is phenyl optionally substituted independently with 1-5 substituents, wherein the substituents are selected from the group consisting of C$_{1-8}$alkyl, C$_{2-8}$alkenyl, C$_{2-8}$alkynyl, C$_{1-6}$haloalkyl, halogen, cyano, hydroxy, oxo, —OR$^c$, —NR$^a$R$^b$, NR$^a$C(=O)R$^b$, —C(=O)OR$^c$, —R$^c$OC(=O)NR$^a$R$^b$, —R$^c$OH, —C(=O)NR$^a$R$^b$, —OC(=O)NR$^a$R$^b$, —OC(=O)R$^c$, —NR$^a$C(=O)R$^c$, —R$^b$N(R$^a$)C(=O)R$^c$, —R$^b$N(R$^a$)C(=O)OR$^c$, —NR$^a$S(=O)$_m$R$^c$, —S(=O)$_m$NR$^a$R$^b$, and S(=O)$_m$R$^c$;

R$^1$, R$^2$, R$^3$, and R$^4$ are each independently selected from H, C$_{1-6}$alkyl, C$_{3-6}$cycloalkyl, C$_{1-6}$haloalkyl, oxo, —C(=O)OR$^a$, —R$^c$OH, —OR$^c$, —NR$^a$R$^b$, —NR$^a$C(=O)R$^b$, —C(=O)OR$^c$, —C(=O)NR$^a$R$^b$, —OC(=O)R$^c$, —NR$^a$C(=O)R$^c$, —NR$^a$S(=O)$_m$R$^c$, —S(=O)$_m$NR$^a$R$^b$, and —S(=O)$_m$R$^c$, provided that at least one of R$^1$, R$^2$, R$^3$, and R$^4$ is not H;

R$^a$, R$^b$, and R$^c$ are each independently selected from H, C$_{1-8}$alkyl, C$_{2-8}$alkenyl, C$_{2-8}$alkynyl, C$_{1-6}$haloalkyl, heterocyclyl, aryl, and heteroaryl;

m is 1 or 2;

L is —C(═O)— or —S(═O)$_m$—;

$R^5$ is —$NR^aR^b$ or $Cy^2$;

$Cy^2$ is a partially or fully saturated or unsaturated 6-membered monocyclic ring formed of carbon atoms optionally including 1-3 heteroatoms, wherein the ring is optionally substituted independently with 1-5 substituents, wherein the substituents are independently selected from the group consisting of $C_{1-8}$alkyl, $C_{2-8}$alkenyl, $C_{2-8}$alkynyl, $C_{1-6}$haloalkyl, halogen, cyano, hydroxy, oxo, —C(═O)$OR^c$, —$R^c$OH, —$OR^c$, —$NR^aR^b$, —$NR^a$C(═O)$R^b$, —C(═O)$NR^aR^b$, —OC(═O)$R^c$, —$NR^a$C(═O)$R^c$, —$NR^a$S(═O)$_m R^c$, —S(═O)$_m NR^aR^b$, and —S(═O)$_m R^c$;

or a pharmaceutically salt thereof.

6. The compound of claim 1 or a pharmaceutically acceptable salt thereof, wherein $Cy^1$ is unsubstituted phenyl.

7. The compound of claim 1, or a pharmaceutically acceptable salt thereof, wherein $Cy^1$ is phenyl substituted independently with 1-5 substituents, wherein the substituents are selected from the group consisting of $C_{1-8}$alkyl, $C_{1-6}$haloalkyl, halogen, cyano, —$OR^c$, —$NR^aR^b$, —$NR^a$C(═O)$R^b$, —C(═O)$OR^c$, —$R^c$OC(═O)$NR^aR^b$, —$R^c$OH, —C(═O)$NR^aR^b$, —OC(═O)$NR^aR^b$, —OC(═O)$R^c$, —$NR^a$C(═O)$R^c$, —$R^b$N($R^a$)C(═O)$R^c$, and —$R^b$N($R^a$)C(═O)$OR^c$.

8. The compound of claim 1 or a pharmaceutically acceptable salt thereof, wherein $R^1$, $R^2$, $R^3$, and $R^4$ are each independently selected from H, $C_{1-6}$alkyl and $C_{1-6}$haloalkyl, provided that at least one of $R^1$, $R^2$, $R^3$, and $R^4$ is not H.

9. The compound of claim 8 or a pharmaceutically acceptable salt thereof, wherein $R^1$, $R^2$, $R^3$ are each H, and $R^4$ is $C_{1-6}$alkyl.

10. The compound of claim 9 or a pharmaceutically acceptable salt thereof, wherein $R^4$ is methyl.

11. The compound of claim 8 or a pharmaceutically acceptable salt thereof, wherein $R^1$ and $R^3$ are each H, and $R^2$ and $R^4$ are each independently $C_{1-6}$alkyl.

12. The compound of claim 8 or a pharmaceutically acceptable salt thereof, wherein $R^2$ and $R^4$ are each methyl.

13. The compound of claim 8 or a pharmaceutically acceptable salt thereof, wherein $R^1$, $R^3$, and $R^4$ are each H, and $R^2$ is $C_{1-6}$alkyl.

14. The compound of claim 8 or a pharmaceutically acceptable salt thereof, wherein $R^1$, $R^2$, and $R^4$ are each H, and $R^3$ is $C_{1-6}$alkyl.

15. The compound of claim 8 or a pharmaceutically acceptable salt thereof, wherein $R^2$, $R^3$, and $R^4$ are each H, and $R^1$ is $C_{1-6}$alkyl.

16. The compound of claim 8 or a pharmaceutically acceptable salt thereof, wherein $R^1$ and $R^3$ are each independently $C_{1-6}$alkyl, and $R^2$ and $R^4$ are each H.

17. The compound of claim 1 or a pharmaceutically acceptable salt thereof, wherein L is —C(═O)—.

18. The compound of claim 1 or a pharmaceutically acceptable salt thereof, wherein L is —S(═O)$_2$—.

19. The compound of claim 1 or a pharmaceutically acceptable salt thereof, wherein L is —S(═O)—.

20. The compound of claim 1 or a pharmaceutically acceptable salt thereof, wherein $R^5$ is $Cy^2$.

21. The compound of claim 20 or a pharmaceutically acceptable salt thereof, wherein $Cy^2$ is phenyl optionally substituted independently with 1-5 substituents, wherein the substituents are selected from the group consisting of $C_{1-8}$alkyl, $C_{2-8}$alkenyl, $C_{2-8}$alkynyl, $C_{1-6}$haloalkyl, halogen, cyano, hydroxy, oxo, —C(═O)$OR^c$, —$R^c$OH, —$OR^c$, —$NR^aR^b$, —$NR^a$C(═O)$R^b$, —C(═O)$NR^aR^b$, —OC(═O)$R^c$, —$NR^a$C(═O)$R^c$, —$NR^a$S(═O)$_m R^c$, —S(═O)$_m NR^aR^b$, and —S(═O)$_m R^c$.

22. The compound of claim 21 or a pharmaceutically acceptable salt thereof, wherein $Cy^2$ is phenyl substituted independently with 1-5 substituents, wherein the substituents are selected from the group consisting of $C_{1-8}$alkyl, $C_{1-6}$haloalkyl, halogen, cyano, hydroxy and —$OR^c$.

23. The compound of claim 21 or a pharmaceutically acceptable salt thereof, wherein $Cy^2$ is unsubstituted phenyl.

24. The compound of claim 20 or a pharmaceutically acceptable salt thereof, wherein $Cy^2$ is cyclohexyl optionally substituted independently with 1-5 substituents, wherein the substituents are selected from the group consisting of $C_{1-8}$alkyl, $C_{2-8}$alkenyl, $C_{2-8}$alkynyl, $C_{1-6}$haloalkyl, halogen, cyano, hydroxy, oxo, —C(═O)$OR^c$, —$R^c$OH, —$OR^c$, —$NR^aR^b$, —$NR^a$C(═O)$R^b$, —C(═O)$NR^aR^b$, —OC(═O)$R^c$, —$NR^a$C(═O)$R^c$, —$NR^a$S(═O)$_m R^c$, —S(═O)$_m NR^aR^b$, and —S(═O)$_m R^c$.

25. The compound of claim 24 or a pharmaceutically acceptable salt thereof, wherein the substituents are selected from the group consisting of $C_{1-8}$alkyl, $C_{1-6}$haloalkyl, halogen, cyano, and hydroxy.

26. The compound of claim 20 or a pharmaceutically acceptable salt thereof, wherein $Cy^2$ is piperidyl optionally substituted independently with 1-5 substituents, wherein the substituents are selected from the group consisting of $C_{1-8}$alkyl, $C_{2-8}$alkenyl, $C_{2-8}$alkynyl, $C_{1-6}$haloalkyl, halogen, cyano, hydroxy, oxo, —C(═O)$OR^c$, —$R^c$OH, —$OR^c$, —$NR^aR^b$, $NR^a$C(═O)$R^b$, —C(═O)$NR^aR^b$, —OC(═O)$R^c$, —$NR^a$C(═O)$R^c$, —$NR^a$S(═O)$_m R^c$, —S(═O)$_m NR^aR^b$, and S(═O)$_m R^c$.

27. The compound of claim 26 or a pharmaceutically acceptable salt thereof, wherein piperidyl is unsubstituted.

28. The compound of claim 20 or a pharmaceutically acceptable salt thereof, wherein $Cy^2$ is morpholinyl optionally substituted independently with 1-5 substituents, wherein the substituents are selected from the group consisting of $C_{1-8}$alkyl, $C_{2-8}$alkenyl, $C_{2-8}$alkynyl, $C_{1-6}$haloalkyl, halogen, cyano, hydroxy, oxo, —C(═O)$OR^c$, —$R^c$OH, —$OR^c$, —$NR^aR^b$, —$NR^a$C(═O)$R^b$, —C(═O)$NR^aR^b$, —OC(═O)$R^c$, —$NR^a$C(═O)$R^c$, —$NR^a$S(═O)$_m R^c$, —S(═O)$_m NR^aR^b$, and —S(═O)$_m R^c$.

29. The compound of claim 20 or a pharmaceutically acceptable salt thereof, wherein $Cy^2$ is tetrahydro-2H-pyranyl optionally substituted independently with 1-5 substituents, wherein the substituents are selected from the group consisting of $C_{1-8}$alkyl, $C_{2-8}$alkenyl, $C_{2-8}$alkynyl $C_{1-6}$haloalkyl, halogen, cyano, hydroxy, oxo, —C(═O)$OR^c$, —$R^c$OH, —$OR^c$, —$NR^aR^b$, —$NR^a$C(═O)$R^b$, —C(═O)$NR^aR^b$, —OC(═O)$R^c$, —$NR^a$C(═O)$R^c$, —$NR^a$S(═O)$_m R^c$, —S(═O)$_m NR^aR^b$, and —S(═O)$_m R^c$.

30. The compound of claim 1, wherein the compound is selected from the group consisting of:

(S)-(2-methyl-4-(1-phenylpyrido[3,4-d]pyridazin-4-yl)piperazin-1-yl)(phenyl)methanone, (S)-(2-methyl-4-(1-(4-(trifluoromethyl)phenyl)pyrido[3,4-d]pyridazin-4-yl)piperazin-1-yl)(phenyl)methanone, (S)-(2-methyl-4-(1-(4-(trifluoromethyl)phenyl)pyrido[3,4-d]pyridazin-4-yl)piperazin-1-yl)(piperidin-1-yl)methanone, (S)-(4-(1-(4-(hydroxymethyl)phenyl)pyrido[3,4-d]pyridazin-4-yl)-2-methylpiperazin-1-yl)(piperidin-1-yl)methanone, (S)-(4-(4-(3-methyl-4-(piperidine-1-carbonyl)piperazin-1-yl)pyrido[3,4-d]pyridazin-1-yl)phenyl)methyl carbamate, ((R)-4-(1-(4-chloro-2-fluorophenyl)pyrido[3,4-d]pyridazin-4-yl)-3-methylpiperazin-1-yl)(phenyl)methanone, (R)-(4,4-difluorocyclohexyl)(3-methyl-4-(1-phenylpyrido[3,4-d]pyridazin-4-yl)piperazin-1-yl)methanone, (R)-cyclohexyl(3-methyl-4-(1-phenylpyrido[3,4-d]pyridazin-4-yl)piperazin-1-yl)methanone, ((R)-4-(1-(4-chloro-2-fluorophenyl)pyrido[3,4-d]pyridazin-4-yl)-3-methylpiperazin-1-yl)(cyclohexyl)methanone, (R)-(3-methyl-4-(1-(4-(trifluoromethyl)phenyl)pyrido[3,4-d]pyridazin-4-yl)piperazin-1-yl)(phenyl)methanone, (R)-(3-methyl-4-(1-phenylpyrido[3,4-d]pyridazin-4-yl)piperazin-1-yl)(phenyl)methanone, ((1S,4S)-4-hydroxycyclohexyl)((R)-3-methyl-4-(1-phenylpyrido[3,4-d]pyridazin-4-yl)piperazin-1-yl)methanone, ((1R,4R)-4-hydroxycyclohexyl)((R)-3-methyl-4-(1-phenylpyrido[3,4-d]pyridazin-4-yl)piperazin-1-yl)methanone, (R)-(3-methyl-4-(4-phenylpyrido[4,3-d]pyridazin-1-yl)piperazin-1-yl)(phenyl)methanone, (R)-(3-methyl-4-(1-phenylpyrido[4,3-d]pyridazin-4-yl)piperazin-1-yl)(tetrahydro-2H-pyran-4-yl)methanone, (S)-(3-methyl-4-(1-phenylpyrido[3,4-d]pyridazin-4-yl)piperazin-1-yl)(phenyl)methanone, (S)-(4,4-difluorocyclohexyl)(3-methyl-4-(1-phenylpyrido[3,4-d]pyridazin-4-yl)piperazin-1-yl)methanone, (R)-(3-methyl-4-(1-phenylpyrido[3,4-d]pyridazin-4-yl)piperazin-1-yl)(morpholino)methanone, (R)—N,3-dimethyl-N-phenyl-4-(1-phenylpyrido[3,4-d]pyridazin-4-yl)piperazine-1-carboxamide, (R)-(3-methyl-4-(1-phenylpyrido[3,4-d]pyridazin-4-yl)piperazin-1-yl)(piperidin-1-yl)methanone, (R)—N,N,3-trimethyl-4-(1-phenylpyrido[3,4-d]pyridazin-4-yl)piperazine-1-carboxamide, (R)-(4,4-difluoropiperidin-1-yl)(3-methyl-4-(1-phenylpyrido[3,4-d]pyridazin-4-yl)piperazin-1-yl)methanone, (4,4-difluorocyclohexyl)((2S,5R)-2,5-dimethyl-4-(1-phenylpyrido[3,4-d]pyridazin-4-yl)piperazin-1-yl)methanone, (4,4-difluorocyclohexyl)((2R,5S)-2,5-dimethyl-4-(1-phenylpyrido[3,4-d]pyridazin-4-yl)piperazin-1-yl)methanone, (S)-(4,4-difluoropiperidin-1-yl)(2-methyl-4-(1-(4-(trifluoromethyl)phenyl)pyrido[3,4-d]pyridazin-4-yl)piperazin-1-yl)methanone, (S)-methyl(4-(4-(4-(4,4-difluorocyclohexanecarbonyl)-3-methylpiperazin-1-yl)pyrido[3,4-d]pyridazin-1-yl)phenyl)methylcarbamate, (S)—N-((4-(4-(4-(4,4-difluorocyclohexanecarbonyl)-3-methylpiperazin-1-yl)pyrido[3,4-d]pyridazin-1-yl)phenyl)methyl)acetamide, (S)-(4-(4-(4-(4,4-difluorocyclohexanecarbonyl)-3-methylpiperazin-1-yl)pyrido[3,4-d]pyridazin-1-yl)phenyl)methyl carbamate, (R)-(4,4-difluorocyclohexyl)(3-methyl-4-(1-(4-(trifluoromethyl)phenyl)pyrido[3,4-d]pyridazin-4-yl)piperazin-1-yl)methanone, (R)-(3-methyl-4-(1-(4-(trifluoromethoxy)phenyl)pyrido[3,4-d]pyridazin-4-yl)piperazin-1-yl)(phenyl)methanone, (R)-4-(4-(4-(4,4-difluorocyclohexanecarbonyl)-2-methylpiperazin-1-yl)pyrido[3,4-d]pyridazin-1-yl)benzonitrile, (R)-4-(4-(4-benzoyl-2-methylpiperazin-1-yl)pyrido[3,4-d]pyridazin-1-yl)benzonitrile, (R)-4-(4-(4-benzoyl-2-methylpiperazin-1-yl)pyrido[3,4-d]pyridazin-1-yl)benzamide, (R)-(4-(1-(4-fluorophenyl)pyrido[3,4-d]pyridazin-4-yl)-3-methylpiperazin-1-yl)(phenyl)methanone, (R)-(4-(1-(4-(hydroxymethyl)phenyl)pyrido[3,4-d]pyridazin-4-yl)-3-methylpiperazin-1-yl)(phenyl)methanone, (S)-(2-methyl-4-(5-phenylpyrido[2,3-d]pyridazin-8-yl)piperazin-1-yl)(phenyl)methanone, (R)-(3-methyl-4-(5-phenylpyrido[2,3-d]pyridazin-8-yl)piperazin-1-yl)(phenyl)methanone, (R)-(3-methyl-4-(8-phenylpyrido[3,2-d]pyridazin-5-yl)piperazin-1-yl)(phenyl)methanone, (R)-(4-(5-(4-(hydroxymethyl)phenyl)pyrido[2,3-d]pyridazin-8-yl)-3-methylpiperazin-1-yl)(phenyl)methanone, ((R)-4-(5-(4-chloro-2-fluorophenyl)pyrido[2,3-d]pyridazin-8-yl)-3-methylpiperazin-1-yl)(phenyl)methanone, (R)-(3-methyl-4-(5-(4-(trifluoromethyl)phenyl)pyrido[2,3-d]pyridazin-8-yl)piperazin-1-yl)(phenyl)methanone, (R)-4-(8-(4-benzoyl-2-methylpiperazin-1-yl)pyrido[2,3-d]pyridazin-5-yl)benzonitrile, and (R)-(3-methyl-4-(8-(4-(trifluoromethyl)phenyl)pyrido[3,2-d]pyridazin-5-yl)piperazin-1-yl)(phenyl)methanone, or a pharmaceutically acceptable salt thereof.

31. A pharmaceutical composition comprising a compound of claim 1 or a pharmaceutically acceptable salt thereof and a pharmaceutically acceptable carrier.

32. A pharmaceutical composition comprising a compound of claim 30 or a pharmaceutically acceptable salt thereof and a pharmaceutically acceptable carrier.

* * * * *